US010456445B2

United States Patent
Briscoe et al.

(10) Patent No.: US 10,456,445 B2
(45) Date of Patent: Oct. 29, 2019

(54) METHODS AND COMPOSITIONS FOR IMMUNOMODULATION

(71) Applicant: CHILDREN'S MEDICAL CENTER CORPORATION, Boston, MA (US)

(72) Inventors: David M. Briscoe, Sharon, MA (US); Michael Klagsbrun, Newton, MA (US); Sarah Bruneau, Boston, MA (US); Nora Kochupurakkal, Boston, MA (US); Hironao Nakayama, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 15/314,970

(22) PCT Filed: Jun. 1, 2015

(86) PCT No.: PCT/US2015/033510
§ 371 (c)(1),
(2) Date: Nov. 30, 2016

(87) PCT Pub. No.: WO2015/187541
PCT Pub. Date: Dec. 10, 2015

(65) Prior Publication Data
US 2017/0100456 A1    Apr. 13, 2017

Related U.S. Application Data

(60) Provisional application No. 62/006,441, filed on Jun. 2, 2014.

(51) Int. Cl.
*A61K 38/17* (2006.01)
*A61K 38/48* (2006.01)
*A61K 39/00* (2006.01)
*C07K 16/18* (2006.01)
*C07K 16/28* (2006.01)
*A61K 45/06* (2006.01)

(52) U.S. Cl.
CPC ........ *A61K 38/1709* (2013.01); *A61K 38/177* (2013.01); *A61K 38/482* (2013.01); *A61K 45/06* (2013.01); *C07K 16/18* (2013.01); *C07K 16/28* (2013.01); *C07K 16/2803* (2013.01); *C12Y 304/21* (2013.01); *C12Y 304/21075* (2013.01); *A61K 2039/505* (2013.01); *C07K 2317/76* (2013.01)

(58) Field of Classification Search
CPC .......... A61K 2039/505; A61K 2300/00; A61K 38/177; A61K 38/1709; C07K 2317/76; C07K 16/18; C07K 16/28; C07K 16/2803
See application file for complete search history.

(56) References Cited

U.S. PATENT DOCUMENTS

| | | | |
|---|---|---|---|
| 2007/0054852 A1* | 3/2007 | Lin | A61K 38/1703 514/16.5 |
| 2011/0064739 A1 | 3/2011 | Borlak et al. | |
| 2013/0287726 A1 | 10/2013 | Neufeld et al. | |
| 2014/0066360 A1 | 3/2014 | Gounni | |

OTHER PUBLICATIONS

Guo H-F., et al. Mechanistic basis for the potent anti-angiogenic activity of semaphorin 3F. Biochemistry, 2013, vol. 52(43), p. 1-17.*
Bielenberg et al. Semaphorin 3F, a chemorepulsant for endothelial cells, induces a poorly vascularized, encapsulated, nonmetastatic tumor phenotype. J Clin Invest. 114(9):1260-71 (2004).
Delgoffe et al., Regulatory T cell stability is maintained by a neuropilin-1:semaphorin-4a axis. Nature 501 7466):1-16 (2013).
Hansen et al., Neuropilin 1 deficiency on CD4+Foxp3+ regulatory T cells impairs mouse melanoma growth. J Exp Med. 209(11):2001-16 (2012).
Weiss et al., Neuropilin 1 is expressed on thymus-derived natural regulatory T cells, but not mucosa-generated induced Foxp3+ T reg cells. J Exp Med. 24;209(10):1723-42, (2012) S1. Epub Sep. 10, 2012.
Kumanogoh et al., "Immunological functions of the neuropilins and plexins as receptors for semaphorins." Nature Reviews Immunology 13(11):802-814 (2013).
Shimizu et al., "ABL2/ARG tyrosine kinase mediates SEMA3F-induced RhoA inactivation and cytoskeleton collapse in human glioma cells." Journal of Biological Chemistry 283(40): 27230-27238 (2008).
Lepelletier et al., "Immunosuppressive role of semaphorin-3A on T cell proliferation is mediated by inhibition of actin cytoskeleton reorganization." European Journal of Immunology 36(7):1782-1793 (2006).
Mendes-Da-Cruz et al., "Semaphorin 3F and neuropilin-2 control the migration of human T-cell precursors." PloS One 9(7):e103405 (2014).
Nakayama et al., "Regulation of mTOR signaling by semaphorin 3F-neuropilin 2 interactions in vitro and in vivo." Scientific Reports 5(1):11789 (2015).
Sakurai et al., "Semaphorin signaling in angiogenesis, lymphangiogenesis and cancer." Cell Research 22(1):23-32 (2012).
Chabbert-De Ponnat et al., "Antiproliferative effect of semaphorin 3F on human melanoma cell lines." The Journal of Investigative Dermatology 126(10):2343-2345 (2006).
Hida "Neuropilins as Common Targeting Molecules on Tumor and Endothelial Cells to Inhibit Metastasis." Biotherapy 22(2):80-86 (2008) [Partial English Translation Included].

(Continued)

*Primary Examiner* — Karen S. Weiler
*Assistant Examiner* — Bruce D. Hissong
(74) *Attorney, Agent, or Firm* — Nixon Peabody LLP; David S. Resnick; Nicole D. Kling

(57) ABSTRACT

The methods and uses described herein relate to the modulation of the immune system by modulation of Sema3F levels and/or activity, e.g. suppressing allograft rejection or inflammation by administering a Sema3F agonist or increasing an immune response by administering a Sema3F inhibitor.

24 Claims, 43 Drawing Sheets
Specification includes a Sequence Listing.

(56) References Cited

OTHER PUBLICATIONS

Kessler et al., "Semaphorin-3F is an inhibitor of tumor angiogenesis." Cancer Research 64(3):1008-1015 (2004).
Parker et al., "Furin processing of semaphorin 3F determines its anti-angiogenic activity by regulating direct binding and competition for neuropilin." Biochemistry 49(19):4068-4075 (2010).

* cited by examiner

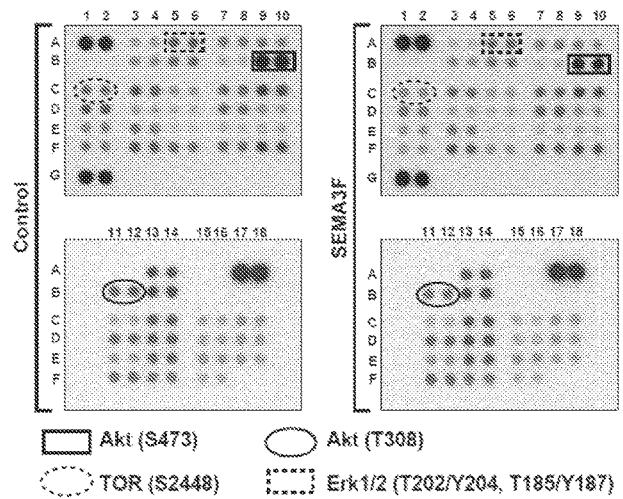
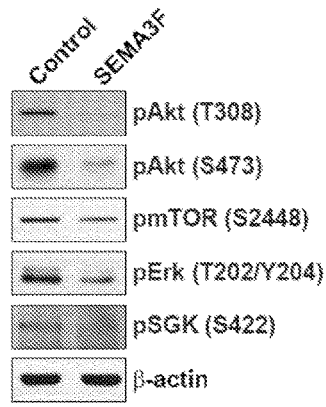
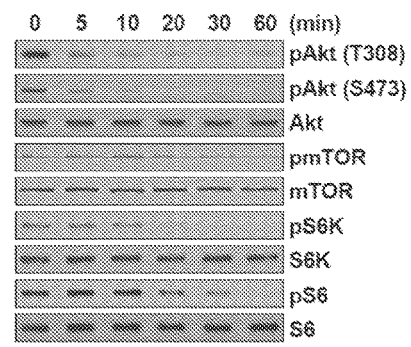
Fig. 28A
Fig. 28B
Fig. 28C
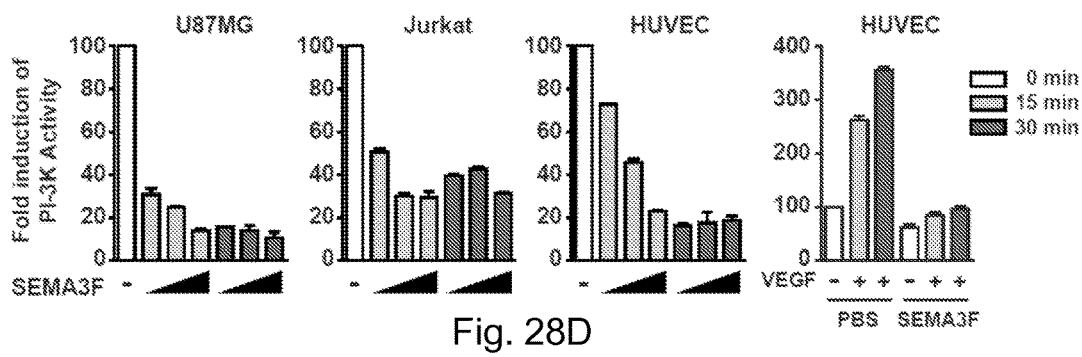
Fig. 28D

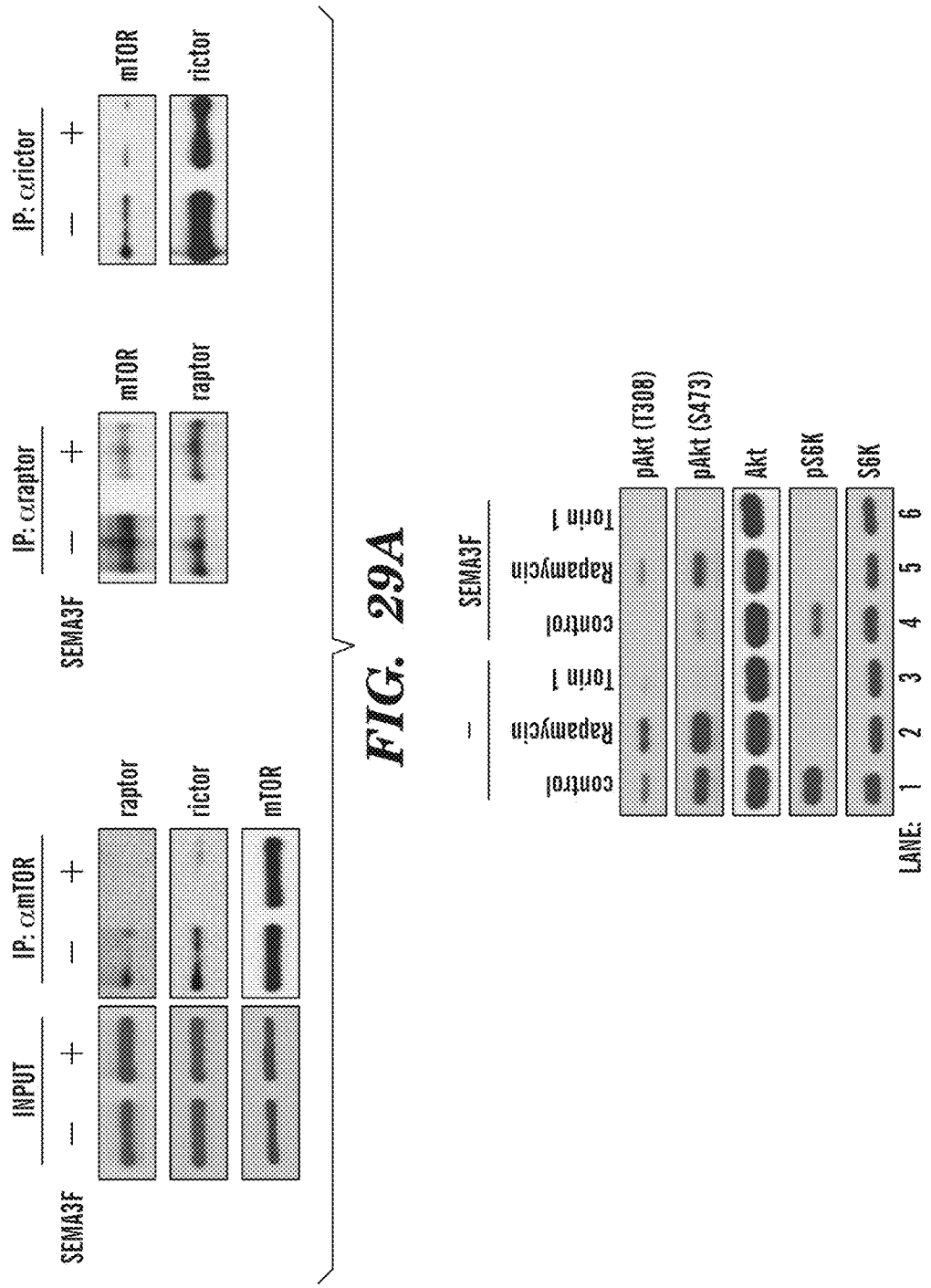

Day 5 Post Transplantation, n=6 mice

METHODS AND COMPOSITIONS FOR IMMUNOMODULATION

CROSS-REFERENCE TO RELATED APPLICATIONS

This application is a 35 U.S.C. § 371 National Phase Entry Application of International Application No. PCT/US2015/033510 filed Jun. 1, 2015, which designates the U.S. and claims benefit under 35 U.S.C. § 119(e) of U.S. Provisional Application No. 62/006,441 filed Jun. 2, 2014, the contents of which are incorporated herein by reference in their entirety.

GOVERNMENT SUPPORT

This invention was made with government support under grant number AI092305 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on May 29, 2015, is named 701039-080591-PCT_SL.txt and is 63,543 bytes in size.

TECHNICAL FIELD

The technology described herein relates to immunomodulation.

BACKGROUND

The class 3 family of semaphorins (Sema3A-G) bind to Neuropilin and Plexin family proteins and elicit regulatory signals that inhibit cellular migration and proliferation. Specifically, the binding of SEMA3A to NRP-1 and SEMA3F to NRP-2 elicits inhibitory signals in neuronal cells and in vascular endothelial cells.

SUMMARY

As described herein, the inventors have discovered that Sema3F has immunomodulatory properties and in part this effect is mediated via interaction with NRP-2 and Plexin A1. Accordingly, provided herein are immunomodulatory methods based on the manipulation of SEMA3F binding to its receptors and associated signaling. Non-limiting examples include suppression of the immune system or immune response by increasing or enhancing the interaction of Sema3F and NRP-2, and/or upregulating the immune system or immune response by decreasing the activity and/or interaction of Sema3F and NRP-2.

In one aspect, described herein is a method of suppressing the immune system in a subject, the method comprising administering a Sema3F agonist to a subject in need thereof. In one aspect, described herein is a method of suppressing allograft rejection, the method comprising administering a Sema3F agonist to an allograft recipient, whereby immune rejection of the allograft is suppressed. In one aspect, described herein is a method of treating an inflammatory condition in a subject in need of thereof, the method comprising administering a Sema3F agonist to the subject. In some embodiments, the inflammatory condition is an autoimmune disease. In some embodiments, the autoimmune disease is selected from the group consisting of Type 1 diabetes; systemic lupus erythematosus; rheumatoid arthritis; psoriasis; inflammatory bowel disease; Crohn's disease; and autoimmune thyroiditis. In some embodiments, the inflammatory condition is a local condition. In some embodiments, the local inflammatory condition is selected from the group consisting of a rash and an allergic reaction.

In some embodiments, the Sema3F agonist is a Sema3F polypeptide or a nucleic acid encoding a Sema3F polypeptide. In some embodiments, the Sema3F polypeptide comprises the sequence of SEQ ID NO: 5. In some embodiments, the Sema3F polypeptide can bind a Sema3F receptor. In some embodiments, the Sema3F polypeptide can bind a domain of NRP-2 selected from the group consisting of the A1; the A2; the B1; and the B2 domain. In some embodiments, the Sema3F agonist is a furin-like inhibitor. In some embodiments, the Sema3F agonist is administered intravenously. In some embodiments, the Sema3F agonist is administered intramuscularly, subcutaneously, or intradermally. In some embodiments, the Sema3F agonist is administered locally to a site of inflammation. In some embodiments, the method further comprises administering an additional anti-inflammatory agent. In some embodiments, the additional anti-inflammatory agent is selected from the group consisting of a steroid; a calcineurin inhibitor; an mTOR inhibitor (e.g. rapamycin) or an analogue thereof; and an anti-proliferative agent.

In one aspect, described herein is a method of increasing an immune response in a subject in need thereof, the method comprising administering one or more of a Sema3F inhibitor or NRP-2 inhibitor or Plexin A1 inhibitor to the subject. In some embodiments, the Sema3F inhibitor is an anti-Sema3F antibody reagent. In some embodiments, the NRP-2 inhibitor is an anti-NRP-2 antibody reagent. In some embodiments, the Sema3F inhibitor is a soluble NRP-2 receptor. In some embodiments, the Sema3F inhibitor is a soluble fragment of the NRP-2 receptor comprising at least one domain selected from the group consisting of the A1, the A2, the B1 or the B2 domain. In some embodiments, the Sema3F inhibitor is a furin-like polypeptide or a nucleic acid encoding a furin-like polypeptide.

BRIEF DESCRIPTION OF THE DRAWINGS

FIG. 26 depicts a graph of NPR-2 expression as evaluated by qPCR on unactivated and mitogen (Anti-CD3/CD28) activated human CD4+ T cells. FIG. 26B depicts a graph of NRP-2 expression evaluated by FACS on the CD4+ subset of human peripheral blood cells isolated by Ficoll separation. FIG. 26C depicts a graph of CD4, FoxP3 and NRP-2 protein levels in peripheral blood cells as evaluated by FACS. This data is similar to that shown in FIG. 22.

FIG. 27A demonstrates FACS analysis of NRP-2 on CD4+ T cells within murine spleen and lymph node. FIG. 27B depicts graphs of CD4+ T cells isolated by negative selection from Murine Spleen. Expression of NRP-2 was evaluated by qPCR on unactivated and mitogen (Anti-CD3/CD28) activated cells. FIG. 27C depicts graphs of Plexin A family molecule expression on isolated CD4+ T cells. FIG. 27D depicts expression of NRP-2 on Foxp3+ and Foxp3 negative subsets of CD4+ T cells isolated by negative selection from Murine Spleen. FIG. 27E depicts NRP-2 expression on isolated Splenic CD4+ T cells that were mitogen activated (anti-CD3-1 mcg/ml). FIG. 27F depicts NRP-1/2 expression on CD4+ T cells driven to differentiation into inducted Treg cells in standard culture medium (mitogen+TGFb+anti-IL-4+anti-IFNg+retinoic acid). These data are similar to that shown in FIGS. 7 and 9.

FIGS. 28A-28D show data demonstrating that SEMA3F inhibits the phosphorylation of Akt, mTOR and S6K. FIG. 28A depicts U87MG cells untreated (control) or following treatment with SEMA3F (640 ng/ml) for 30 minutes. Cell lysates were evaluated by phosphoprotein kinase antibody array. The intensity of each dot/phosphoprotein was measured using Image J software, as shown in Table 1. FIG. 28B depicts results of the array validated by Western blot analysis. FIG. 28C depicts U87MG cells treated with SEMA3F (640 ng/ml) as a time course up to 60 minutes and were analyzed by Western blot. FIGS. 28B-28C are representative of 3 independent experiments. FIG. 28D depicts U87MG, Jurkat and HUVEC cells treated with SEMA3F (200, 600, 1800 ng/ml, bars from left to right) for 15 minutes (grey bars) or 30 minutes (black bars); as a positive control, HUVEC were treated with VEGF-A (25 ng/ml) for 15 and 30 minutes. In addition, HUVEC were pre-treated with SEMA3F (1800 ng/ml) or PBS as a control for 30 minutes and subsequently VEGF-A (25 ng/ml) was added to the culture for 15 and 30 minutes. PI-3K activity was analyzed by ELISA according to the manufacturer's instructions. Data represent the mean±SD of 3 experiments.

FIGS. 29A-29D show data demonstrating that SEMA3F disrupts both mTORC1 and mTORC2 complex formation. FIG. 29A depicts U87MG cells treated with SEMA3F (640 ng/ml) for 30 minutes and subjected to immunoprecipitation and Western blot analysis with anti-mTOR, -raptor and -rictor as illustrated. FIG. 29B depicts U87MG cells treated with rapamycin (10 nM) or Torn 1 (10 nM) for 30 minutes, prior to SEMA3F (640 ng/ml) treatment for 60 minutes; lysates were analyzed by Western blot. FIG. 29C depicts bar graphs representing densitometric analysis of the illustrated blot showing the fold change in intensity (mean±SD) relative to the untreated control (*, p<0.01; **, p<0.001 vs. untreated control). FIG. 29D depicts U87MG cells transiently transfected with a pcDNA3.1 empty vector or with constitutively active Akt (2DAkt). Cells were treated with SEMA3F (640 ng/ml) and lysates were analyzed by Western blot. All data are representative of 3 independent experiments.

FIG. 30A depicts U87MG cells treated with SEMA3F (640 ng/ml), rapamycin (10 nM) or Torn 1 (10 nM) for 30 minutes. Subsequently, cells were stained with Alexa Fluor 488 phalloidin and Hoechst 33342 to identify F-actin cytoskeleton stress fibers and cellular nuclei, respectively. Representative cellular staining of is shown in each panel; the bar graph shows the mean±SD number of fibers/cell in an average of 3 independent experiments. The scale bar indicates 20 μm. FIG. 30B depicts U87MG cells transiently transfected with a pcDNA3.1 empty vector or with a wild type (WT) mTOR plasmid and after 18 hours treated with SEMA3F (640 ng/ml) for 30 minutes. Cells were stained as described above in FIG. 30A. Representative cellular staining is shown; bar graph represents the number of fibers/cell (mean±SD) from 3 independent experiments. FIG. 30C depicts U87MG cells transfected with control siRNA or with raptor- or rictor-specific siRNAs (20 nM). After 48 hours, they were treated with SEMA3F for 30 minutes and stained with Alexa Fluor 488 phalloidin and Hoechst 33342 as above. The number of stress fibers was evaluated in 3 independent experiments and shown as the mean±SD. FIG. 30D depicts U87MG cells transiently transfected with pcDNA3.1 empty vector or with our WT mTOR plasmid. After 18 hours, the cells were treated with SEMA3F (640 ng/ml) for 10 minutes and RhoA activity was evaluated. FIG. 30E depicts U87MG cells transfected with control siRNA or with raptor- or rictor-specific siRNAs (20 nM), were treated with SEMA3F (640 ng/ml) for 10 minutes and RhoA activity was analyzed. In FIGS. 30D-30E, the intensity of active RhoA was normalized to respective total RhoA; the numbers below each gel lane represent the fold-change in intensity relative to control. FIGS. 30D-30E are representative of 3 independent experiments.

FIGS. 31A-31B depict U87MG cells transiently co-transfected with a full-length human VEGF promoter luciferase plasmid and a pGL4.74[hRluc/TK] plasmid as an internal control. Cells were treated with SEMA3F (640 ng/ml for 30 minutes) prior to the addition of DFO (250 μM) or the culture of cells in a hypoxia chamber (1% O2). After 18 hours, VEGF promoter luciferase activity was analyzed. FIG. 31C depicts a graph of U87MG cells transiently cotransfected with our VEGF promoter luciferase and pGL4.74[hRluc/TK] plasmids and with either a pcDNA3.1 empty vector or our constitutively active Akt (2DAkt). The cells were treated with SEMA3F for 30 minutes prior to the addition of DFO. After 18 hours, VEGF promoter luciferase activity was analyzed. FIG. 31D depicts a graph of parental U87MG cells treated with SEMA3F, rapamycin (10 nM), Torn 1 (10 nM) alone or in combination as indicated for 30 minutes prior to the addition of DFO, and culture supernatants were collected after 18 hours; VEGF protein levels were analyzed by ELISA. In each panel data are representative of 3 independent experiments. Bar graphs represent the mean±SD of n=3 experiments performed in triplicate, *, p<0.01 vs. control.

FIG. 32A depicts parental U87MG cells (Mock) and human SEMA3F stable clones (S3F) implanted into nude mice subcutaneously (1×106 cells/injection). The insert shows Western blot analysis of SEMA3F expression in each cell line. Tumor size was measured using standard calipers at the indicated time points. Numbers in parentheses represent the number of animals in each group. FIG. 32B depicts representative immunohistochemical anti-CD31 staining of tumors harvested after 24 days. FIG. 32C depicts U87MG cells (1×106 cells/injection) administrated subcutaneously into nude mice. After 2 days, control (Ad-Cont) or human SEMA3F-His (Ad-3F)-recombinant adenovirus (1×109 pfu) were injected intravenously via the tail vein. Tumor size was measured using a standard calipers at the indicated time points. Numbers in parentheses represent the number of animals in each group. Mice were sacrificed on day 14. The insert shows SEMA3F expression within the liver (on day 14) by Western blot analysis using an anti-His antibody. FIG. 32D depicts representative immunohistochemical staining of tumors with anti-CD31. FIG. 32E depicts western blot analysis of Akt/mTOR signaling pathway within tumor samples. FIGS. 32B, 32D, and 32E are representative results of 3 independent experiments.

FIG. 34A depicts a Western blot of the expression of pAkt, pmTOR and pS6K in U87MG cells treated with SEMA3F or PBS for 60 minutes and. FIG. 34B depicts a Western blot. U87MG cells were transfected with control or Plexin A1-specific siRNA (20 nM). After 48 hours, cells were treated with SEMA3F (640 ng/ml) for 30 and 60 minutes, and were analyzed by Western blot. FIG. 34C depicts NRP2 and Plexin A1 expression analyzed by Western blot with multiple cell lines. FIG. 34D depicts a Western blot of multiple NRP2-expressing cell lines were treated with SEMA3F for 30 minutes. All data presented are representative of 3 independent experiments.

FIG. 34A depicts a Western blot. U87MG cells were transiently transfected with a pcDNA3.1 empty vector or with constitutively active Akt (2DAkt). Cells were treated with SEMA3F (640 ng/ml) and lysates were analyzed by Western blot. FIG. 35B depicts a Western blot. U87MG cells were transiently transfected with a pcDNA3.1 empty vector or with 2DAkt. Cells were treated with SEMA3F (640 ng/ml) for 30 minutes and were subjected to immunoprecipitation and Western blot analysis with anti-mTOR, and anti-rictor as illustrated.

In FIGS. 2, 6 and 32 an Adenovirus containing Sema3F or an empty control was administered into mice. In this Figure, it is demonstrated that this approach results in Sema3F production. Shown on the right is a Western Blot, illustrating the infection and production of Sema3F by the liver. Shown on the left, by ELISA, it is observed that Sema3F levels peak on day 14 following administration. Thus, for FIGS. 2, 6 and 32 it is likely that Sema3F peaked in expression 14 days after administration and that levels decreased after day 23.

DETAILED DESCRIPTION

Figure 1:
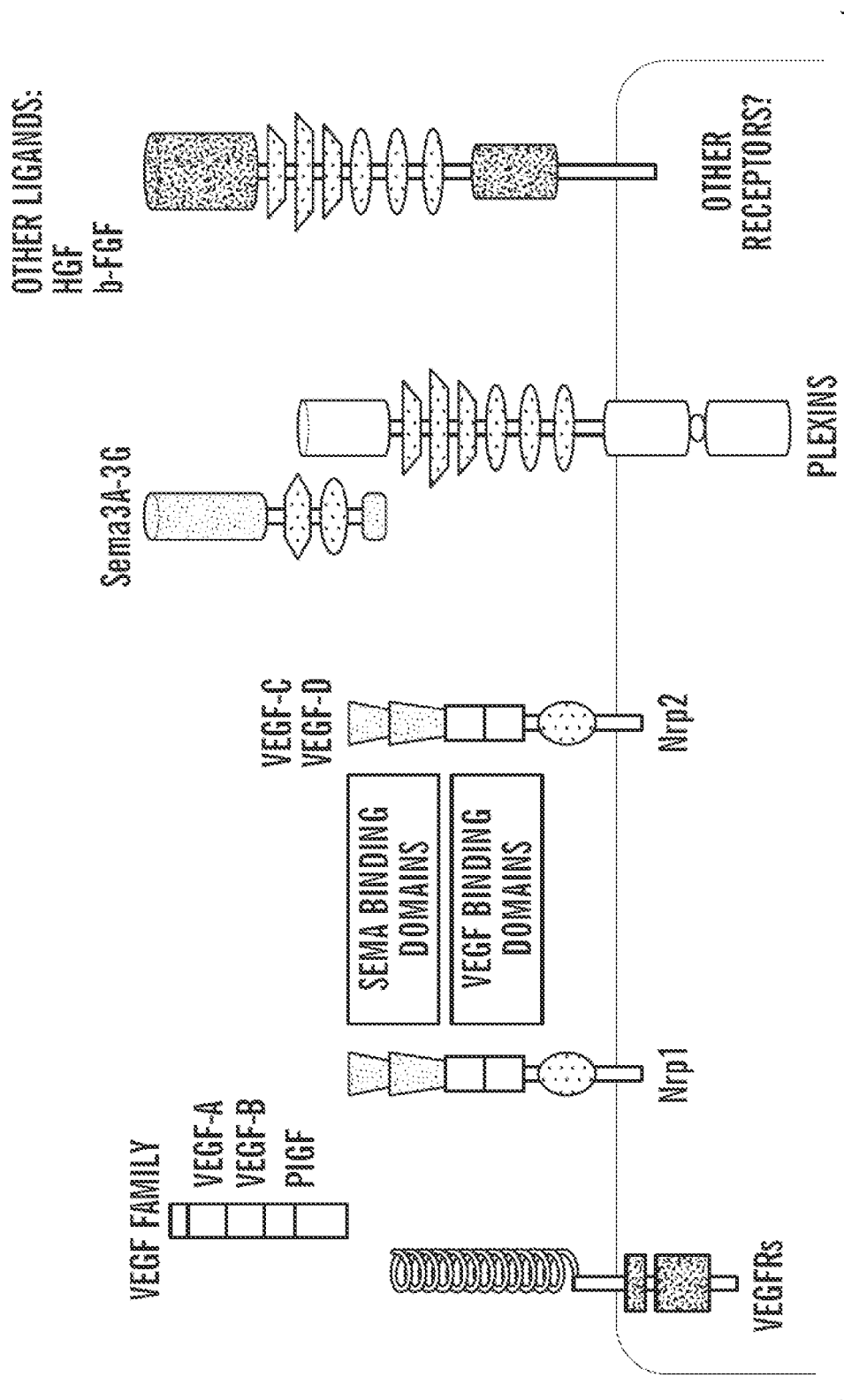
FIG. 1 depicts a schematic illustrating that Neuropilin-1 and Neuropilin-2 have both a Semaphorin binding domain and VEGF binding domain (modified from Bagri et al. 2009).

Described herein are immunomodulatory methods based upon the inventors' discovery that the interaction of Sema3F and NRP-2 functions to suppress the immune system. Accordingly, increasing or enhancing this interaction can suppress an immune response, while inhibiting or decreasing the interaction can upregulate an immune response.

In one aspect, described herein is a method of suppressing the immune system in a subject, the method comprising administering a Sema3F agonist to a subject in need thereof. In some embodiments, suppression of the immune system can comprise treating an inflammatory condition. In some embodiments, suppression of the immune system can comprise suppressing graft rejection (e.g., allograft rejection) or the like. In one aspect, described herein is a method of inhibiting Akt/mTOR signaling in a cell, the method comprising contacting the cell with a Sema3F agonist. In one aspect, described herein is a method of inhibiting Akt/mTOR signaling in a subject, the method comprising administering a Sema3F agonist to a subject in need thereof.

As used herein, "suppression of the immune system" refers to decreasing or inhibiting the immune function of an animal, as measured by any parameter of the various immune functions of the immune system. Non-limiting examples of parameters of immune function can include the magnitude of the antibody response, the response of a B cell, the response of a T cell, the proliferation of T cells, the production of immunomodulatory cytokines, and/or the response to an antigen (e.g. to allogenic or xenogeneic cells). Conversely, "stimulation of the immune system" refers to an increase or activation of the immune function of an animal, as measured by any parameter of the various immune functions of the immune system.

As used herein, "graft rejection" or "transplant rejection" refers to any immunologically mediated hyperacute, acute, or chronic injury to a tissue or organ derived from a source other than the host. The term thus encompasses both cellular and antibody-mediated rejection, as well as rejection of both allografts and xenografts.

In some embodiments, suppressing the immune system can comprise suppressing graft vs. host disease. "Graft-versus-host disease" (GVHD) is a reaction of donated tissue against a patient's own tissue. GVHD is seen most often with hone marrow transplant, but can occur with the transplant of other tissues or cells. GVHD is seen most often in cases where the tissue donor is unrelated to the patient or when the donor is related to the patient but not a perfect match. There are two forms of GVHD: an early form called acute GVHD that occurs soon after the transplant when white cells are on the rise, and a late form called chronic GVHD.

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

An inflammatory condition is any disease state characterized by inflammatory tissues (for example, infiltrates of leukocytes such as lymphocytes, neutrophils, macrophages, eosinophils, mast cells, basophils and dendritic cells) or inflammatory processes which provoke or contribute to the abnormal clinical and histological characteristics of the disease state. Inflammatory conditions include, but are not limited to, inflammatory conditions of the skin, inflammatory conditions of the lung, inflammatory conditions of the joints, inflammatory conditions of the gut, inflammatory conditions of the eye, inflammatory conditions of the endocrine system, inflammatory conditions of the cardiovascular system, inflammatory conditions of the kidneys, inflammatory conditions of the liver, inflammatory conditions of the central nervous system, or sepsis-associated conditions. In some embodiments, the inflammatory condition is associated with wound healing. In some embodiments, the inflammation to be treated according to the methods described herein can be skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation.

In some embodiments, an inflammatory condition can be an autoimmune disease. Non-limiting examples of autoimmune diseases can include: Type 1 diabetes; systemic lupus erythematosus; rheumatoid arthritis; psoriasis; inflammatory bowel disease; Crohn's disease; and autoimmune thyroiditis. Autoimmune disease are well known in the art, for example, see "Automimmue Diseases Research Plan" Autoimmune Disease Coordinating Committee, NIH Publication No. 03-510, December 2002; which is incorporated by reference herein in its entirety.

In some embodiments, a subject in need of treatment for inflammation, wound healing, or pain management can be a subject having, or diagnosed as having temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease. In some embodiments, trauma can include battle-related injuries or tissue damage occurring during a surgery. Smoke-induced lung injury can result from exposure to tobacco smoke, environmental pollutants (e.g. smog or forest fires), or industrial exposure. By way of non-limiting example, inflammatory conditions can be inflammatory conditions of the skin, such as Sweet's syndrome, pyoderma gangrenosum, subcorneal pustular dermatosis, erythema elevatum diutinum, Behcet's disease or acute generalized exanthematous pustulosis, a bullous disorder, psoriasis, a condition resulting in pustular lesions, acne, acne vulgaris, dermatitis (e.g. contact dermatitis, atopic dermatitis, seborrheic dermatitis, eczematous dermatitides, eczema craquelee, photoallergic dermatitis, phototoxicdermatitis, phytophotodermatitis, radiation dermatitis, stasis dermatitis or allergic contact dermatitis), eczema, ulcers and erosions resulting from trauma, burns, ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin, cutaneous atrophy resulting from the topical use of corticosteroids, and inflammation of mucous membranes (e.g.cheilitis, chapped lips, nasal irritation, mucositis and vulvovaginitis).

By way of non-limiting example, inflammatory conditions can be inflammatory conditions of the lung, such as asthma, bronchitis, chronic bronchitis, bronchiolitis, pneumonia, sinusitis, emphysema, adult respiratory distress syndrome, pulmonary inflammation, pulmonary fibrosis, and cystic fibrosis (which may additionally or alternatively involve the gastro-intestinal tract or other tissue(s)). By way of non-limiting example, inflammatory conditions can be inflammatory conditions of the joints, such as rheumatoid arthritis, rheumatoid spondylitis, juvenile rheumatoid arthritis, osteoarthritis, gouty arthritis, infectious arthritis, psoriatic arthritis, and other arthritic conditions. By way of non-limiting example, inflammatory conditions can be inflammatory conditions of the gut or bowel, such as inflammatory bowel disease, Crohn's disease, ulcerative colitis and distal proctitis. By way of non-limiting example, inflammatory conditions can be inflammatory conditions of the eye, such as dry eye syndrome, uveitis (including iritis), conjunctivitis, scleritis, and keratoconjunctivitis sicca. By way of non-limiting example, inflammatory conditions can be inflammatory conditions of the endocrine system, such as autoimmune thyroiditis (Hashimoto's disease), Graves' disease, Type I diabetes, and acute and chronic inflammation of the adrenal cortex. By way of non-limiting example, inflammatory conditions can be inflammatory conditions of the cardiovascular system, such as coronary infarct damage, peripheral vascular disease, myocarditis, vasculitis, revascularization of stenosis, artherosclerosis, and vascular disease associated with Type II diabetes. By way of non-limiting example, inflammatory conditions can be inflammatory conditions of the kidneys, such as glomerulonephritis, interstitial nephritis, lupus nephritis, and nephritis secondary to Wegener's disease, acute renal failure secondary to acute nephritis, post-obstructive syndrome and tubular ischemia. By way of non-limiting example, inflammatory conditions can be inflammatory conditions of the liver, such as hepatitis (arising from viral infection, autoimmune responses, drug treatments, toxins, environmental agents, or as a secondary consequence of a primary disorder), biliary atresia, primary biliary cirrhosis and primary sclerosing cholangitis. By way of non-limiting example, inflammatory conditions can be inflammatory conditions of the central nervous system, such as multiple sclerosis and neurodegenerative diseases such as Alzheimer's disease or dementia associated with HIV infection. By way of non-limiting example, inflammatory conditions can be inflammatory conditions of the central nervous system, such as MS; all types of encephalitis and meningitis; acute disseminated encephalomyelitis; acute transverse myelitis; neuromyelitis optica; focal demyelinating syndromes (e.g., Balo's concentric sclerosis and Marburg variant of MS); progressive multifocal leukoencephalopathy; subacute sclerosing panencephalitis; acute haemorrhagic leucoencephalitis (Hurst's disease); human T-lymphotropic virus type-1 associated myelopathy/tropical spactic paraparesis; Devic's disease; human immunodeficiency virus encephalopathy; human immunodeficiency virus vacuolar myelopathy; peipheral neuropathies; Guillame-Barre Syndrome and other immune mediated neuropathies; and myasthenia gravis. By way of non-limiting example, inflammatory conditions can be sepsis-associated conditions, such as systemic inflammatory response syndrome (SIRS), septic shock or multiple organ dysfunction syndrome (MODS). Further non-limiting examples of inflammatory conditions include, endotoxin shock, periodontal disease, polychondritis; periarticular disorders; pancreatitis; system lupus erythematosus; Sjogren's syndrome; vasculitis sarcoidosis amyloidosis; allergies; anaphylaxis; systemic mastocytosis; pelvic inflammatory disease; multiple sclerosis; multiple sclerosis (MS); celiac disease, Guillain-Barre syndrome, sclerosing cholangitis, autoimmune hepatitis, Raynaud's phenomenon, Goodpasture's syndrome, Wegener's granulomatosis, polymyalgia rheumatica, temporal arteritis/giant cell arteritis, chronic fatigue syndrome CFS), autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, fibromyalgia (FM), autoinflammatory PAPA syndrome, Familial Mediaterranean Fever, polymyalgia rheumatica, polyarteritis nodosa, churg strauss syndrome; fibrosing alveolitis, hypersensitivity pneumonitis, allergic aspergillosis, cryptogenic pulmonary eosinophilia, bronchiolitis obliterans organising pneumonia; urticaria; lupoid hepatitis; familial cold autoinflammatory syndrome, Muckle-Wells syndrome, the neonatal onset multisystem inflammatory disease, graft rejection (including allograft rejection and graft-v-host disease), otitis, chronic obstructive pulmonary disease, sinusitis, chronic prostatitis, reperfusion injury, silicosis, inflammatory myopathies, hypersensitivities and migraines. In some embodiments, an inflammatory condition is associated with an infection, e.g. viral, bacterial, fungal, parasite or prion infections. In some embodiments, an inflammatory condition is associated with an allergic response. In some embodiments, an inflammatory condition is associated with a pollutant (e.g. asbestosis, silicosis, or berylliosis).

In some embodiments, the inflammatory condition can be a local condition, e.g., a rash or allergic reaction.

In some embodiments, the inflammation is associated with a wound. In some embodiments, the technology described herein relates to methods of promoting wound healing. As used herein, "wound" refers broadly to injuries to an organ or tissue of an organism that typically involves division of tissue or rupture of a membrane (e.g., skin), due to external violence, a mechanical agency, or infectious disease. A wound can be an epithelial, endothelial, connective tissue, ocular, or any other kind of wound in which the strength and/or integrity of a tissue has been reduced, e.g. trauma has caused damage to the tissue. The term "wound" encompasses injuries including, but not limited to, lacerations, abrasions, avulsions, cuts, burns, velocity wounds (e.g., gunshot wounds), penetration wounds, puncture wounds, contusions, diabetic wounds, hematomas, tearing wounds, and/or crushing injuries. In one aspect, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics. As used herein, the term "wound healing" refers to a process by which the body of a wounded organism initiates repair of a tissue at the wound site (e.g., skin). The wounds healing process requires, in part, angiogenesis and revascularization of the wounded tissue. Wound healing can be measured by assessing such parameters as contraction, area of the wound, percent closure, percent closure rate, and/or infiltration of blood vessels as known to those of skill in the art. In some embodiments, the particles and compositions described herein can be applied topically to promote wound healing.

As used herein, the term "agonist" refers to any agent that increases the level and/or activity of the target, e.g., of NRP-2. As used herein, the term "agonist" refers to an agent which increases the expression and/or activity of the target by at least 10% or more, e.g. by 10% or more, 50% or more, 100% or more, 200% or more, 500% or more, or 1000% or more. Non-limiting examples of agonists of Sema3F can include Sema3F polypeptides or agonist fragments thereof and nucleic acids encoding a Sema3F polypeptide, e.g. a polypeptide comprising the sequence SEQ ID NO: 1 or SEQ ID NO: 5 or a nucleic acid comprising the sequence of SEQ ID NO: 2 or variants thereof.

As used herein, the term "Sema3F" refers to a member of the class III semaphorins that preferentially binds to NRP-2 as compared to NRP-1. Sequences for Sema3F polypeptides and nucleic acids for a number of species are known in the art, e.g. human Sema3F (NCBI Gene ID: 6405) polypeptide (SEQ ID NO: 1; NCBI Ref Seq: NP_004177) and nucleic acid (SEQ ID NO: 2; NCBI Ref Seq: NM_004186). The level of Sema3F can be assessed in blood, serum and/or plama and the activity of Sema3F can be measured, e.g. by determining the level of binding of Sema3F to NRP-2, a select NRP-2 signaling response, changes in the activity of, and/or the level of an immune responsiveness parameter wherein increased Sema3F activity is evidenced by a reduced immune response and/or alloimmune response (e.g. cytokine responsiveness, priming, or cell migration following transplantation).

In some embodiments, a Sema3F agonist can be a Sema3F polypeptide or functional fragment thereof or a nucleic acid encoding a Sema3F polypeptide or functional fragment thereof. As used herein, "Sema3F polypeptide" can include the human polypeptide (SEQ ID NO: 1, NCBI Ref Seq: NP_004177) the mature human polypeptide (SEQ ID NO: 5); as well as homologs from other species, including but not limited to bovine, dog, cat chicken, murine, rat, porcine, ovine, turkey, horse, fish, baboon and other primates. The terms also refer to fragments or variants of Sema3F that maintain at least 50% of the activity or effect, e.g. suppression of allograft rejection, of the full length Sema3F of SEQ ID NO: 1 or SEQ ID NO: 5, e.g. as measured in an appropriate animal model. Conservative substitution variants that maintain the activity of wildtype Sema3F will include a conservative substitution as defined herein. The identification of amino acids most likely to be tolerant of conservative substitution while maintaining at least 50% of the activity of the wildtype is guided by, for example, sequence alignment with Sema3F homologs or paralogs from other species. Amino acids that are identical between Sema3F homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants, fragments, and/or fusion proteins can be tested for activity, for example, by administering the variant to an appropriate animal model of allograft rejection as described herein. Further discussion of the structure of Sema3F and NRP-2 can be found, e.g. in Klagsbrun M, Eichmann A, *Cytokine Growth Factor Rev,* 2005; which is incorporated by reference herein in its entirety.

In some embodiments, a polypeptide, e.g., a Sema 3F polypeptide, can be a variant of a sequence described herein, e.g. a variant of a Sema3F polypeptide comprising the amino acid sequence of SEQ ID NO: 1 or SEQ ID NO:5. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, e.g., can suppress allograft rejection at least 50% as well as wildtype Sema3F. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or not, has more than 100% of the activity of wildtype Sema3F, e.g. 110%, 125%, 150%, 175%, 200%, 500%, 1000% or more.

One method of identifying amino acid residues which can be substituted is to align, for example, human Sema3F to a Sema3F homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. The variant amino acid or DNA sequence can be at least 90%, at least 95%, at least 96%, at least 97%, at least 98%, at least 99%, or more, identical to a native or reference sequence, e.g. SEQ ID NO: 1 or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm-.nih.gov), with default parameters set.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, a polypeptide, e.g., a Sema 3F polypeptide, administered to a subject can comprise one or more amino acid substitutions or modifications. In some embodiments, the substitutions and/or modifications can prevent or reduce proteolytic degradation and/or prolong half-life of the polypeptide in the subject. In some embodiments, a polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a polypeptide, e.g., a Sema3F polypeptide, as described herein can comprise at least one peptide bond replacement. A Sema3F polypeptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a polypeptide, e.g. a Sema 3F polypeptide, as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (Q), Asp (D), Glu (E), Lys (K), Arg (R), and His (H). In some embodiments, a Sema3F polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a polypeptide, e.g. a Sema3F polypeptide, can be modified, e.g. by addition of a moiety to one or more of the amino acids that together comprise the peptide. In some embodiments, a polypeptide as described herein can comprise one or more moiety molecules, e.g. 1 or more moiety molecules per polypeptide, 2 or more moiety molecules per polypeptide, 5 or more moiety molecules per polypeptide, 10 or more moiety molecules per polypeptide or more moiety molecules per polypeptide. In some embodiments, a polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a polypeptide can be increased by the addition of moieties, e.g. PEG, albumin, or other fusion partners (e.g. Fc fragment of an immunoglobin).

In some embodiments, the Sema3F polypeptide administered to the subject can be a functional fragment of one of the Sema3F amino acid sequences described herein. As used herein, a "functional fragment" is a fragment or segment of a Sema3F polypeptide which can suppress an immune response (e.g. suppress allograft rejection) in a subject according to the assays described below herein. A functional fragment can comprise conservative substitutions of the sequences disclosed herein.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Khudyakov et al. "Artificial DNA: Methods and Applications" CRC Press, 2002; Braman "In Vitro Mutagenesis Protocols" Springer, 2004; and Rapley "The Nucleic Acid Protocols Handbook" Springer 2000; which are herein incorporated by reference in their entireties. In some embodiments, a polypeptide as described herein can be chemically synthesized and mutations can be incorporated as part of the chemical synthesis process.

In some embodiments, a Sema3F polypeptide or functional fragment thereof can be a Sema3F polypeptide that can bind a Sema3F receptor, e.g. NRP-2. In some embodiments, a Sema3F polypeptide or functional fragment thereof can be a Sema3F polypeptide that can bind a domain of NRP-2 selected from the group consisting of the A1; the A2; the B1; and the B2 domain.

As used herein, "NRP-2" or "neuropilin-2" refers to a transmembrane glycoprotein receptor which recognizes class 3 semaphorins and VEGF. NRPs regulate axon growth and angiogensis. NRP2 can be distinguished from NRP1 in that NRP2 has a higher affinity for Sema-3F rather than Sema-3A. The sequences of NRP-2 genes, transcripts, and polypeptides are known in a variety of species, e.g. human NRP-2 mRNA (e.g. SEQ ID NO: 3; NCBI Ref Seq: NM_201266) and polypeptide (e.g. SEQ ID NO: 4; NCBI Ref Seq: NP_957718) sequences (NCBI Gene ID: 8828). NRP-2 comprises the A1 domain (e.g. the amino acids corresponding to positions 28-141 of SEQ ID NO: 4), the A2 domain (e.g. the amino acids corresponding to positions 149-265 of SEQ ID NO: 4), the B1 domain (e.g. the amino acids corresponding to positions 277-427 of SEQ ID NO: 4), and the B2 domain (e.g., the amino acids corresponding to positions 433-592 of SEQ ID NO: 4). Further discussion of NRP-2 structure can be found in the art, e.g., in Appleton et al. The EMBO Journal 2007 26:4901-4912; which is incorporated by reference herein in its entirety. A soluble NRP-2 polypeptide can be a NRP-2 polypeptide corresponding to at least a portion of amino acids 1-862 of SEQ ID NO: 4. In some embodiments, a soluble NRP-2 polypeptide can comprise at least amino acids 1-862 of SEQ ID NO: 4. In some embodiments, a soluble NRP-2 polypeptide can comprise at least 25 contiguous amino acids selected from amino acids 1-862 of SEQ ID NO: 4, e.g., at least 25, at least 50, at least 100, at least 200, at least 250, at least 300, or at least 500 contiguous amino acids selected from amino acids 1-862 of SEQ ID NO: 4. In some embodiments, a soluble NRP-2 polypeptide can comprise at least one NRP-2 domain selected from A1, A2, B1, and/or B2. In one embodiment, soluble NRP-2 polypeptide of use in modulating an immune inflammatory response will bind Sema3F.

The polypeptides of the present invention can be synthesized by using well known methods including recombinant methods and chemical synthesis. Recombinant methods of producing a polypeptide through the introduction of a vector including nucleic acid encoding the polypeptide into a suitable host cell are well known in the art, e.g., as described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a polypeptide (e.g. a Sema3F polypeptide) as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules include DNA, including genomic DNA or cDNA. Other suitable nucleic acid molecules include RNA, including mRNA. The nucleic acid molecule can be naturally occurring, as in genomic DNA, or it may be synthetic, i.e., prepared based upon human action, or may be a combination of the two. The nucleic acid molecule can also have certain modification(s) such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are linked between the 2'-oxygen and the 4'-carbon atoms with a methylene unit as described in U.S. Pat. No. 6,268,490, wherein both patent and patent application are incorporated herein by reference in their entirety.

In some embodiments, a nucleic acid encoding a Sema3F polypeptide as described herein is comprised by a vector. In some of the aspects described herein, a nucleic acid sequence encoding a Sema3F polypeptide as described herein is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain a nucleic acid encoding a Sema3F polypeptide as described herein in place of non-essential viral genes. The vector and/or particle may be utilized for the purpose of transferring nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments the level of, e.g. Sema3F in the subject is increased by at least 20% over the level of Sema3F in the subject (or in a target tissue or system) prior to treatment, e.g. 20% or more, 30% or more, 40% or more, 50% or more, 100% or more, 150% or more, 200% or more, 250% or more, 300% or more, or 350% or more. In some embodiments the level of Sema3F in the subject is increased by at least 100% over the level of Sema3F in the subject prior to treatment. In some embodiments the level of Sema3F in the subject is increased by at least 200% over the level of Sema3F in the subject prior to treatment.

In some embodiments, a Sema3F agonist can be administered intravenously. In some embodiments, a Sema3F agonist can be administered intramuscularly, subcutaneously, or intradermally. In some embodiments, a Sema3F agonist can be administered locally to a site of inflammation.

In one aspect, described herein is a method of increasing an immune response in a subject in need thereof, the method comprising administering one or more of a Sema3F inhibitor or NRP-2 inhibitor or Plexin A1 inhibitor to the subject. In some embodiments, a subject in need of an increase in an immune response can be a subject with a cancer, e.g. with a tumor. In some embodiments, a subject in need of an increase in an immune response can be a subject with an infection, e.g.a baterical or viral infection.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, Sema3F, e.g. its ability to decrease the level and/or activity of Sema3F, can be determined, e.g. by measuring the level of an expression product of Sema3F and/or the activity of Sema3F. Methods for measuring the level of a given mRNA and/or polypeptide are known to one of skill in the art, e.g. RTPCR can be used to determine the level of RNA and Western blotting with an antibody (e.g. an anti-Sema3F antibody, e.g. Cat No. ab39956; Abcam; Cambridge, Mass.) can be used to determine the level of a polypeptide. The activity of, e.g. Sema3F can be determined using methods known in the art and described above herein. In some embodiments, the inhibitor can be an inhibitory nucleic acid; an aptamer; an antibody reagent; an antibody; or a small molecule.

Sema3F can be cleaved by furin-like enzymes. Accordingly, in some embodiments, an inhibitor of Sema3F can be a furin-like polypeptide or a nucleic acid encoding a furin-like polypeptide. Conversely, in some embodiments, an agonist of Sema3F can be a furin-like polypeptide inhibitor, e.g. an inhibitory nucleic acid or small molecule inhibitor. Small molecule furin-like polypeptide inhibitors are known in the art and can include, but are not limited to Furin inhibitor I (e.g. Cat No. 344930; EMD Millipore; Billerica Mass.), Furin inhibitor II (e.g., Cat. No. 344931, EMD Millipore; Billerica Mass.), and proprotein convertase inhibitor (e.g. Cat. No. 537076, EMD Millipore; Billerica Mass.). Further discussion of furin inhibitors can be found, e.g. in Becker et al. J Med Chem 2010 53:1067-1075 and Becker et al. JBC 2012 287:21992-22003; each of which is incorporated by reference herein in its entirety.

As used herein, "furin-like polypeptide" refers to proprotein convertases (PCSKs) having a subtilisin-related catalytic domain and a P-domain carboxy-terminal to the subtilisin domain. PCSKs cleave proproteins to yield active mature proteins. A furin-like polypeptide and/or PCSK can be one or more of PCSK1 (e.g. PC1, PC3, PC1/3; NCBI Gene ID: 5122), PCSK2 (e.g. PC2; NCBI Gene ID: 5126), PCSK3 (e.g. Furin, Pace; NCBI Gene ID: 5045), PCSK4 (e.g. PC4; NCBI Gene ID: 54760), PCSK5 (e.g. PC5, PC6, PC5/6; NCBI Gene ID: 5125), PCSK6 (e.g. PACE4; NCBI Gene ID: 5046), PCSK7 (e.g. PC7, PC8; NCBI Gene ID: 9159), PCSK8 (e.g., Site 1 protease, S1P, SK1; NCBI Gene ID: 8720), PCSK9 (e.g. NARC-1; NCBI Gene ID: 255738). Sequences for furin-like polypeptides and corresponding nucleic acids encoding furin-like polypeptides are known in the art and can be readily obtained for a number of species, e.g. from public databases such as NCBI by searching for the provided gene names.

As used herein, "Plexin A1" refers to a transmembrane protein which can bind in combination with NRP-2 to class III semaphorins, e.g. Sema3F. The sequences for Plexin A1 polypeptides and nucleic acids are known for a number of species, e.g., human Plexin A1 (NCBI Gene ID: 5361) polypeptide (SEQ ID NO: 6; NCBI Ref Seq: NP_115618) and nucleic acid (SEQ ID NO: 7; NCBI Ref Seq: NM_032242).

In some embodiments, a Sema3F inhibitor can be a soluble NRP-2 receptor, e.g. a soluble NRP-2 polypeptide. In some embodiments, a soluble fragment of the NRP-2 receptor comprises at least one domain selected from the group consisting of: the A1, the A2, the B1 or the B2 domain. A soluble NRP-2 receptor fragment will generally lack a transmembrane domain.

In some embodiments, an inhibitor of a polypeptide can be an antibody reagent specific for that polypeptide. In some embodiments, a Sema3F inhibitor can be an anti-Sema3F antibody reagent. In some embodiments, a NRP-2 inhibitor can be an anti-NRP-2 antibody reagent. In some embodiments, the NRP-2 inhibitor binds to the extracellular domain of NRP-2.

As used herein an "antibody" refers to IgG, IgM, IgA, IgD or IgE molecules or antigen-specific antibody fragments thereof (including, but not limited to, a Fab, $F(ab')_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to Sema3F.

In some embodiments, the methods described herein relate to treating a subject having or diagnosed as having, e.g. an inflammatory condition with an agent (e.g. a Sema3F agonist) as described herein. Subjects having, e.g. an inflammatory condition can be identified by a physician using current methods of diagnosis. Symptoms and/or complications of, e.g. inflammatory conditions which characterize these conditions and aid in diagnosis are well known in the art and include but are not limited to, elevated levels of immune response markers, swelling, and/or heat. A family history of an inflammatory condition or exposure to risk factors for an inflammatory condition can also aid in determining if a subject is likely to have the inflammatory condition or in making a diagnosis of a particular inflammatory condition.

The compositions and methods described herein can be administered to a subject having or diagnosed as having, e.g. an inflammatory condition or being in need of immunosuppression (e.g. having received an allograft or transplant). In some embodiments, the methods described herein comprise administering an effective amount a composition described herein, to a subject in order to alleviate a symptom of, e.g. an inflammatory condition. As used herein, "alleviating a symptom" is ameliorating a condition or symptom associated with the condition. As compared with an equivalent untreated control, such reduction is by at least 10% as measured by any standard technique. A variety of means for administering the compositions described herein to subjects are known to those of skill in the art. Such methods can include, but are not limited to parenteral, intravenous, intramuscular, subcutaneous, transdermal, airway (aerosol), pulmonary, cutaneous, topical, or injection administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount that is sufficient to provide a particular effect when administered to a typical subject. An effective amount as used herein, in various contexts, would also include an amount sufficient to delay the development of a symptom of the disease, alter the course of a disease symptom (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition, which achieves a half-maximal inhibition of symptoms) as determined in cell culture, or in an appropriate animal model. Levels in plasma can be measured, for example, by immunoassay or chromatography. The effects of any particular dosage can be monitored by a suitable bioassay, e.g., assay for immune responsiveness, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. Polypeptides, such as Sema3F, will generally be formulated for parenteral administration and can be combined with any carrier suited for parenteral routes of administration. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration to a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat.

Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like. In some embodiments, the additional anti-inflammatory agent can be a steroid (e.g., a corticosteroid or glucocorticoid); a calcineurin inhibitor (e.g. cyclosporine, tacrolimus, pimecrolimus, or FK506); an mTOR inhibitor (e.g., everolimus, temsirolimus, rapamycin, deforolimus, TOP216, OSI-027, TAFA93, nab-rapamycin, tacrolimus, biolimus, CI-779, ABT-578, AP-23675, BEZ-235, QLT-0447, ABI-009, BC-210, salirasib, AP-23841, AP-23573, KU-0059475, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin; 16-pent-2-ynyloxy-32(S)-dihydrorapamycin; socalledrapalogs; AP23464; PI-103, PP242, PP30, Torin1; and derivatives or pharmaceutically acceptable salts thereof as well as and compounds described in, e.g. U.S. Patent Publications 2011/0178070; 2011/0021515; 2007/0112005; 2011/0054013; International Patent Publications WO98/02441; WO01/14387; WO99/15530; WO07/135411; WO03/64383; WO96/41807; WO95/16691; WO94/09010; European Patent No. EP1880723; and U.S. Pat. Nos. 8,163,775; 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; which are incorporated by reference herein in their entireties.); rapamycin (sirolimus) or an analogue therof (e.g. everolimus, temsirolimus, ridaforolimus, deforolimus); or an anti-prolferative agent (e.g. mycophenoloate moefitil, azathioprine). In some embodiments, the mTOR inhibitor can be rapamycin or an analogue thereof, e.g. everolimus, temsirolimus, ridaforolimus, or deforolimus. Anti-proliferative agents can include, by way of non-limiting example, alkylating agents (e.g. cyclophosphamide, platinum compounds, and nitrosoureass), antimetabolites (e.g. methotrexate, azathioprine, mercaptopurine, fluorouracil, etc), and cytotoxic antibiotics (e.g., dactinomycin, anthracyclines, mitomycin C, bleomycin, and mithramycin).

In certain embodiments, an effective dose of a composition as described herein can be administered to a patient once. In certain embodiments, an effective dose of a composition can be administered to a patient repeatedly. For systemic administration, subjects can be administered a therapeutic amount of a composition, such as, e.g. 1 µg/kg, 10 µg/kg, 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. a marker of an immune response by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition, according to the methods described herein depend upon, for example, the form of the active ingredient, its potency, and the extent to which symptoms, markers, or indicators of a condition described herein are desired to be reduced, for example the percentage reduction desired for an immune response or the extent to which, for example, an immune response is desired to be induced. The dosage should not be so large as to cause adverse side effects.

Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. graft rejection. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing or slowing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of allograft rejection in mice. When using an experimental animal model, efficacy of treatment is evidenced when a statistically significant change in a marker is observed, e.g. the level and/or proliferation of activated T or B cells.

In vitro and animal model assays are provided herein which allow the assessment of a given dose of a composition described herein, e.g. an agonist of Sema3F. By way of non-limiting example, the effects and dose response of a composition can be assessed by treating CD4+ T cells with mitogen (anti-CD3) in the presence and absence of the composition and measuring proliferation and/or the production of cytokines including, but not limited to, IL-2, IL-4 IFN-gamma, IL-17, IL-10, IL-15 and others, where Neuropilin-2 activity is indicated by a lower level of proliferation and/or decreased production of select and/or programs of cytokines.

The efficacy of a given dosage combination can also be assessed in an animal model, e.g. a mouse model of allograft rejection, colitis, or skin inflammation/delayed type hypersensitivity (DTH). For example, C57BL/6 mice can be the recipients of a cardiac or skin allograft from BALB/c mice. Rejection and/or survival can be monitored, e.g. over at least 1-3 weeks. In DTH, skin swelling can be monitored over 1-7 days. As demonstrated herein, treatment of allograft recipients with Sema3F inhibits allograft rejection. Inflammatory response and DTH responses are reduced following treatment with Sema3F. Also, knockout of Neuropilin-2 in recipients of transplants results in accelerated rejection.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of, e.g., allograft rejection. A subject can be male or female.

A subject can be one who has been previously diagnosed with or identified as suffering from or having a condition in need of treatment (e.g. a subject undergoing an allograft or having an autoimmune disease) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of NRP-2, Sema3F, and/or PlexinA1. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—$N(CH_3)$—O—$CH_2$— [known as a methylene (methylimino) or MMI backbone], —$CH_2$—O—$N(CH_3)$—$CH_2$—, —$CH_2$—$N(CH_3)$—$N(CH_3)$—$CH_2$— and —$N(CH_3)$—$CH_2$—$CH_2$— [wherein the native phosphodiester backbone is represented as —O—P—O—$CH_2$— ] of the above-referenced U.S. Pat. No. 5,489,677, and the amide backbones of the above-referenced U.S. Pat. No. 5,602,240.

In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)—NH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA as described herein involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "treat" "treatment" "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice. See, e.g., Freshney, CULTURE ANIMAL CELLS: MANUAL BASIC TECH. (3rd ed., 1994). As used herein, the term "cancer" refers to an uncontrolled growth of cells that interferes with the normal functioning of the bodily organs and systems. A subject who has a cancer or a tumor is a subject having objectively measurable cancer cells present in the subject's body. Included in this definition are benign and malignant cancers, as well as dormant tumors or micrometastases. Cancers that migrate from their original location and seed vital organs can eventually lead to the death of the subject through the functional deterioration of the affected organs.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of suppressing allograft rejection, the method comprising administering a Sema3F agonist to an allograft recipient, whereby immune rejection of the allograft is suppressed.
2. A method of suppressing the immune system in a subject, the method comprising administering a Sema3F agonist to a subject in need thereof
3. A method of treating an inflammatory condition in a subject in need of thereof, the method comprising administering a Sema3F agonist to the subject.
4. The method of paragraph 3, wherein the inflammatory condition is an autoimmune disease.
5. The method of paragraph 4, wherein the autoimmune disease is selected from the group consisting of:
   Type 1 diabetes; systemic lupus erythematosus; rheumatoid arthritis; psoriasis; inflammatory bowel disease; Crohn's disease; and autoimmune thyroiditis.
6. The method of paragraph 3, wherein the inflammatory condition is a local condition.
7. The method of paragraph 6, wherein the local inflammatory condition is selected from the group consisting of:
   a rash and an allergic reaction.
8. A method of treating cancer, the method comprising administering a Sema3F agonist to a subject in need of treatment thereof
9. A method of reducing angiogenesis, the method comprising administering a Sema3F agonist to a subject in need of treatment thereof
10. The method of any of paragraphs 1-9, wherein the Sema3F agonist is a Sema3F polypeptide or a nucleic acid encoding a Sema3F polypeptide.
11. The method of any of paragraphs 1-10, wherein the Sema3F polypeptide comprises the sequence of SEQ ID NO: 5.
12. The method of paragraph 10, wherein the Sema3F polypeptide can bind a Sema3F receptor.
13. The method of any of paragraphs 1-12, wherein the Sema3F polypeptide can bind a domain of NRP-2 selected from the group consisting of:
   the A1; the A2; the B1; and the B2 domain.
14. The method of any of paragraphs 1-13, wherein the Sema3F agonist is a furin-like inhibitor.
15. The method of any of paragraphs 1-14, wherein the Sema3F agonist is administered intravenously.
16. The method of any of paragraphs 1-14, wherein the Sema3F agonist is administered intramuscularly, subcutaneously, or intradermally.
17. The method of any of paragraphs 1-16, wherein the Sema3F agonist is administered locally to a site of inflammation.
18. The method of any of paragraphs 1-17, further comprising administering an additional anti-inflammatory agent.
19. The method of paragraph 18, wherein the additional anti-inflammatory agent is selected from the group consisting of:
   a steroid; a calcineurin inhibitor; mTOR inhibitor or an analogue thereof and an anti-proliferative agent.
20. A method of increasing an immune response in a subject in need thereof, the method comprising administering one or more of a Sema3F inhibitor or NRP-2 inhibitor or Plexin A1 inhibitor to the subject.

21. The method of paragraph 20, wherein the Sema3F inhibitor is an anti-Sema3F antibody reagent.
22. The method of paragraph 20, wherein the NRP-2 inhibitor is an anti-NRP-2 antibody reagent.
23. The method of paragraph 20, wherein the Sema3F inhibitor is a soluble NRP-2 receptor.
24. The method of paragraph 23, wherein the Sema3F inhibitor is a soluble fragment of the NRP-2 receptor comprising at least one domain selected from the group consisting of:
the A1, the A2, the B1 or the B2 domain.
25. The method of paragraph 20, wherein the Sema3F inhibitor is a furin-like polypeptide or a nucleic acid encoding a furin-like polypeptide.
26. The use of a Sema3F agonist, to suppress allograft rejection in an allograft recipient.
27. The use of a Sema3F agonist, the use comprising administering a Sema3F agonist to a subject in need of immune system suppression.
28. The use of a Sema3F agonist, for the treatment of an inflammatory condidtion in a subject in need thereof
29. The use of paragraph 28, wherein the inflammatory condition is an autoimmune disease.
30. The use of paragraph 29, wherein the autoimmune disease is selected from the group consisting of:
Type 1 diabetes; systemic lupus erythematosus; rheumatoid arthritis; psoriasis; inflammatory bowel disease; Crohn's disease; and autoimmune thyroiditis.
31. The use of paragraph 28, wherein the inflammatory condition is a local condition.
32. The use of paragraph 31, wherein the local inflammatory condition is selected from the group consisting of:
a rash and an allergic reaction.
33. The use of a Sema3F agonist, for the treatment of cancer.
34. The use of a Sema3F agonist, for the suppression of angiogenesis in a subject in need thereof
35. The use of any of paragraphs 26-34, wherein the Sema3F agonist is a Sema3F polypeptide or a nucleic acid encoding a Sema3F polypeptide.
36. The use of any of paragraphs 26-35, wherein the Sema3F polypeptide comprises the sequence of SEQ ID NO: 5.
37. The use of paragraph 35, wherein the Sema3F polypeptide can bind a Sema3F receptor.
38. The use of any of paragraphs 35-37, wherein the Sema3F polypeptide can bind a domain of NRP-2 selected from the group consisting of:
the A1; the A2; the B1; and the B2 domain.
39. The use of any of paragraphs 26-38, wherein the Sema3F agonist is a furin-like inhibitor.
40. The use of any of paragraphs 26-39, wherein the Sema3F agonist is administered intravenously.
41. The use of any of paragraphs 26-39, wherein the Sema3F agonist is administered intramuscularly, subcutaneously, or intradermally.
42. The use of any of paragraphs 26-41, wherein the Sema3F agonist is administered locally to a site of inflammation.
43. The use of any of paragraphs 26-42, further comprising administering an additional anti-inflammatory agent.
44. The use of paragraph 43, wherein the additional anti-inflammatory agent is selected from the group consisting of:
a steroid; a calcineurin inhibitor; mTOR inhibitor or an analogue thereof; and an anti-proliferative agent.
45. The use of one or more of a Sema3F inhibitor or NRP-2 inhibitor or Plexin A1 inhibitor to promote an immune response in a subject in need thereof
46. The use of paragraph 45, wherein the Sema3F inhibitor is an anti-Sema3F antibody reagent.
47. The use of paragraph 45, wherein the NRP-2 inhibitor is an anti-NRP-2 antibody reagent.
48. The use of paragraph 45, wherein the Sema3F inhibitor is a soluble NRP-2 receptor.
49. The use of paragraph 46, wherein the Sema3F inhibitor is a soluble fragment of the NRP-2 receptor comprising at least one domain selected from the group consisting of:
the A1, the A2, the B1 or the B2 domain.
50. The use of paragraph 45, wherein the Sema3F inhibitor is a furin-like polypeptide or a nucleic acid encoding a furin-like polypeptide.

EXAMPLES

Example 1: A Novel Immunomodulatory Function for Semaphorin3f and Neuropilin-2 in Allograft Rejection The class 3 family of semaphorins (Sema3A-G) bind to Plexin and Neuropilin family molecules and elicit regulatory signals that result in anti-migration and anti-proliferation. It is demonstrated herein that Sema3F modulates PI-3K-Akt and MAPK signaling via binding to neuropilin-2 (NRP-2), indicating that this ligand-receptor interaction can inhibit T cell activation responses. However, the role of Sema3F and NRP-2 in immunity is previously unexplored.

Described herein is the treatment of C57BL/6 recipients of fully mismatched BALB/c cardiac allografts with Sema3F. Sema3F is demonstrated herein as potent to inhibit rejection; mean graft survival was >22 days (when administered via adenovirus, n=4 mice, P<0.000) and 23.4 days (when administered via i.p. injection, n=16 mice) vs. untreated controls (Mean survival 6.5 days, n=8, P<0.000). Co-treatment of Sema3F treated recipients (i.p. injection model) with a blocking anti-Sema3F antibody (on days 0, 2, 4 and 6) reduced graft survival to control (mean survival 7.5 days, n=4).

By qPCR, FACS and Western blot, it was demonstrated that the Sema3F ligand NRP-2 is expressed on T cell subsets at baseline, and its expression is markedly induced on CD4+ effectors and regulatory cells following 6 hr mitogen-activation (anti-CD3). CD4+ T cells were also found to express Plexin A1-4 family molecules (by qPCR), further indicating that Sema3F may elicit its regulatory signaling via NRP-2 and Plexin. To determine function, we generated NRP-2+/− (Hets) and NRP-2−/− (ko) mice; in vitro, CD4+ T cells derived from these mice were hyperproliferative (~3 fold increase) and produce increased IL-2 and IFNgamma vs. WT cells in response to mitogen (anti-CD3). Hyperactivation was most notable in naïve NRP-2ko CD4+CD25neg T cells vs. CD4+CD25+ subsets.

Finally, NRP-2ko mice were used as recipients of fully mismatched BALB/c and minor mismatched B6.C-H-2bm12 donor cardiac transplants. NRP-2ko mice rejected BM12 hearts (mean graft survival 32 days, n=5), vs. WT mice (mean graft survival >54 days, n=11, P<0.00). In contrast, NRP-2ko mice rejected fully mismatched allografts at the same tempo as WT grafts. Additionally, Sema3F can inhibit rejection in NRP-2KO mice, indicating that it can have immunomodulatory effects that are independent of NRP-2. Collectively, these findings for the first time define Sema3F and NRP-2 as novel immunomodulatory proteins. These findings also indicate that Sema3F-NRP-2 interactions are highly significant for the modulation of allogeneic responses.

Example 2: Novel Effects of Semaphorin3F on the Regulation of Intracellular PI-3K-Akt and MAPK Signaling Class three semaphorins bind neuropilin (NRP) and plexin family molecules and serve as guidance molecules that elicit signals resulting in anti-migration and cytoskeleton collapse. As described herein, semaphorin 3F (SEMA3F) is potent to inhibit allograft rejection in a fully mismatched cardiac allograft model. In addition, it is described herein that NRP2 knockout mice have hyperactive T cells and accelerated rejection, suggesting that Sema3F mediates immunomodulation via interactions with NRP2. Additionally, NRP2 is demonstrated herein to be expressed on both effector and regulatory CD4+ T cells, suggesting that it is a novel protein that targets T cell activation responses. However, the molecular mechanisms of SEMA3F-induced regulation of the immune response are not known.

Two cell lines (U87MG and U343) expressing high levels of NRP2 were used to screen Sema3F-regulated intracellular signaling pathways using phospho-kinase antibody arrays. It was observed that a most potent effect of Sema3F (e.g., 640 ng/ml) is to inhibit the activity of pAkt (T308 and S473) pmTOR and pS6K and pERK, which was confirmed in a time course by Western blot analysis.

SEMA3F binds NRP2 and forms complexes with Plexin A1. Knockdown of either NRP2 or Plexin A1 in U87MG cells using siRNAs inhibited SEMA3F-induced decreases in p-Akt (S473) and p-S6K. These observations indicate that the inhibitory effect of Sema3F is mediated through binding of SEMA3F to NRP2/Plexin A1 at the cell surface.

Using immunoprecipitation, it was also observed that SEMA3F disrupted the association of both raptor and rictor with mTOR. Furthermore, when the cells were treated with rapamycin (10 ng/ml) for 30 mins to target mTORC1, Sema3F is potent to inhibit pAkt (S473)/mTORC2. Also, following transfection with 2DAkt to constitutively activate mTORC1, again it is found that Sema3F inhibits pAkt, confirming that the primary effect of Sema3F-NRP-2 interactions is to target mTORC2/Akt-induced responses.

Figure 21:
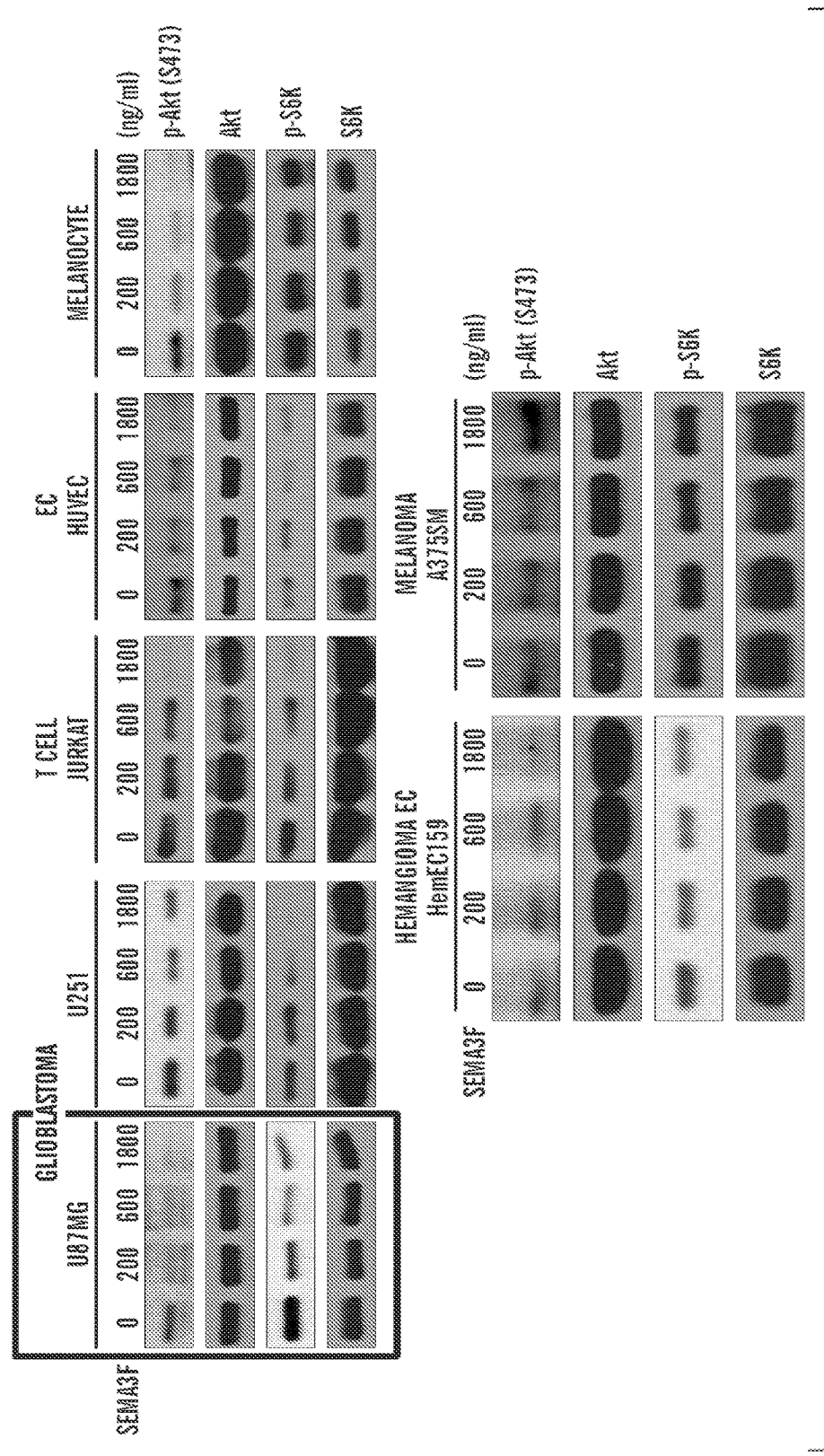
FIG. 21 demonstrates that SEMA3F inhibits Akt/mTOR signaling in multiple cell types. The results of Western blots are depicted, demonstrating the effect of increasing concentrations of Sema3F on Akt/mTOR signaling in the indicated cell types.

Finally, Sema3F-induced responses were evaluated in a human Jurkat T cell line that expresses NRP-2, and it was further confirmed that it elicits a marked regulatory signaling response, including, e.g., the inhibition of pAKT activity. Sema3F inhibits Akt/mTOR signaling in multiple cell types (FIG. 21). Overall, these findings for the first time identify SEMA3F as a novel secreted protein that functions in physiological inflammation resolution via the modulation of intracellular signaling. The findings described herein indicate that Sema3F has broad application as a potent anti-inflammatory therapeutic.

Example 3: Expression and Function of Neuropilin-2, a Semaphorin Receptor, on CD4+ T Cell Subsets The neuropilins NRP-1 and NRP-2 bind semaphorin class 3 family molecules including SEMA3A and SEMA3F respectively, as well as Vascular Endothelial Growth Factor. The binding of SEMA3A to NRP-1 and SEMA3F to NRP-2 elicits inhibitory signals in endothelial cells. NRP-1 is expressed on T cells, and it is prominent on the CD25+ FoxP3+ T regulatory cell subset. In these studies, using qPCR, Western Blot analysis and FACS the expression of NRP-2 on unactivated and mitogen-activated human CD4+ T cells (anti-CD3/anti-CD28, each at 1mg/ml) was evaluated. Consistently, it was found that NRP-2 expression is minimal on unactivated cells, but is markedly induced (3 to 5 fold, p=0.06, n=3) following activation. Patterns of expression of NRP-2 on murine leukocytes were also profiled and expression on splenocytes as well as enriched CD4+ T cells was found. Although NRP-1 is the dominant receptor on CD25hi Tregs, it was found that NRP-2 is present on both CD4+CD25+ T regulatory and CD4+CD25− T effector subsets. To define function, CD4+ T cells were sorted from wild type C57/BL6 mice and activation responses assessed following culture with increasing concentrations of anti-CD3 (0.001-1 mg/ml). Taken together, these studies for the first time identify NRP-2 expression on CD4+ T lymphocytes, and indicate that SEMA3F-NRP-2 interactions function in T cell activation responses. These findings set the stage for a new understanding of how class 3 semaphorins may act as novel regulatory cyokines in cell-mediated immunity and allograft rejection.

Figure 7:
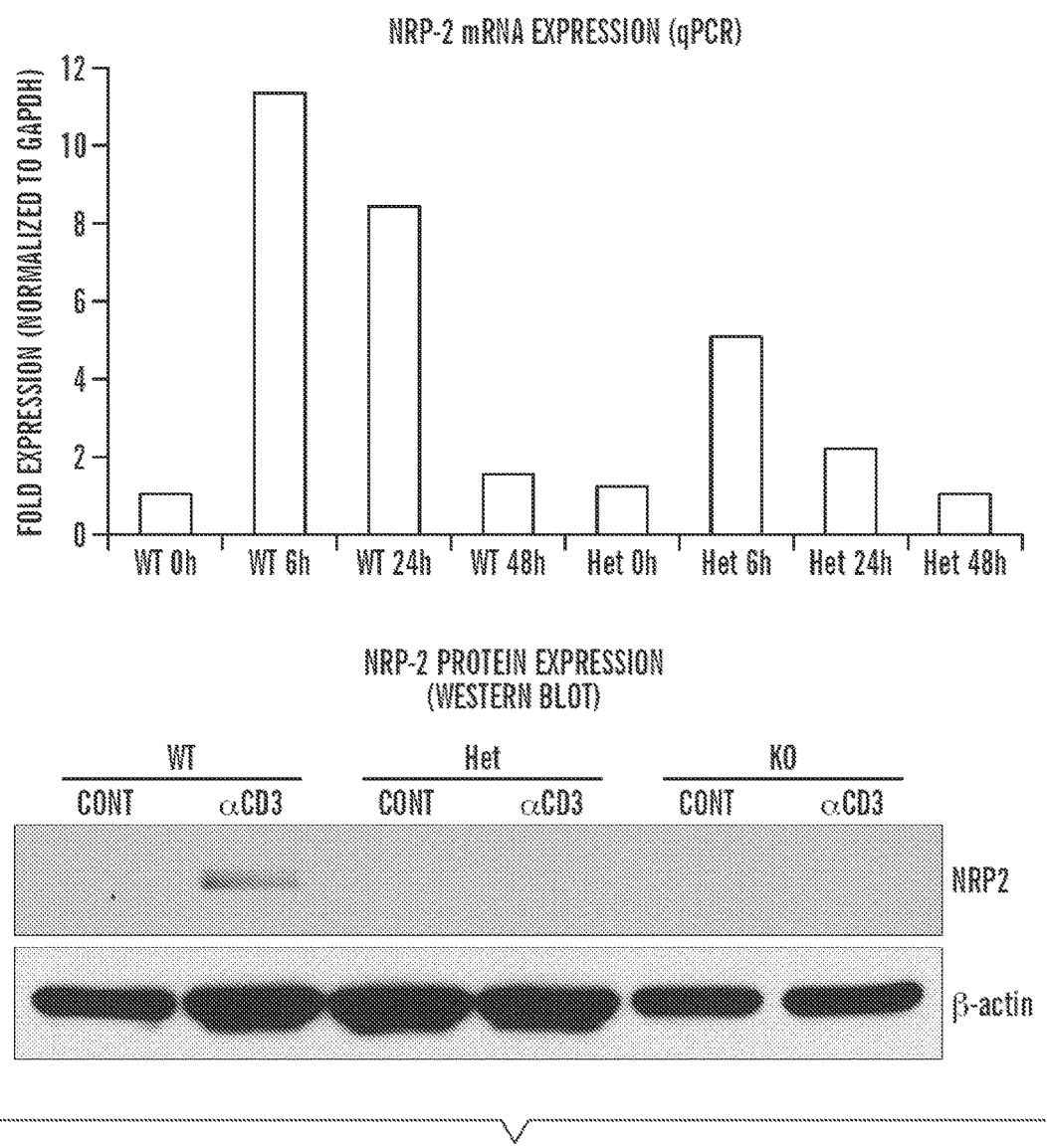
FIG. 7 depicts a graph of the Sema3F receptor Neuropilin-2 (mRNA (top) and protein (bottom)) expression in murine CD4$^+$ T cells. CD4$^+$ T cells were isolated from spleen, were incubated with plate-bound anti-CD3 (1 mcg/ml) for 6 h-48 h. RNA was isolated and qPCR was performed. Expression by Western Blot analysis is shown in the bottom panel.
Figure 8:
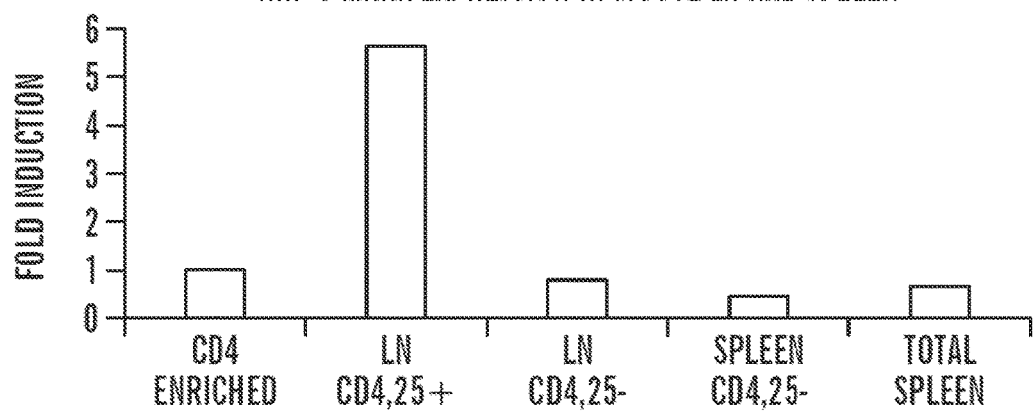
FIG. 8 depicts graphs of Neuropilin-1 and Neuropilin-2 mRNA expression in murine CD4$^+$ T cells. Naïve C57BL6 CD4$^+$ T cells were isolated from lymph nodes and spleen. CD4$^+$ T cell subsets were FACS-sorted into CD25$^{high}$ and CD25$^{low}$ subsets. RNA from CD4$^+$ subsets was isolated and expression levels were determined by qPCR.
Figure 8:
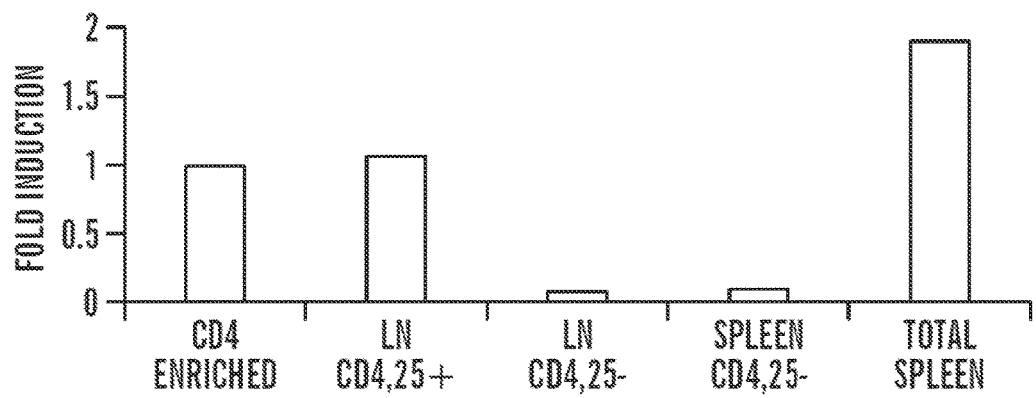

Mitogen-activation increases the expression of both NRP-1 and NRP-2 in human T cells (FIG. 7). NRP-1 is expressed in $CD4^+$ $CD25^{high}$ T cells, whereas NRP-2 is generally expressed in enriched populations of CD4+ T cells (FIG. 8).

Following 7 days of priming with allogeneic or syngeneic splenocytes, recipient spleen cells were stained with CD4 and NRP-2 (monoclonal rabbit anti-mouse NRP-2 from Cell Signalling), followed by a FITC-conjugated donkey anti-rabbit secondary Ab) and subjected to FACS. Quantification following FACS illustrated that allogeneic primed spleen CD4 displayed an increased expression of NRP-2, when compared to syngeneic priming or untreated spleen cells (data not shown).

Taken together these studies identify NRP-2 expression on $CD4^+$ T lymphocytes, and indicate that SEMA3F-NRP-2 interactions function in T cell activation responses.

REFERENCES

Bagri A et al. Clin Cancer Res 2009; 15:1860-1864.

Example 4

It is demonstrated herein that Neuropilin-2 is expressed on human T cells and T cell lines (Jurkat T cells) and the binding of Sema3F results in an activation response. Neuropilin is further demonstrated to be expressed on murine T cells.

The Treatment of Allograft Recipients with Sema3F Adenovirus Prolongs Survival.

The injection i.p of cells overexpressing Semaphorin3F into mice recipients of cardiac transplants is associated with a prolongation of allograft survival, and a delay in the acute rejection response (Rejection in untreated controls day 6-8, rejection following transferred cells day 21-28). Control cells that do not express Sema3F do not delay allograft rejection. Also Transferred cells fail to prolong survival and delay rejection in mice that also received a blocking anti-sema3F antibody (to block the effects of sema3F). In preliminary studies this effect of transferred cells does not occur in mice deficient in NRP-2.

Cells from mice lacking NRP-2 (Heterzygous and NRP-2 KO mice) are hyperproliferative and produce more cytokines than wild type cells following activation with mitogen. Mice lacking NRP-2 (Heterozygous and NRP-2 KO mice) have an accelerated allograft rejection response.

It is specifically contemplated herein that:
a. Semaphorin 3F or related molecules can be utilized as anti-inflammatory or immunomodulator agents in many inflammatory disease states.
b. Semaphorin 3F and NRP-2 agonists can be utilized in treating and/or preventing allograft rejection. Augmenting these interactions can serve as an immunosuppressant.
c. The use of targeted anti-semaphorin or anti-NRP-2 (A domain molecules) as agents to enhance immune responses.
d. Different mechanisms of antagonism, using NRP-A domain, B domain or A+B domain peptide soluble proteins in immunomodulation Example 5

Figure 2:
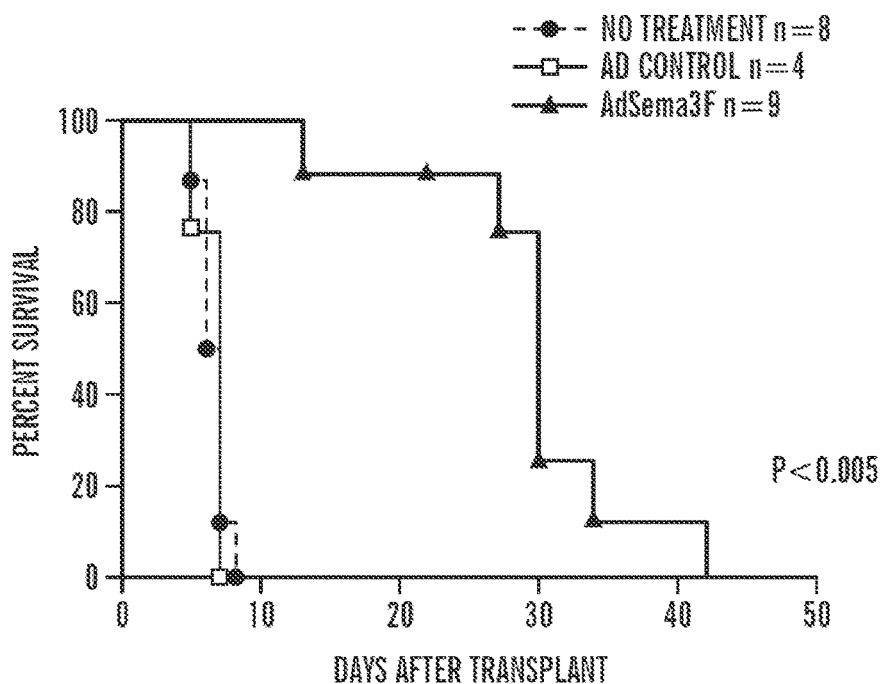
FIG. 2 depicts graft survival curves. Cardiac allografts (Balb/c) were transplanted into fully MHC mismatched recipients (C57BL/6). Unmanipulated recipients reject these allografts within 7-8 days. IV injection of adenovirus encoding Sema3F results in prolonged allograft survival indicating that this agent has potent effects to inhibit the immune response.
Figure 3:
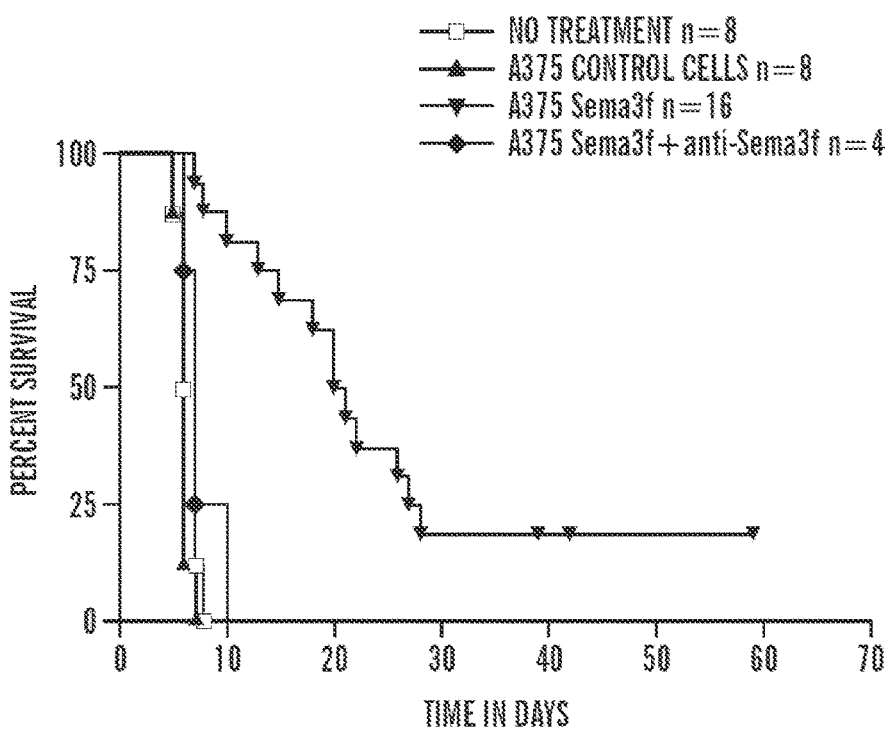
FIG. 3 depicts graft survival curves. Cardiac allografts (Balb/c) were transplanted into fully MHC mismatched recipients (C57BL/6). Unmanipulated recipients reject these allografts within 7-8 days. Injection of Sema3F-expressing cells intraperitoneally to increase systemic levels of Sema3F results in prolonged allograft survival indicating that this agent has potent effects to inhibit the immune response. Injection of Sema3F-expressing cells in combination with a blocking anti-Sema3F antibody does not result in prolonged graft survival

Semaphorin 3F Acts as an Immunosuppressant In Vivo to Inhibit Acute Allograft Rejection Balb/C donor hearts were transplanted into C56BL6 mice. Control mice experienced rejection on day 7-8. IV injection of Adenovirus encoding Sema3F into mice following cardiac transplantation prolongs survival up to day 40 (FIG. 2).

Figure 4:
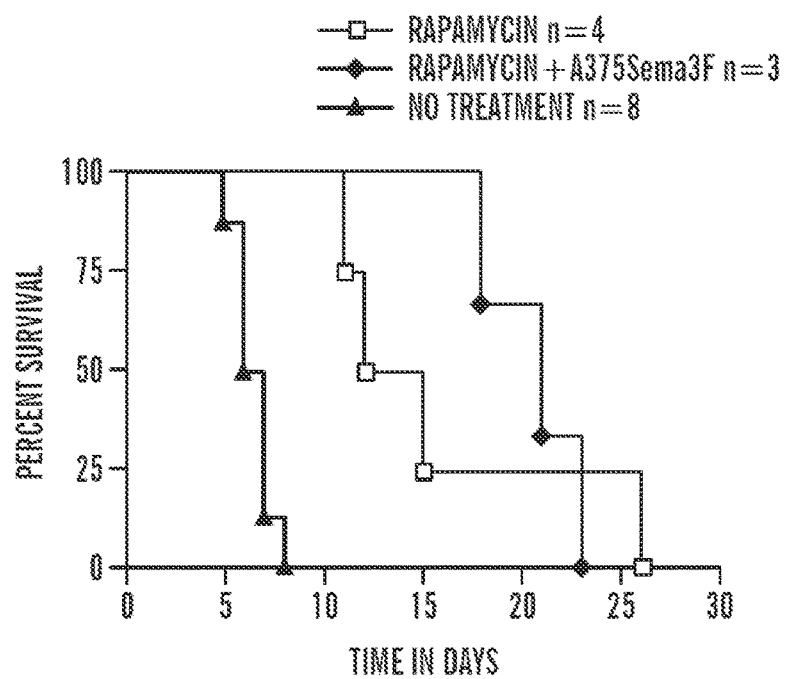
FIG. 4 depicts graft survival curves of C56BL6 recipient mice after transplantation with Balb/C donor hearts. Injection of Sema3F-expressing cells intraperitoneally to increase systemic levels of Sema3F results in prolonged allograft survival Rapamycin (0.2 mg/kg) was administered on day 0 and day 2 to initiate a tolerogenic stimulus. Rapamycin failed to further increase survival in combination with Sema3F-expressing cells.

Rapamycin at 0.2 mg/kg was administered on day 0-2 and Sema3F was administered. No additive graft prolongation effect was observed in this limited model (no sig. prolongation of survival) (FIG. 4).

Figure 9:
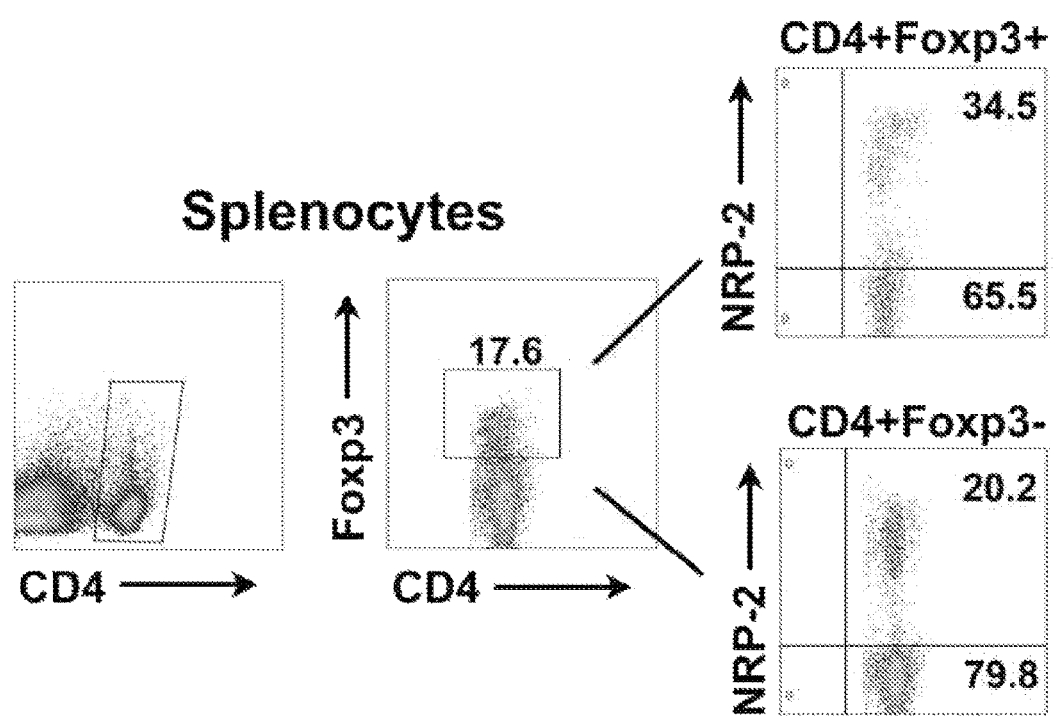
FIG. 9 depicts the results of FACS analysis of CD4+ T cells, both Foxp3$^{pos}$ and Foxp3$^{neg}$ cells. NRP-2 expression was detected using a rabbit anti-NRP-2 Ab (Bioss).

The expression of NRP-2 on T cell subsets was at the mRNA level (FIGS. 7 and 22), protein level by Western Blot (FIGS. 7 and 22) and by FACS (FIG. 9). As illustrated, notable expression of NRP-2 was observed on activated CD4+ T cells, both Foxp3$^{pos}$ and Foxp3$^{neg}$ cells.

CD4+ T cells were sorted into CD25$^{neg}$ T effector subsets from WT, NRP-2+/−(Hets) and NRP-2−/− (KO) mice on a C57BL/6 background. Mitogen-induced proliferation and cytokine production (ELISPOT) was assessed. Markedly enhanced activation responses were observed in whole populations of CD4+ T cells as well as CD25$^{neg}$ subsets derived from NRP-2 Hets and NRP-2 KO mice. This marked hyperactivation response confirms the hypothesis that NRP-2 provides a novel regulatory signal to CD4+ T cells. Sorted populations of CD4+CD25$^{neg}$ T effector subsets were also cultured with increasing concentrations of mitogen (anti-CD3) in the presence of anti-CD28. CD4+ T cells proliferate maximally in response to costimulatory signals, however, NRP-2 KO cells remain hyperactive and produce significantly more IFNg and IL-2 than CD4+ T cells derived from WT mice. This observation further demonstrates that NRP-2 is functional in CD4+ T cells, and likely elicits regulatory signals.

Chronic Rejection

Figure 5:
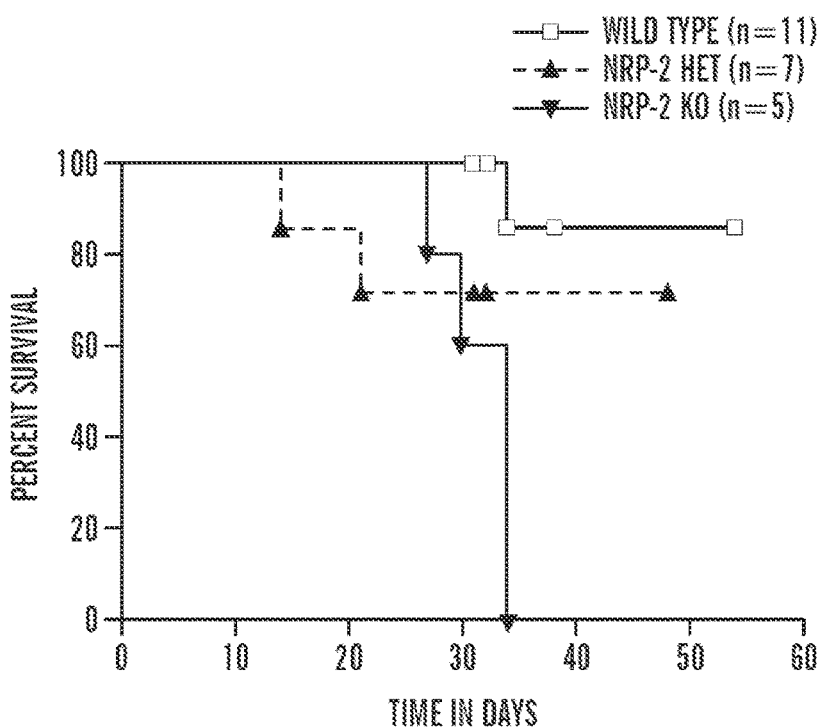
FIG. 5 depicts graft survival curves. Cardiac allografts (B6.C-H2$^{bm12}$(BM12)) were transplanted into minor MHC mismatched recipients wild type (WT C57BL/6), NRP-2+/− (Het on BL6) or NRP-2−/− (Knockout mice on BL6). While cardiac allografts survive long term in WT recipients, KO mice mount an accelerated rejection response.

Minor MHC mismatched B6.C-H2$^{bm12}$ (BM12) allografts were transplanted into C57BL/6 (wild type/WT), NRP-2+/− (Het on BL6) or NRP-2−/− (KO on BL6) mice. As expected, allografts in WT recipients survive long term but develop chronic rejection after ~30 days post transplantation; marked evidence of disease is present by day 45 (FIG. 5). Long-term survival in this model is reported to be associated with the expansion of T regulatory cells by day 21 post transplantation, that limit the expansion of T effectors (104). Survival is reduced in NRP-2+/− Het recipients and significantly reduced in NRP-2−/− KO recipients (P<0.05). These observations are consistent with the findings that NRP-2 has a regulatory function in CD4+ T cells.

Figure 10:
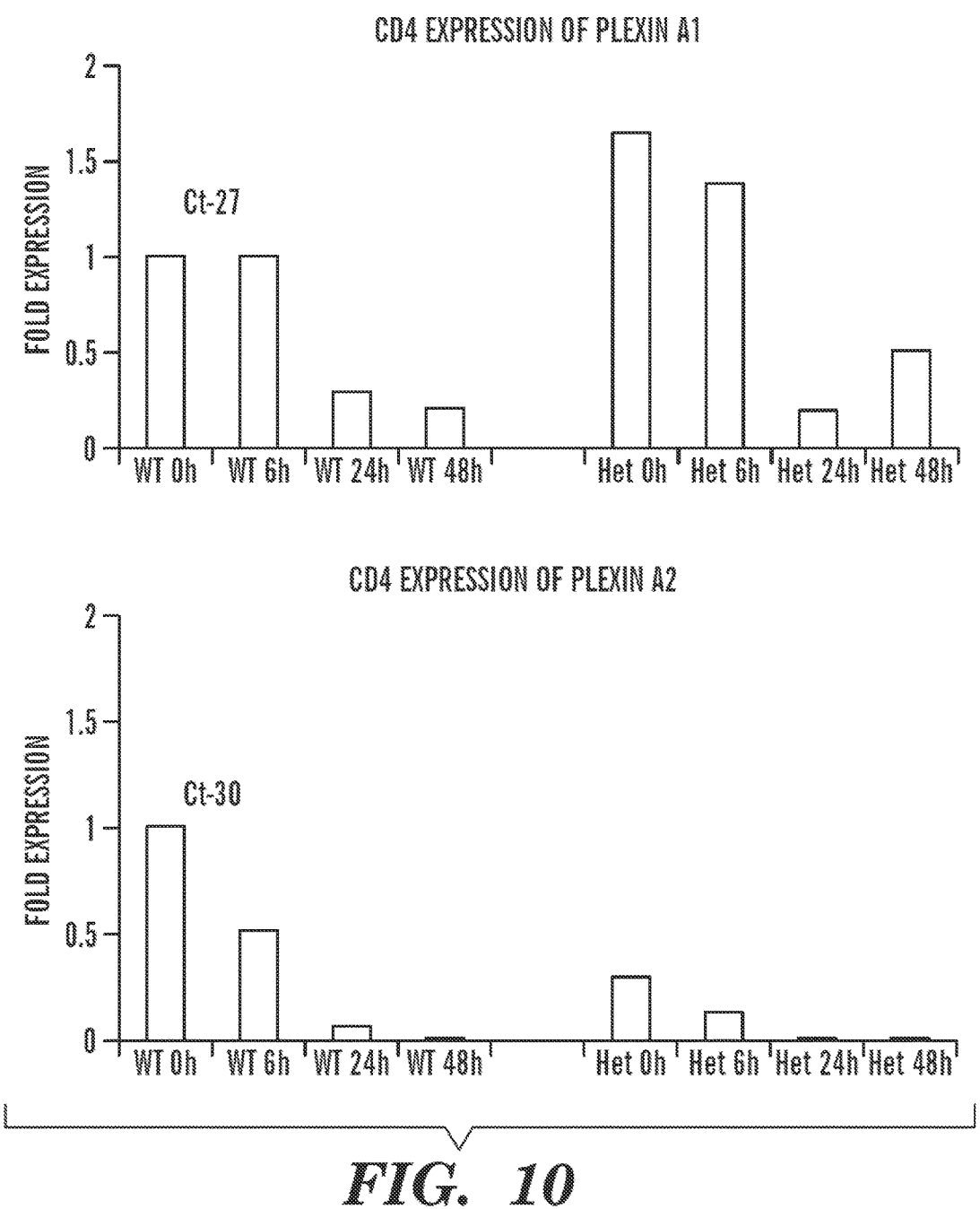
FIG. 10 depicts the expression levels of Plexin family molecules on murine CD4+ T cells either unactivated or following mitogen activation from 6-48 hrs. Expression was examined in wildtype and in NRP-2 heterozygous mice.
Figure 10:
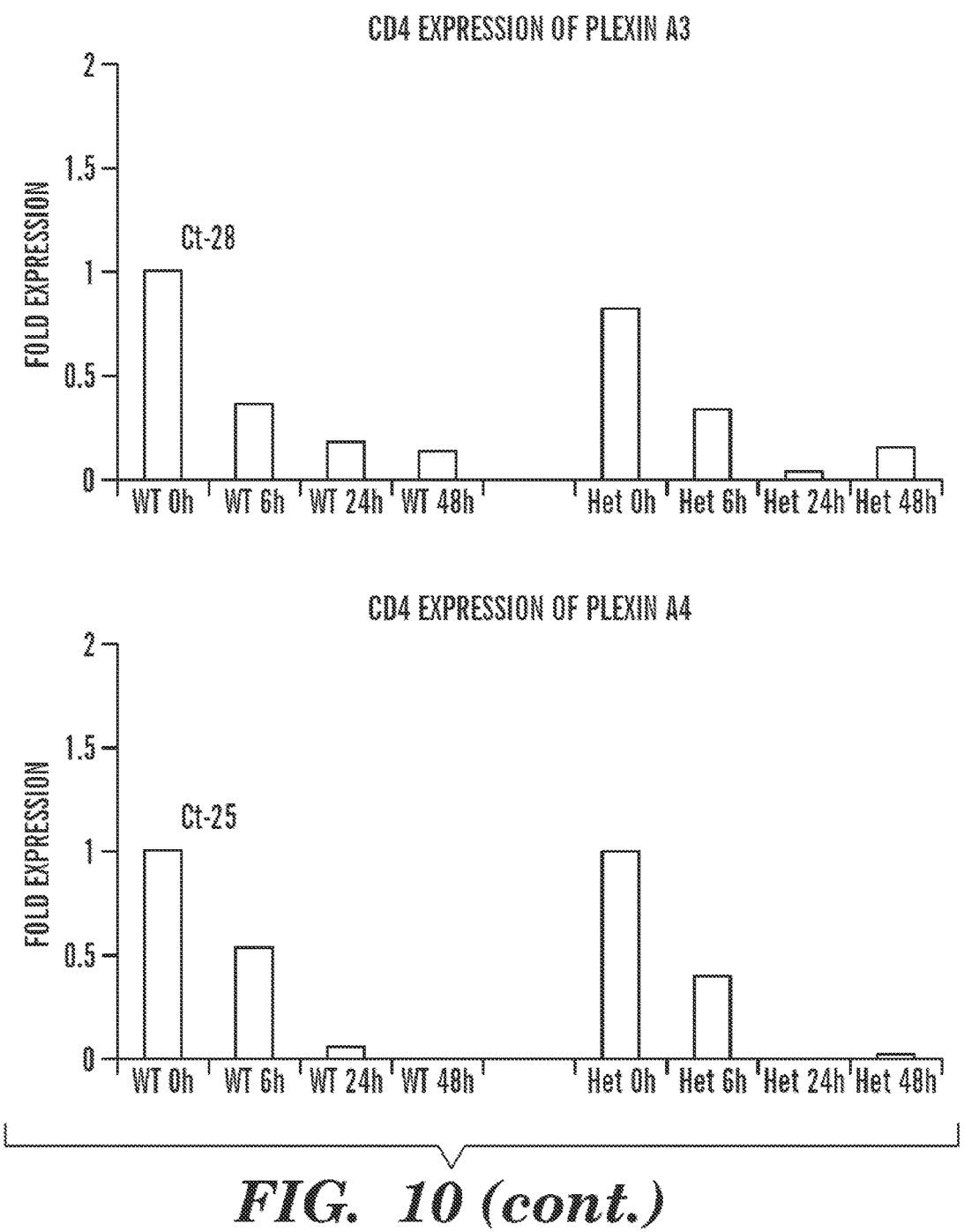
Figure 11:
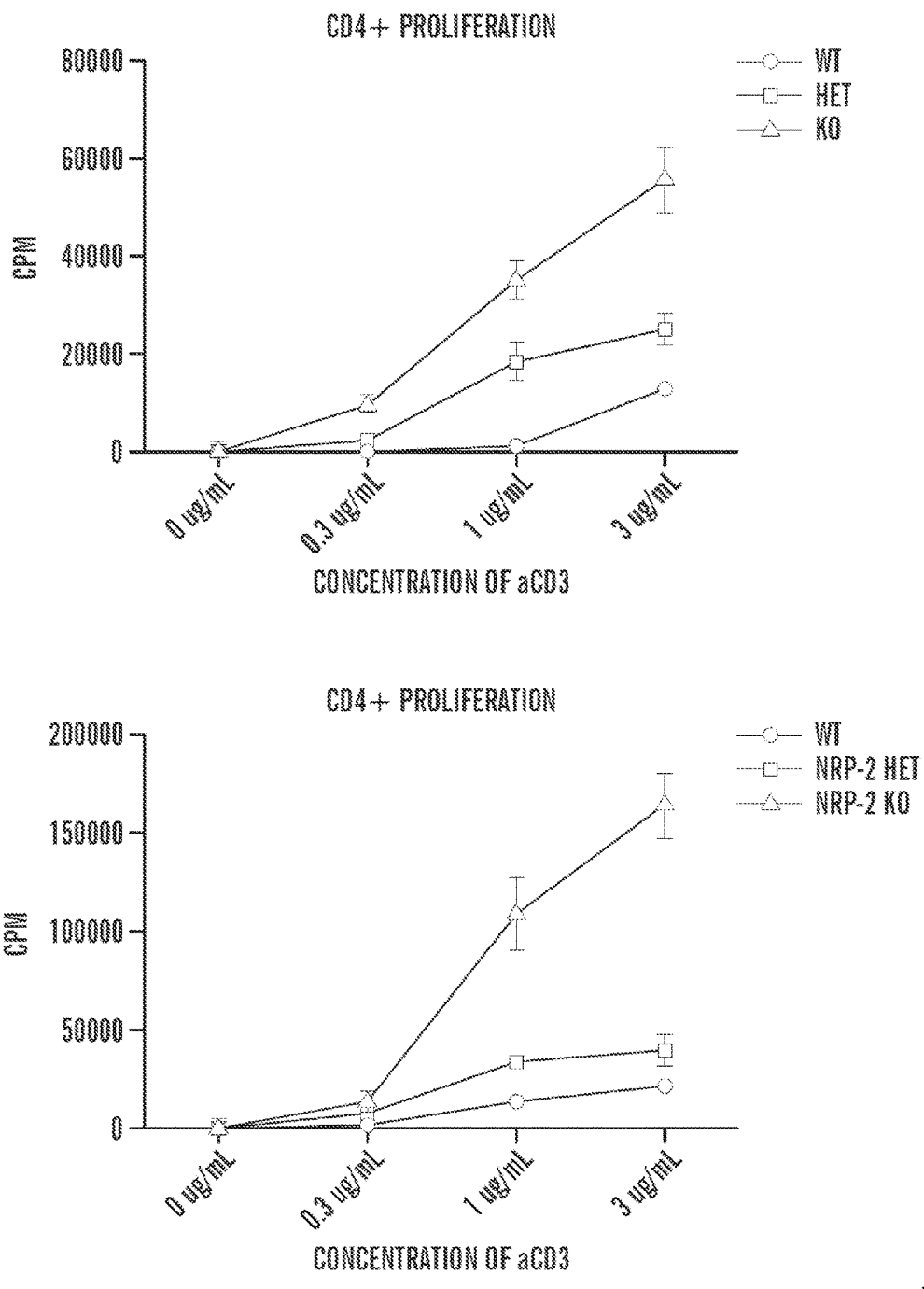
FIG. 11 depicts graphs of CD4+ proliferation. Wildtype, NRP-2 Heterozygous, and NRP-2 knockout CD4+ were isolated from spleen and plated at $5\times10^4$ per well and treated with plate-bound anti-CD3 at the indicated concentrations 0-3 mcg/ml. Graphs depict two experiments using different groups of mice (representative of n>5 experiments).
Figure 13:
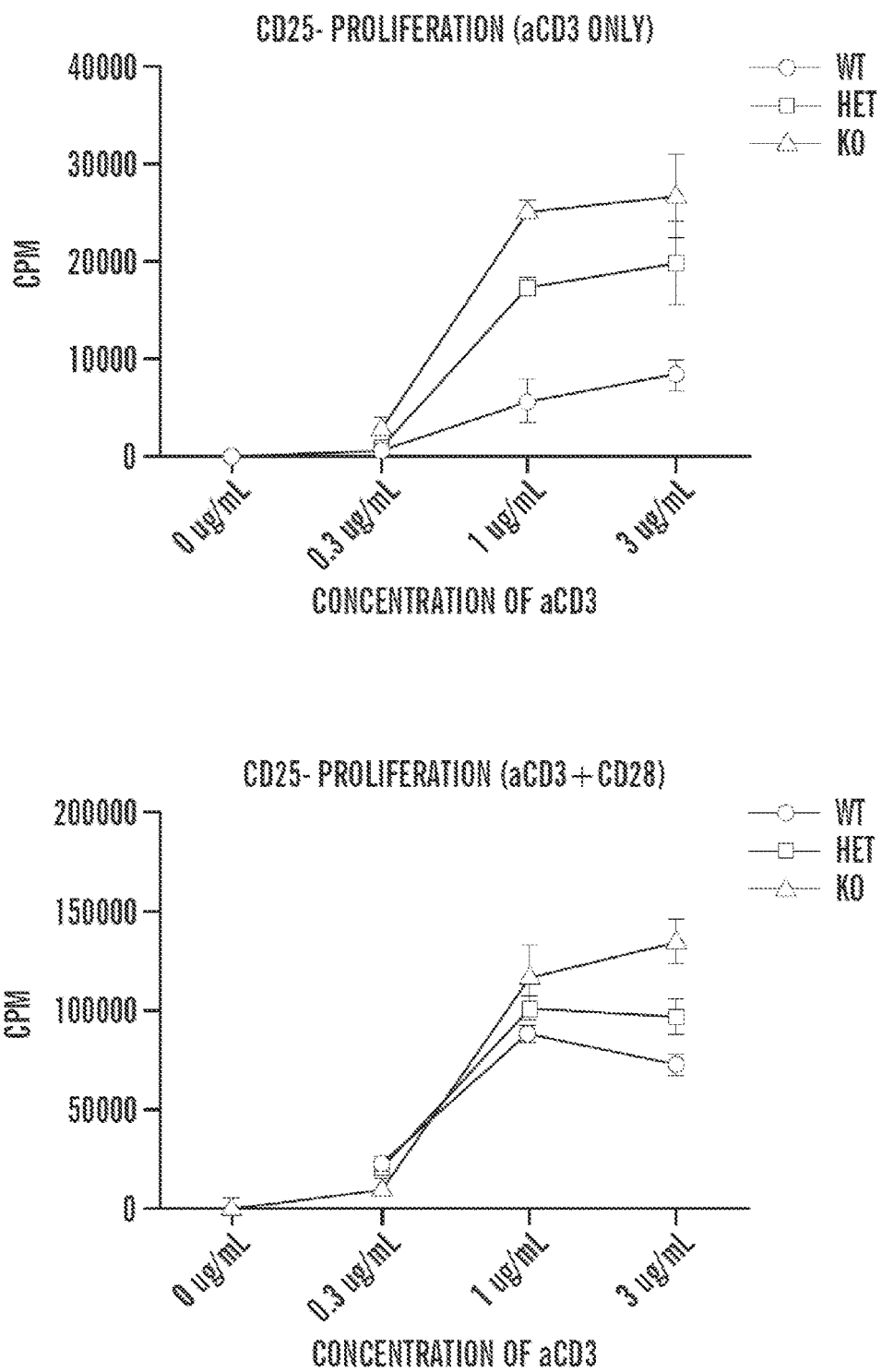
FIG. 13 depicts graphs of mitogen-induced proliferation of CD4+CD25$^{neg}$ T cells. Splenic C D4+ T cells were sorted into CD25$^{neg}$ T effector subsets from WT, NRP-2+/−(Hets) and NRP-2−/−(KO) mice on a C57BL/6 background and were plated at $5\times10^4$ per well in the presence of platebound anti-CD3 (0, 0.3, 1, or 3 ug/mL as indicated). The upper graph shows cells plated in the absence of anti-CD28 while the bottom graph depicts cells plated in the presence of agonistic anti-CD28 at 1 mcg/ml.

NRP-2 can complex with Plexin family molecules to elicit a regulatory signal, and Plexins family molecules are expressed on CD4+ T cells (FIG. 10). Thus, NRP-2 may elicit a regulatory signal in T cells via interactions with Plexins. The effect of NRP-2 on the proliferation of CD4+ cells was examined by plating wild type, NRP-2 het, and NRP-2 knockout cells on plates with plate-bound anti-CD3 at various concentrations. T cell activation as manifest by cytokine production and proliferation was increased in cells with reduced levels of NRP-2 proliferation (FIG. 11). Similar experiments measuring the proliferation of CD4+CD25− cells were also performed with added costimulation by anti CD28 (1 ug/mL) (FIG. 13). NRP-2 knockouts displayed increased activation but less so in the presence of a CD28. This indicates that NRP-2 can function in the resolution of the T cell activation response vs. the initiation of the activation response.

Figure 12:
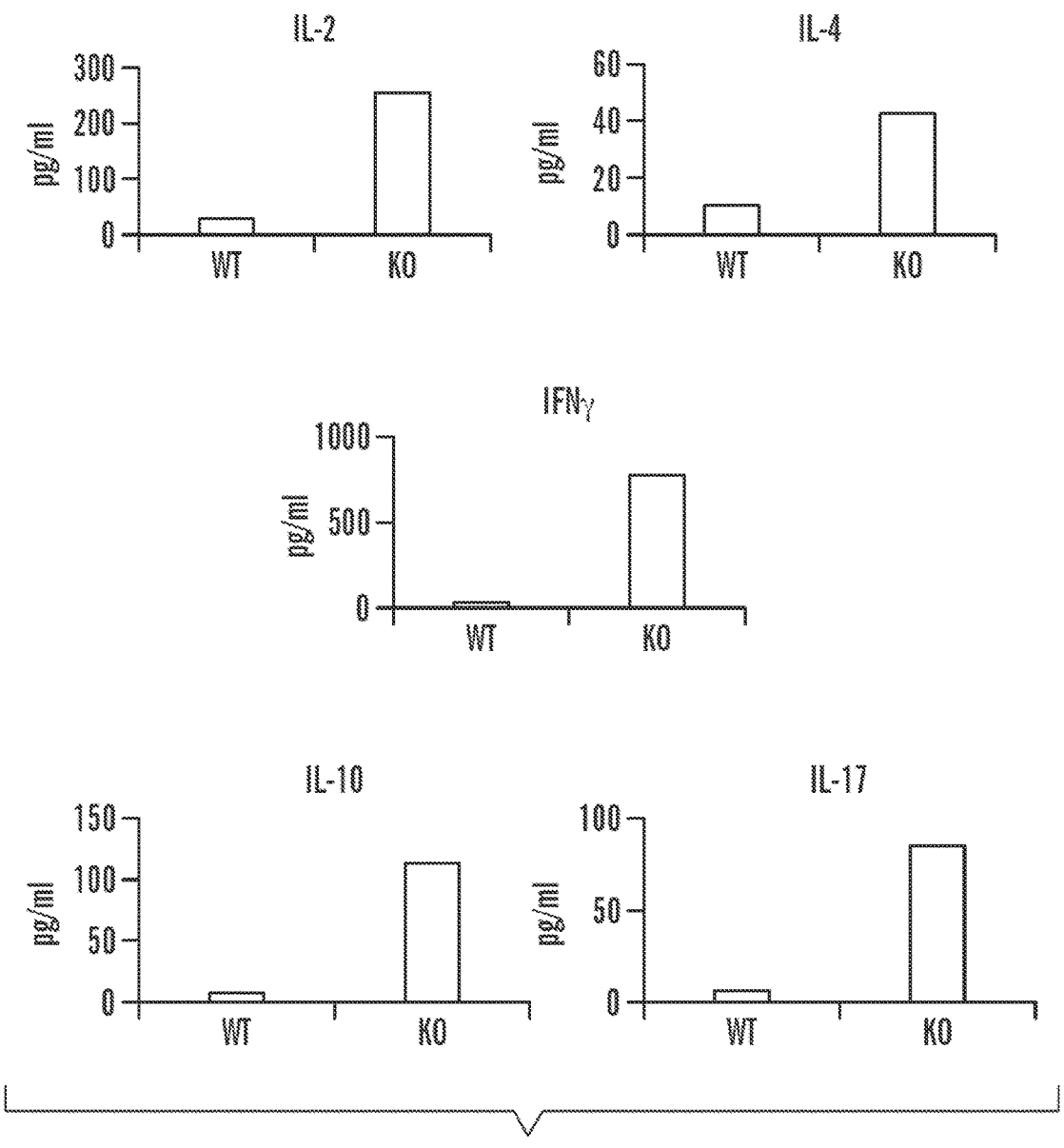
FIG. 12 depicts graphs of cytokine production in Wild type and NRP-2 knockout cells from FIG. 10. CD4+ T cells were mitogen activated (3 mcg/ml, as shown in FIG. 10) and levels of the indicated cytokines in the culture supernatants were examined after 72 hours by Luminex assay.
Figure 14:
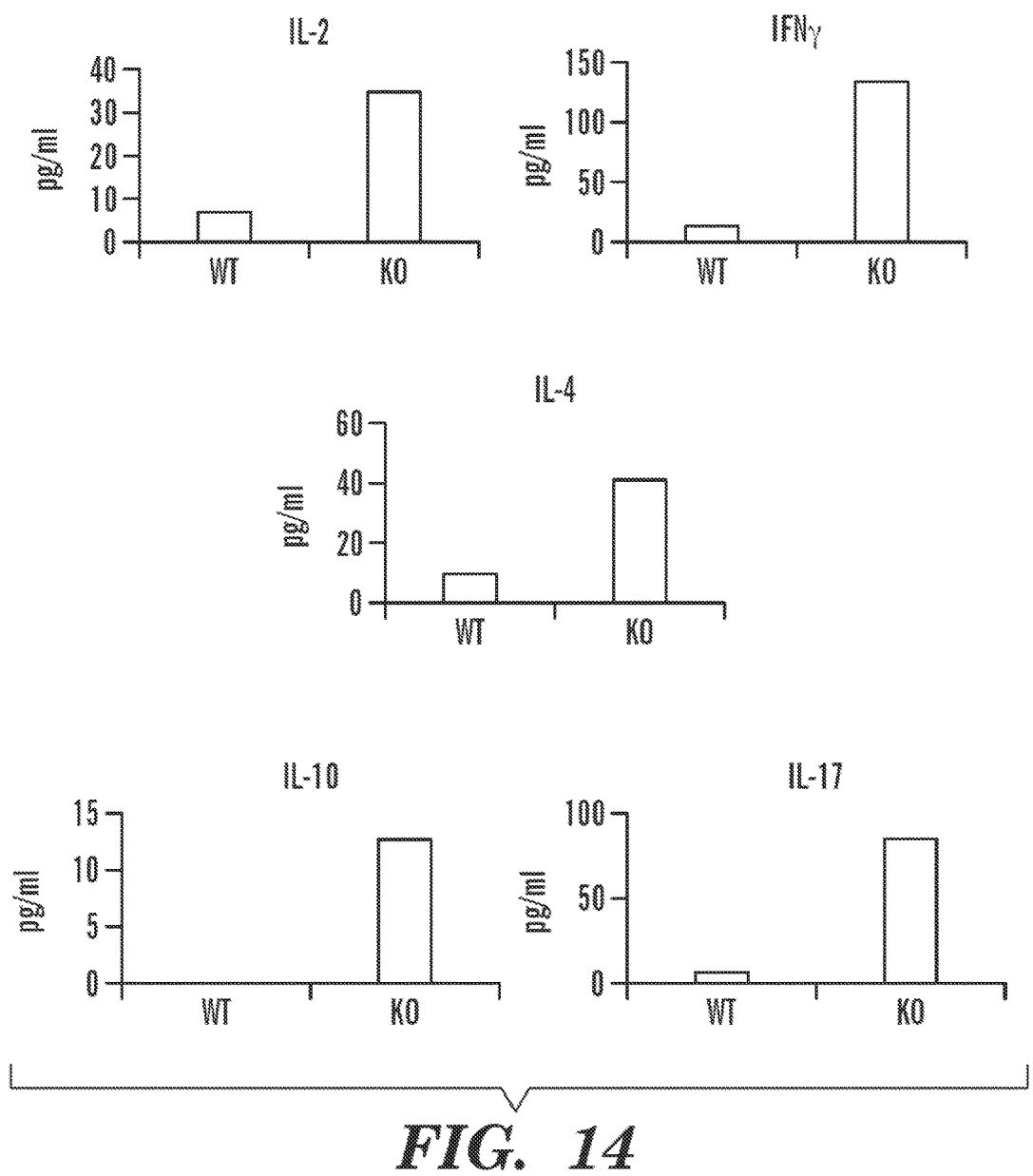
FIG. 14 depicts graphs of cytokine production in NRP-2 knockout CD4+CD25$^{neg}$ cells from the experiments shown in FIG. 12. NRP-2 knockout cells were mitogen activated with anti-CD3 (3 mcg/ml) and levels of the indicated cytokines in the culture supernatant were examined after 72 hours by Luminex assay.
Figure 15:
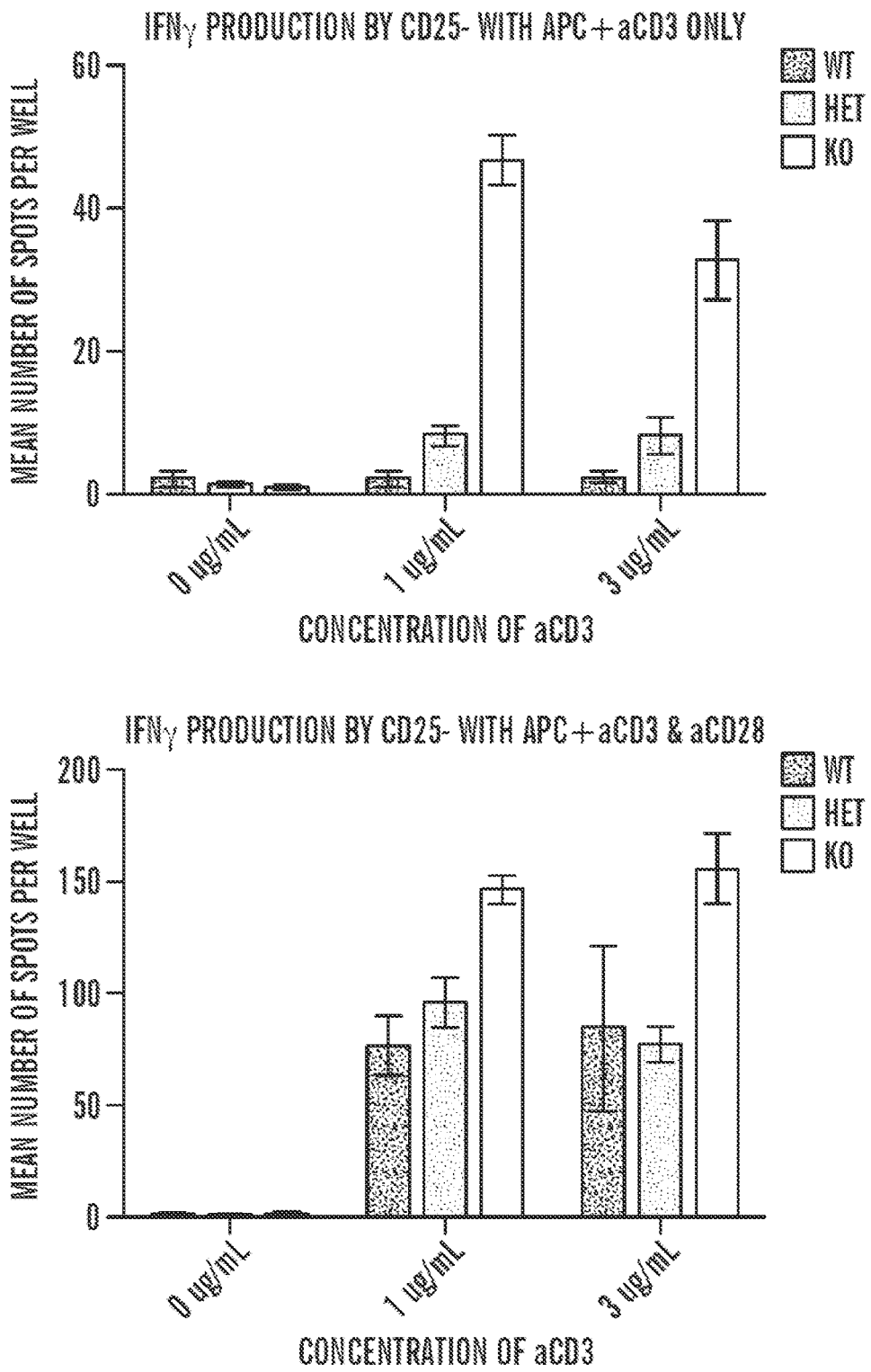
FIG. 15 depicts graphs of IFNγ production in mitogen activated CD25$^{neg}$ CD4+ T cells as measured by the ELISPOT Assay. Wildtype (WT), NRP-2 HET, and NRP-2 KO cells (at $1\times10^5$ per well with APCs at a 1:1 ratio) were exposed to anti-CD3 at 0, 1, or 3 mcg/ml with (bottom graph) or without (upper graph) agonistic anti-CD28 at 1 mcg/ml.
Figure 16:
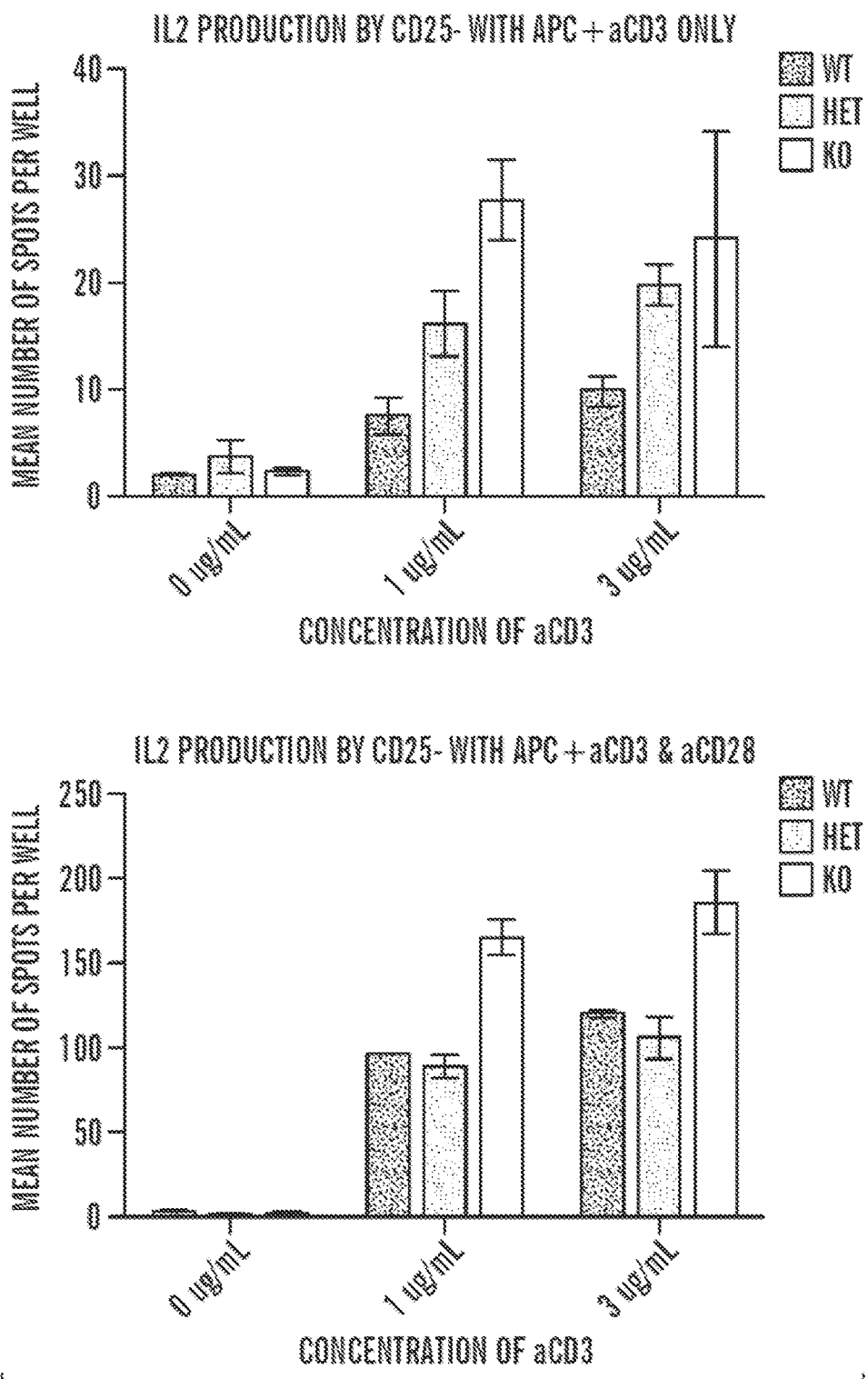
FIG. 16 depicts graphs of IL-2 production in mitogen activated CD25$^{neg}$ CD4+ T cells as measured by the ELISPOT Assay. Wildtype (WT), NRP-2 HET, and NRP-2 KO (at $1\times10^5$ per well with APCs at a 1:1 ratio) were exposed to anti-CD3 at 0, 1, or 3 mcg/ml with (bottom graph) or without (upper graph) agonistic anti-CD28 at 1 ug/mL.
Figure 17:
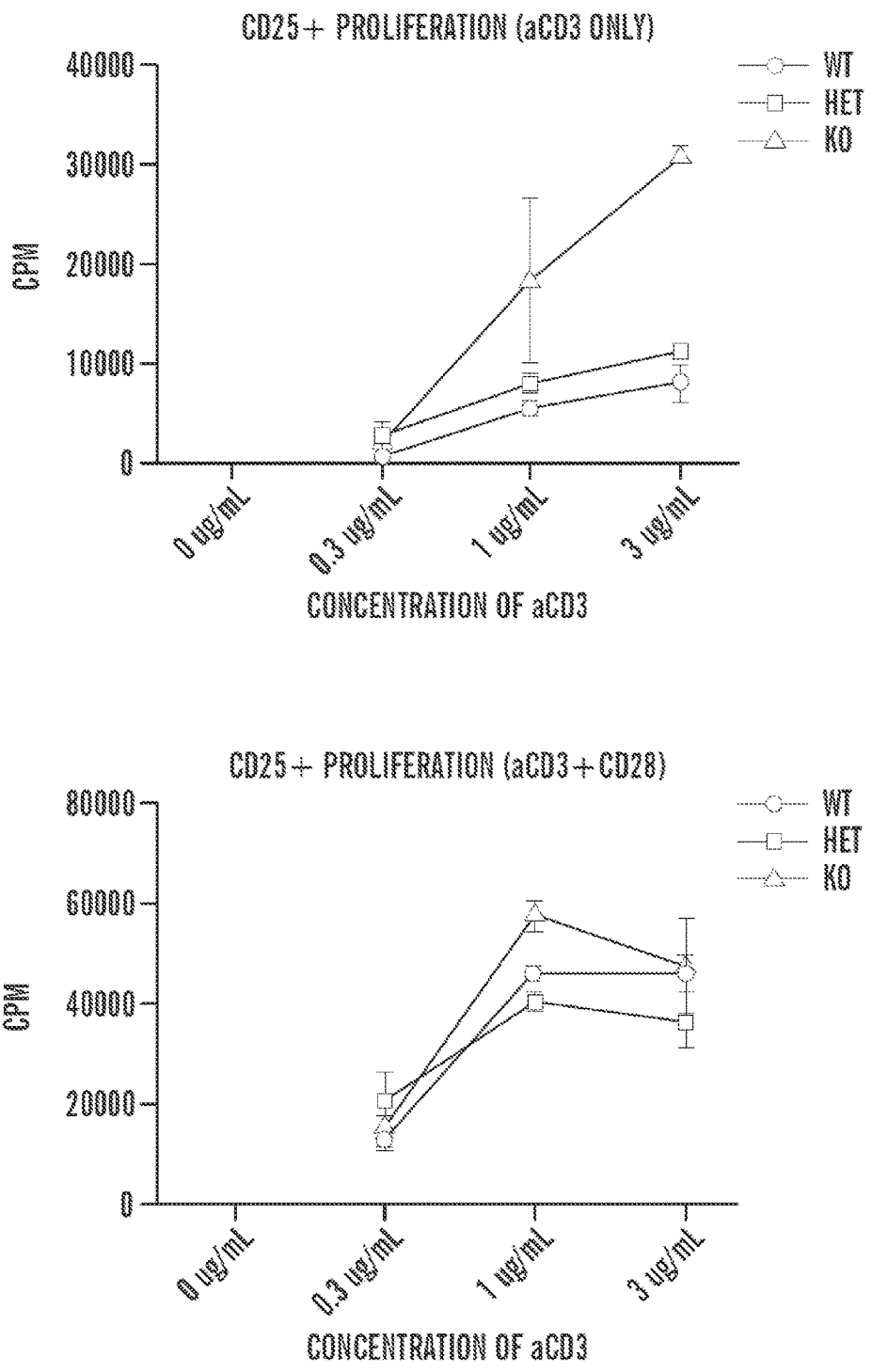
FIG. 17 depicts graphs of proliferation of CD4+CD25+ T cells. Wildtype (WT), NRP-2 HET, and NRP-2 KO (at $5\times10^4$ per well) were exposed to platebound anti-CD3 at 0, 0.3, 1, or 3 mcg/ml with (bottom graph) or without (upper graph) anti-CD28 at 1 mcg/ml
Figure 24:
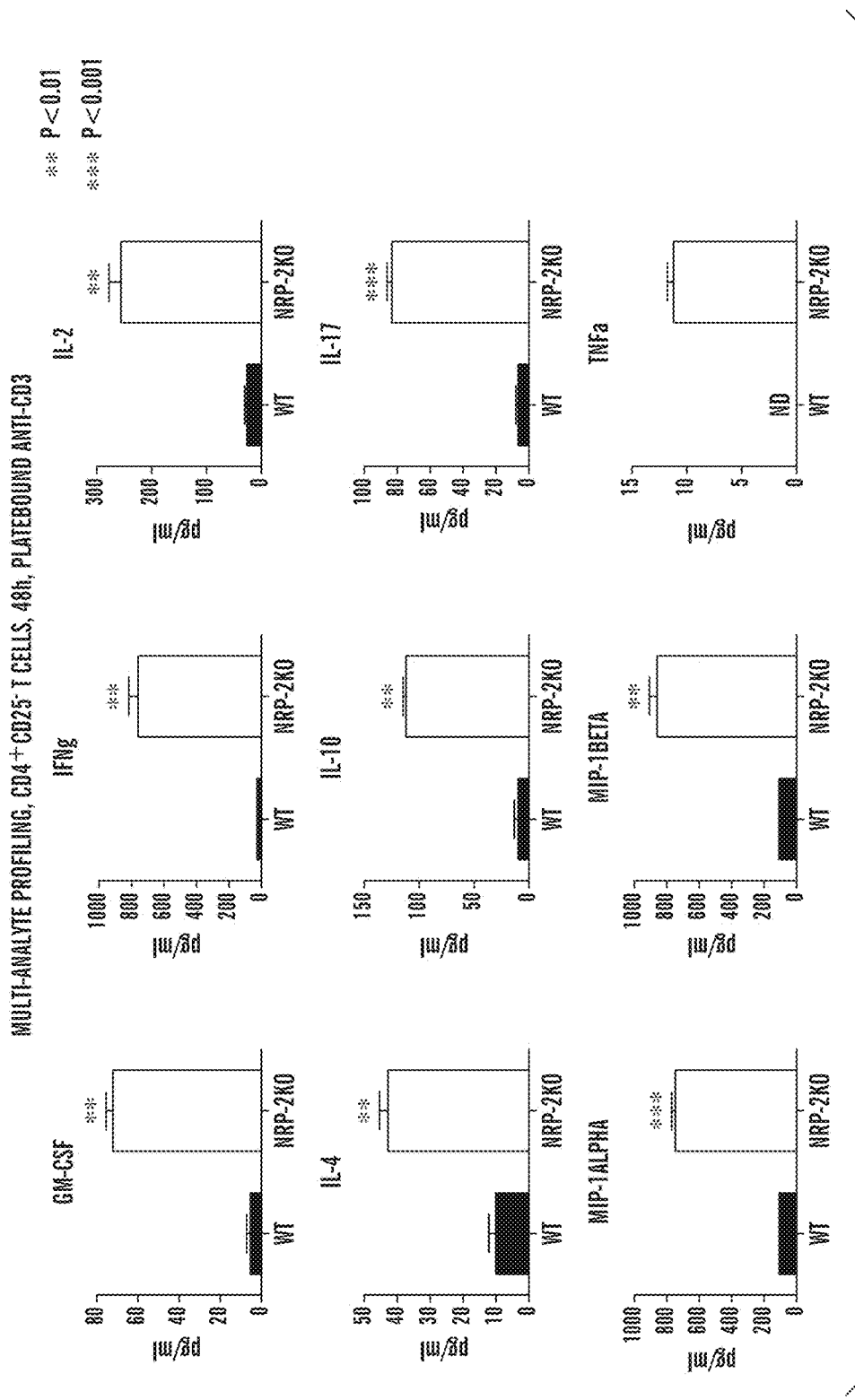
FIG. 24 depicts graphs of cytokine production in NRP-2 knockout CD4+CD25$^{neg}$ cells. NRP-2 knockout cells were mitogen activated with anti-CD3 and levels of the indicated cytokines in the culture supernatant were examined after 48 hours by Luminex assay. These findings are similar to those shown in FIG. 12.

NRP-2 knockout CD4+ T cells were subjected to mitogen activation and cytokine production in the culture supernatant was examined 72 hours after activation. NRP-2 knockouts displayed increased production of cytokines (FIG. 12). Increased cytokine production was also observed in NRP2 knockout CD4+CD25− T cells 48 and 72 hours after mitogen activation with anti-CD3 (FIG. 14 and FIG. 24). Production of IFNγ and IL2 was also examined by ELISPOT assay (FIGS. 15 and 16), which similarly demonstrated increased cytokine production in NRP2 knockout cells.

Sema3F Modulates PI-3K/Akt-mTOR Signaling

Figure 18:
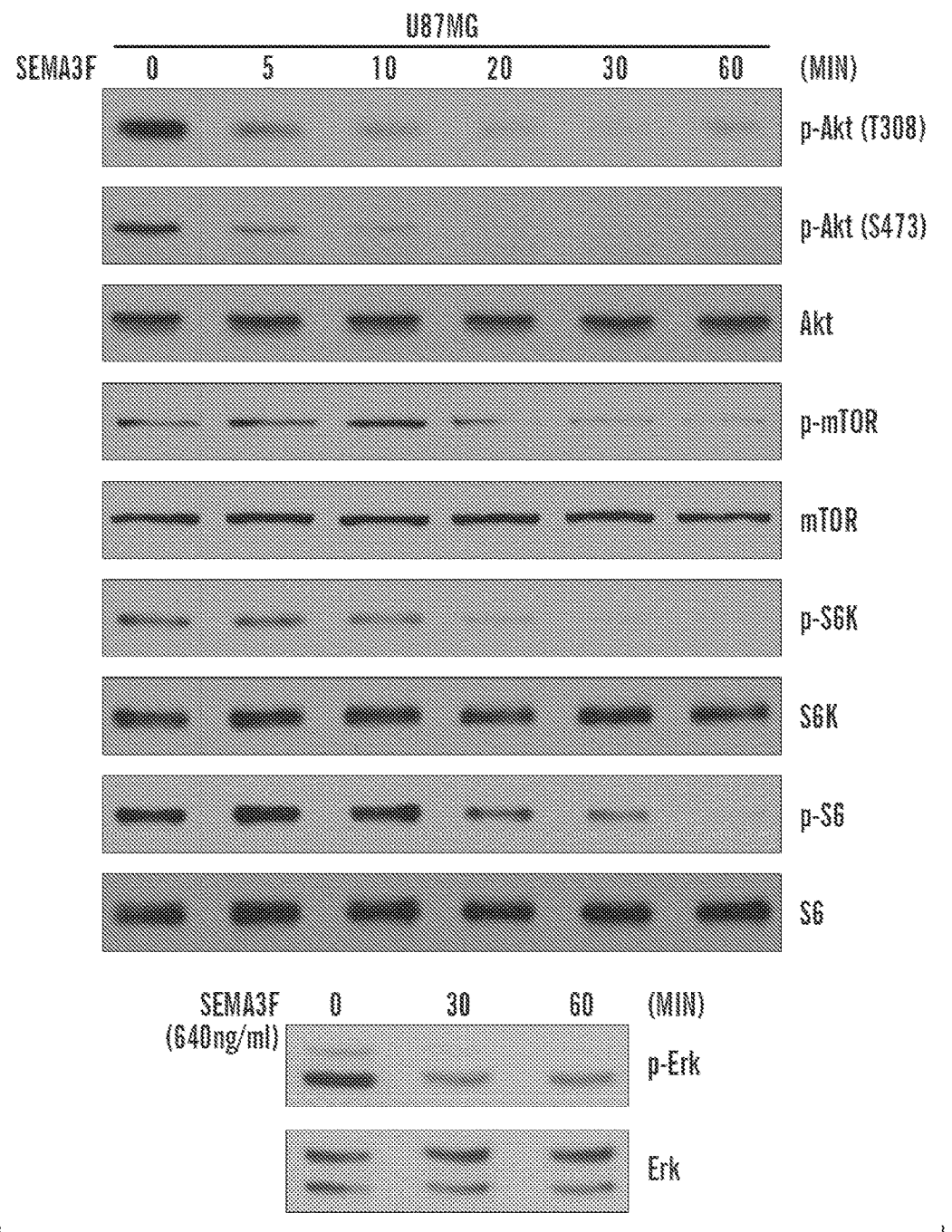
FIG. 18 depicts the time course effect of Sema3F on PI-3K/Akt-mTOR signaling (upper blot) and MAPK signaling (lower blot). U87MG which express NRP-2 were used for this assay. It was observed that cells treated with Sema3F at ~640 ng/mL for up to 60 mins have a reduced level of pAkt (mTORC2) and pS6K (mTORC1) and pERK as measured by Western Blot analysis.
Figure 19:
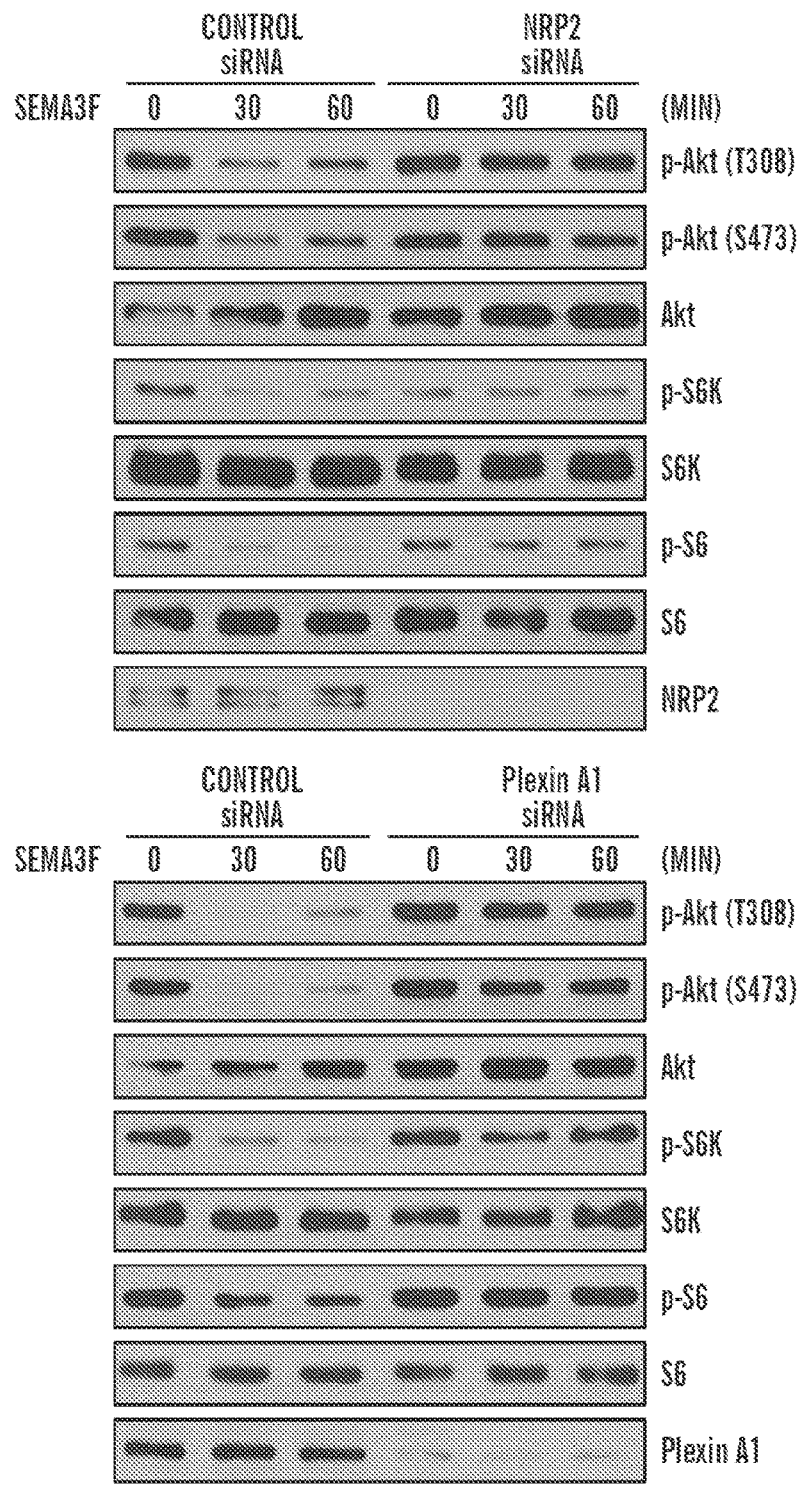
FIG. 19 depicts the effect of NRP-2 (upper) and PlexinA1 (lower) knockdown on Sema3F inhibition of PI-3K/Akt-mTOR signaling. U87MG cells were treated with a control, NRP-2 or PlexinA1 siRNA. Cells were then treated with Sema3F at ~640 ng/mL for up to 60 mins Knockdown efficiency was evaluated by Western Blot analysis. PI-3K-Akt signaling activity was measured by evaluating the level of pAkt (mTORC2), pmTOR and pS6K (mTORC1) expression.

U87MG cells, known to express high levels of NRP-2, were treated with Sema3F at a level known to stimulate a signaling response (~640 ng/mL) Inhibition of pAkt (mTORC2) and pS6K (mTORC1) dependent activation was observed (FIG. 18). Peak effects of SEMA3F were observed at ~600 ng/ml and this concentration of SEMA3F was used for all signaling analyses. As illustrated in the upper panel of FIG. 18, after 10 min SEMA3F inhibited the expression of pAkt (S473) (densitometry >80%) and by 30 min, there was a most significant reduction in pAkt (S473), pAkt (T308), pmTOR and pS6K. As illustrated in the lower panel of FIG. 18, the expression of pERK1/2 was markedly reduced in cells following SEMA3F treatment, with a peak effect by 30 mins.

siRNA was used to knockdown NRP-2 or PlexinA1 in U87MG cells which were then treated with Sema3F. Time course observation of the effect on the inhibition of pAkt (mTORC2) and pS6K (mTORC1) dependent activation in control siRNA and targeted siRNA cells indicated that knockdown of NRP-2 and PlexinA1 inhibited the effect of Sema3F (FIG. 19). As illustrated in the top panel of FIG. 19, SEMA3F failed to inhibit pAkt and pS6K following NRP2 knockdown. This finding confirms that SEMA3F elicits regulatory signaling via NRP2.

As discussed above, NRP-2 forms a complex with Plexin A1, and it is reported that Plexins elicit the NRP signaling response To test this possibility in the SEMA3F-NRP-2-elicited response, the effect of SEMA3F in U87MG cells following knockdown of Plexin A1 was evaluated. As illustrated in the bottom panel of FIG. 19, SEMA3F was potent to inhibit pAkt and pS6K in control siRNA-transfected cells, but again, it failed to elicit a response in Plexin A1 siRNA transfected cells. These observations indicate that the functional effect of SEMA3F on Akt-induced signals requires interactions between NRP-2 and Plexin A1 at the cell surface.

Figure 20:
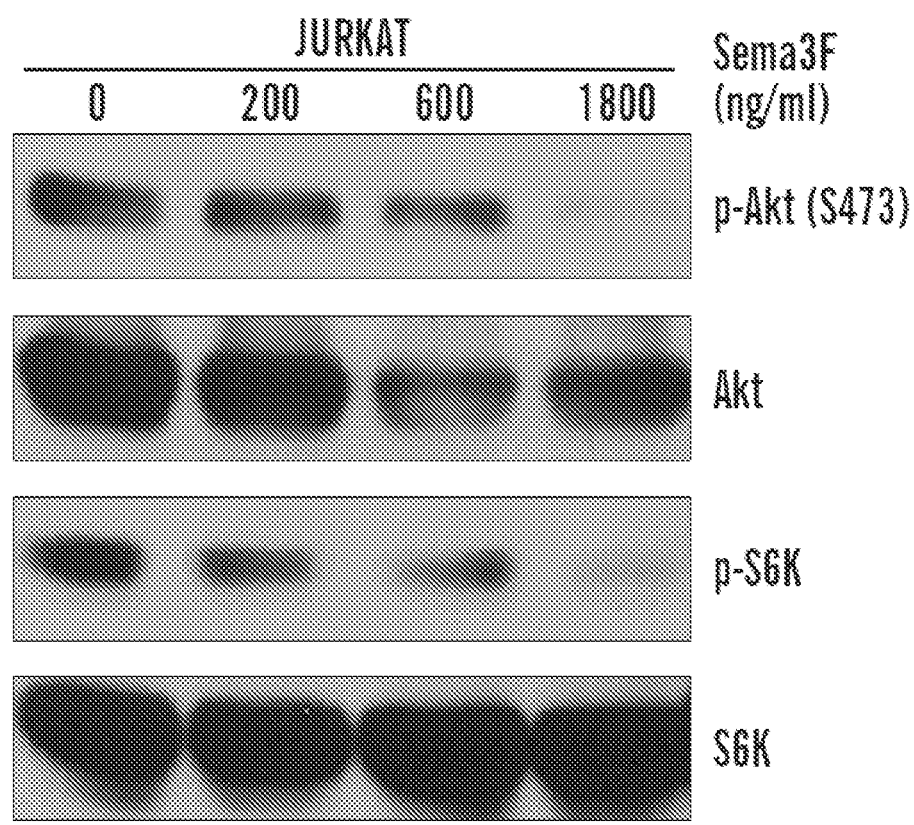
FIG. 20 depicts the results of Western blots of NRP-2-expressing Jurkat T cells treated with increasing concentrations of SEMA3F for 30 min. Expression of pAkt(S473) was evaluated by Western blot.

In addition, as illustrated in FIG. 20 NRP-2-expressing Jurkat T cells were treated with increasing concentrations of SEMA3F for 30 min. and expression of pAkt(S473) was evaluated by Western blot. Expression is reduced following treatment with high concentrations of SEMA3F (>600 ng/ml)

Figure 22:
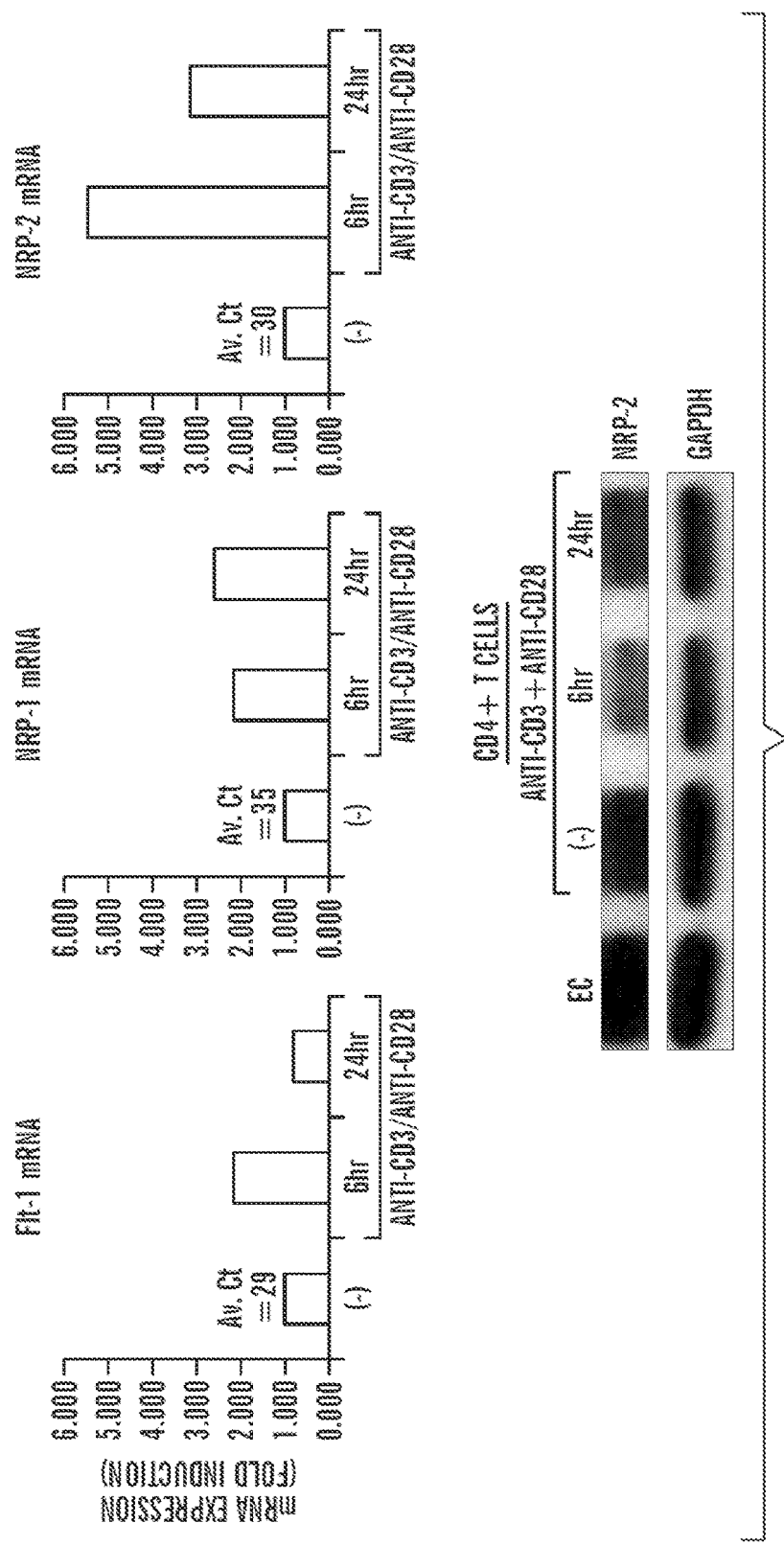
FIG. 22 demonstrates that NRP-1 and NRP-2 are expressed by human T cells. CD4+ T cells were purified from human PBMCs, and the expression of VEGFR1 (Flt-1), NRP-1 and NRP-2 mRNA was evaluated following mitogen-dependent activation (anti-CD3/anti-CD28). Illustrated is representative qPCR data (from n=3 experiments using different T cells) showing comparison between Flt-1, NRP-1 and NRP-2 mRNA expression. The bottom panel depicts Western Blot analysis comparing the expression of NRP-2 protein on unactivated and activated human CD4+ T cells vs. endothelial cells (EC).

Example 6: Expression of the Regulatory NRP-2 Receptor on Human CD4+ T Cells NRP-1 and NRP-2 bind VEGF as well as regulatory SEMA3A and SEMA3F respectfully. NRP-1 is expressed by Tregs. CD4+ T cells were purified from human PBMCs, and the expression of VEGFR1 (Flt-1), NRP-1 and NRP-2 mRNA was evaluated following mitogen-dependent activation (anti-CD3/anti-CD28). NRP-2 expression is markedly induced following activation, and is at higher levels than any other receptor (FIG. 22).

Example 7

Figure 6:
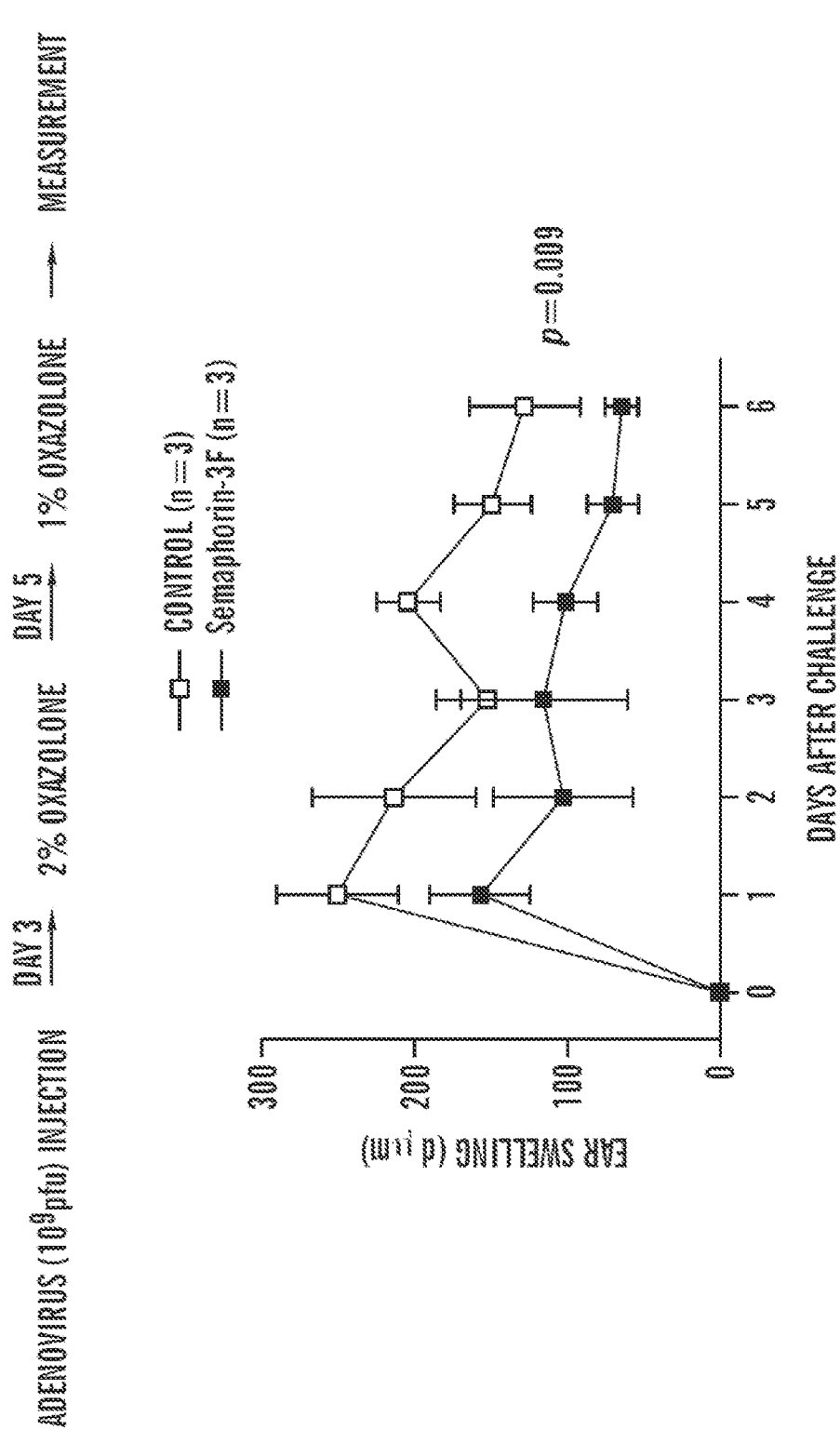
FIG. 6 depicts an oxazalone delayed type hypersensitivity response in mice treated with control adenovirus or adenovirus encoding Sema3F. Three days after a single IV injection of the adenovirus ($10^9$ pfu), mice were primed and challenged in the ear 5 days later with oxazalone using standard techniques. The graph shows the ear swelling in response to oxazalone.

Mice were injected with control adenovirus or adenovirus encoding Sema3F as described above herein. At Day 3 and Day 5 after adenovirus injection, the mice were further treated with oxozalone to induce ear swelling. Mice receiving the Sema3F treatment demonstrated reduced swelling relative to the mice receiving the control treatments (FIG. 6).

Example 8

Figure 23:
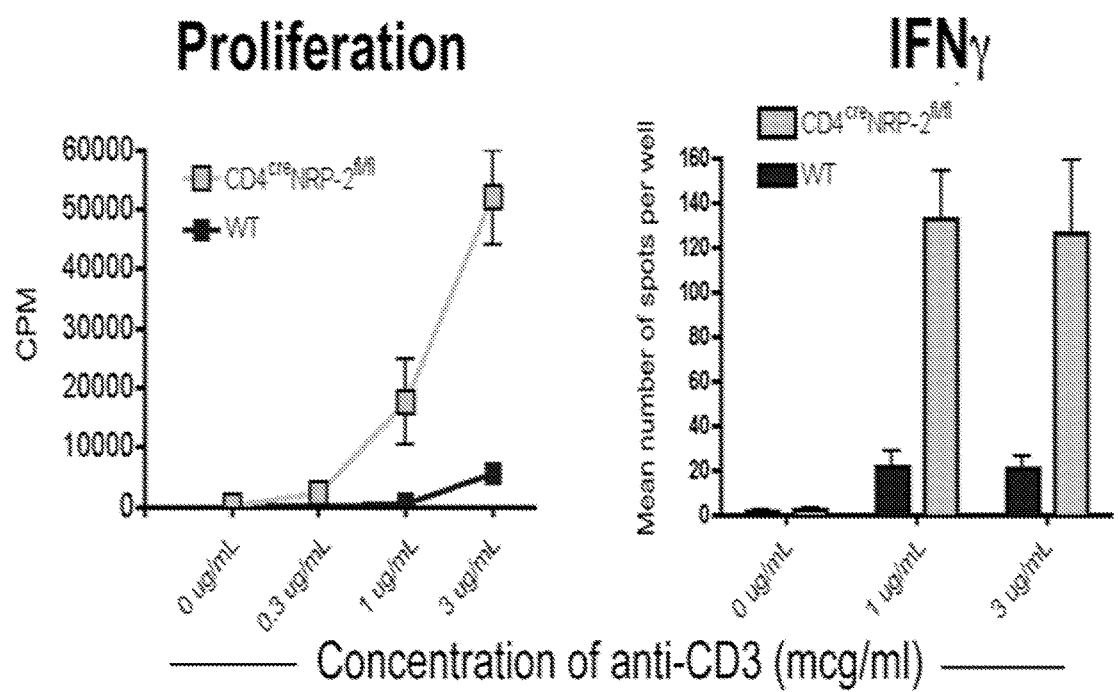
FIG. 23 depicts graphs of data showing that NRP-2 knockdown cells are hyperactive in response to stimulation. The left panel depicts CD4+ T cell proliferation in response to mitogen activation as measured by standard thymidine incorporation assay. The right panel depicts IFNg levels in CD4+ T cells in response to culture with APCs and anti-CD3.

CD4+ T cells were isolated from CD4creNRP-2fl/fl mice and were evaluated for the expression NRP-2 at the mRNA and protein level Minimal expression was noted. Cells were activated with increasing concentrations of mitogen, and proliferation was determined by standard thymidine incorporation assay. Also, CD4+ T cells were cultured with APCs and increasing concentrations of anti-CD3 and IFNg was assessed by ELISPOT assay. NRP-2 T cell activation responses were compared to wild type mice. Overall, NRP-2 knockdown cells were hyperactive which is consistent with in vivo findings that they mount an exaggerated rejection response (FIG. 23).

Example 9

Figure 25:
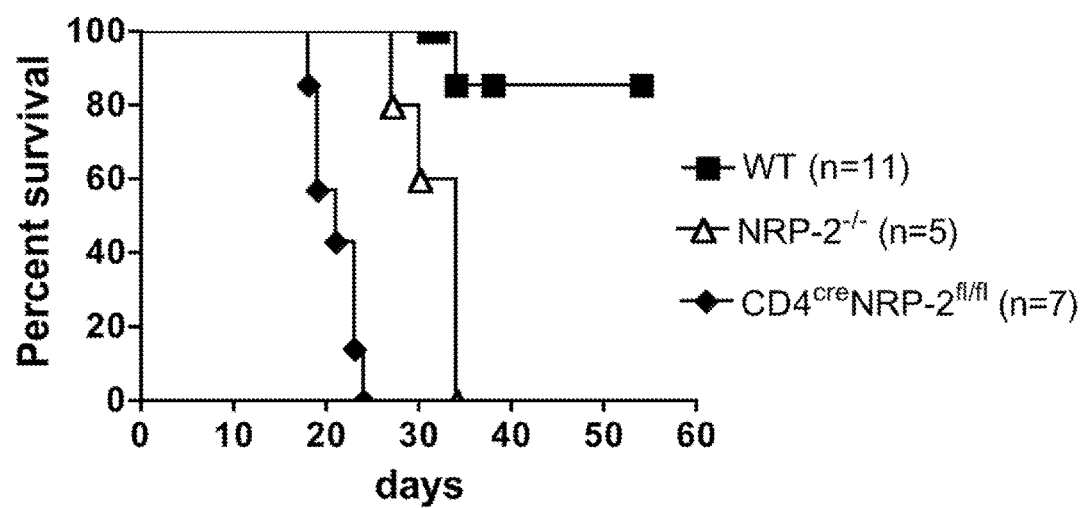
FIG. 25 depicts graft survival curves in a model of chronic allograft rejection. Cardiac Allografts B6.C-H$^{bm12}$(BM12) were transplanted into minor MHC mismatched recipients, either wild type C57BL/6(WT), NRP-2 knockout (NRP-2−/−) or select CD4+ T cell NRP-2 Knockout mice (CD4$^{Cre}$-NRP-2$^{fl/fl}$).

FIG. 25 depicts graft survival curves in a model of chronic allograft rejection. Cardiac Allografts B6.C-H$^{bm12}$ (BM12) were transplanted into minor MHC mismatched recipients, either wild type C57BL/6(WT), NRP-2 knockout (NRP-2−/−) or select CD4+ T cell NRP-2 Knockout mice (CD4$^{Cre}$-NRP-2$^{fl/fl}$). As expected, cardiac allografts survive long term in WT mice; however, knockout mice mount an accelerated rejection response.

Example 10: Expression of NRP-2 on Human CD4+ T Cells

Figures 26A, 26B, 26C:
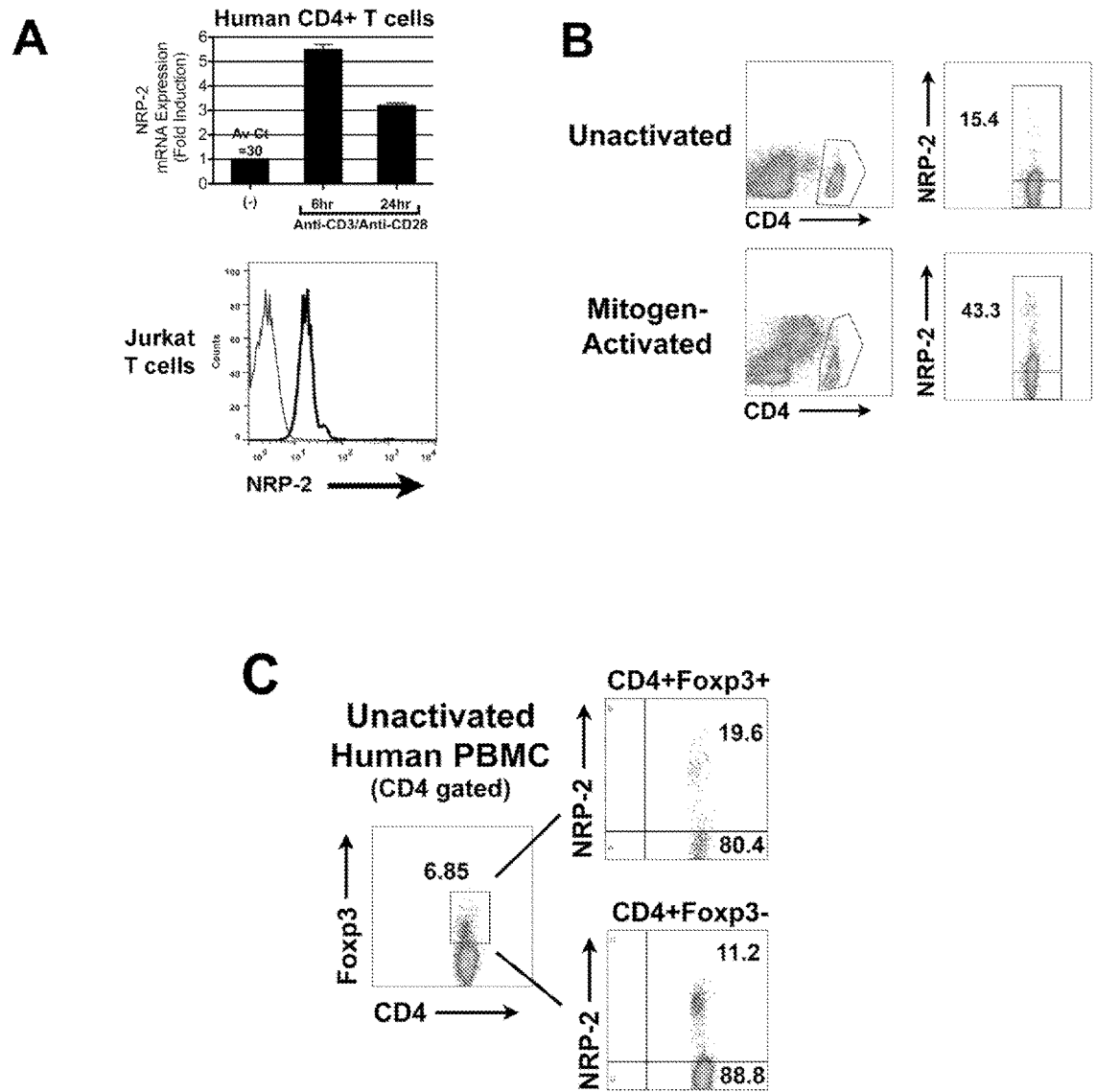
FIGS. 26A-26C show data demonstrating the expression of NRP-2 on Human CD4+ T cells.

Human CD4+ T cells were isolated by negative selection from Human Peripheral Blood. Expression of NRP-2 was evaluated by qPCR on unactivated and mitogen (Anti-CD3/CD28) activated cells (FIG. 26A). Note that mRNA expression increases upon activation. Expression was also evaluated on a human Jurkat T cell line. By FACS, Jurkats express high levels of NRP-2.

Human peripheral blood cells were isolated by standard Ficoll separation and were used unactivated or following mitogen-activation. NRP-2 expression was evaluated by FACS on the CD4+ subset (FIG. 26B). Protein expression increases following activation.

Peripheral blood cells were stained with anti-CD4, anti-FoxP3 and NRP-2 (FIG. 26C). Illustrated is expression as evaluated by FACS showing that both FoxP3+ human CD4+ T regulatory cells and non-FoxP3/T effector cells express NRP-2.

Example 11: Expression of NRP-2 on Murine CD4+ T Cells

Figure 27A:
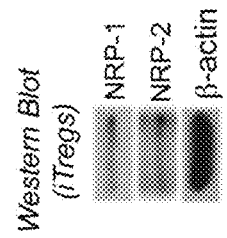
FIGS. 27A-27F show data demonstrating expression of NRP-2 on murine CD4+ T cells.
Figure 27B:
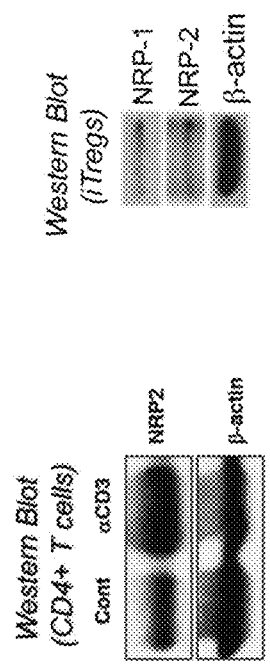
Figure 27D:
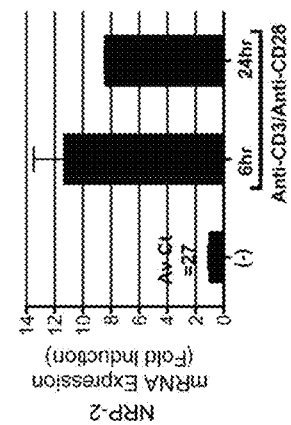
Figure 27E:
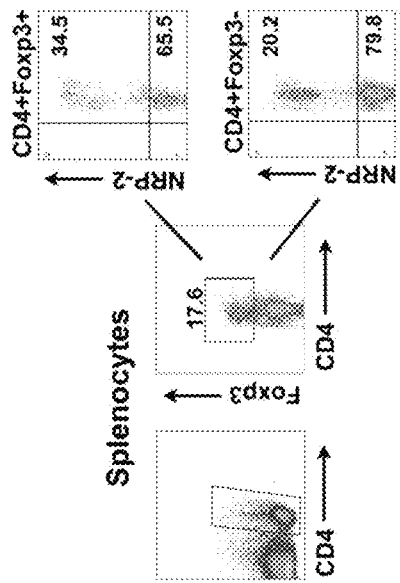
Figure 27F:
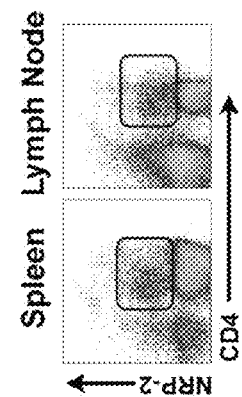
Figure 27C:
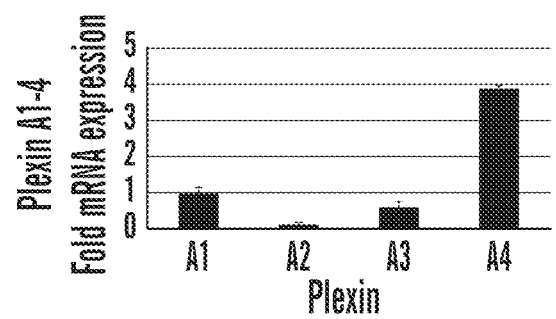

FIG. 27A depicts FACS analysis of NRP-2 on CD4+ T cells within murine spleen and lymph node. Note that distinct populations of CD4$^+$ T cells express NRP-2. CD4+ T cells were isolated by negative selection from murine spleen. Expression of NRP-2 was evaluated by qPCR on unactivated and mitogen (Anti-CD3/CD28) activated cells (FIG. 27B). Note that expression increases upon activation. Plexin A family molecules were also evaluated on isolated CD4+ T cells. Expression of Plexin A1 and A4 appear to be highest on this subset (FIG. 27C). CD4+ T cells were isolated by negative selection from murine spleen and the expression of NRP-2 was evaluated on Foxp3+ and Foxp3 negative subsets (FIG. 27D). NRP-2 is expressed on both subsets of unactivated CD4+ cells. Isolated Splenic CD4+ T cells were mitogen activated (anti-CD3-1 mcg/ml) and expression of NRP-2 was evaluated by Western Blot analysis (FIG. 27E). Again NRP-2 is found to be increased in expression upon activation. CD4+ T cells were driven to differentiation into induced Treg cells in standard culture medium (mitogen+TGFb+anti-IL-4+anti-IFNg+retinoic acid) and expression of NRP-1/2 was evaluated by Western Blot (FIG. 27F). On this cell type NRP-2 is co-expressed with NRP-1

Example 12: Regulation of mTOR Signaling by Semaphorin 3F Neuropilin 2 Interactions In Vitro and In Vivo Semaphorin 3F (SEMA3F) provides neuronal guidance cues via its ability to bind neuropilin 2 (NRP2) and Plexin A family molecules. Described herein is the analysis of SEMA3F-NRP2 signaling responses in human endothelial, T cell and tumor cells using phosphokinase arrays, immunoprecipitation and Western blot analyses. Consistently, SEMA3F inhibits PI-3K and Akt activity, and responses are associated with the disruption of mTOR/rictor assembly and mTORdependent activation of the RhoA GTPase. It is also described herein that the expression of vascular endothelial growth factor, as well as mTOR-inducible cellular activation responses and cytoskeleton stability are inhibited by SEMA3F-NRP2 interactions in vitro. In vivo, local and systemic overproduction of SEMA3F reduces tumor growth in NRP2-expressing xenografts. Taken together, SEMA3F regulates mTOR signaling in diverse human cell types, indicating that its biology has broad implications in chronic disease.

INTRODUCTION

Neuronal networking is regulated by the response of axonal growth cones to environmental cues, both positive and negative. For instance, cues elicited by netrin-1 are chemoattractive, whereas those dominated by semaphorin 3F (SEMA3F) are chemorepulsive. These processes, known collectively as axon guidance, play an important role in the development of the central nervous system (1, 2). SEMA3F is a member of the class 3 semaphorins (SEMA3A-G), whose receptors are neuropilin 1 (NRP1), neuropilin 2 (NRP2) and Plexins (3, 4). Semaphorins are involved in vascular and tumor biology (5, 6) and an increasing body of data indicate that they regulate the immune response pertinent to tumor immunity (7, 8, 9, 10). In addition, they inhibit the migration of endothelial cells (EC) and tumor cells in vitro and attenuate tumor progression, metastasis and angiogenesis in vivo (5, 6). Nevertheless, the response of T cells, EC, smooth muscle cells and tumor cells to SEMA3F is poorly understood but functional effects are characterized by regulatory responses including anti-migration, cytoskeleton collapse and loss of stress fibers (5, 6, 11). Analysis of SEMA3F signaling mechanisms demonstrated that SEMA3F forms a complex with NRP2 and Plexin A1. This complex attracts the ABL2 tyrosine kinase, which activates p190RhoGAP, resulting in the inactivation of RhoA, a small GTPase that converts GTP to GDP, leading to depolymerization of F-actin and the loss of stress fibers with an associated diminished EC and tumor cell migratory response (6).

Gleevec (imatinib), an ABL2 tyrosine kinase inhibitor abrogates SEMA3-mediated loss of stress fiber formation and motility in glioblastoma cells and EC (12). H157 lung cancer cells stably transfected with SEMA3F have reduced levels of phosphorylated Akt (S473), STAT3 and Erk (13), and reduced Akt activity was associated with lower levels of expression of the angiogenic factor, vascular endothelial growth factor (VEGF) (13).

While semaphorins and NRP-elicited responses may regulate multiple intracellular signaling pathways, a common feature is the inhibition of the phosphorylation of the Akt kinase (2,13). This effect is highly suggestive that a major biological effect of semaphorin-induced signaling involves the inhibition of mTOR signaling. Indeed, a recent study demonstrated that invertebrate semaphorin-plexin interactions may regulate TOR signaling in Caenorhabditis elegans (C. elegans), which is required for morphological changes in its epidermal cells (14). mTOR is a serine/threonine kinase that exists as two distinct multiprotein complexes, composed of either mTOR, raptor and mLST8 (mTORC1) (15, 16), or mTOR, rictor, Sin1, protor and mLST8 (mTORC2) (17, 18, 19). mTORC1 controls cell growth in part by phosphorylating S6K1 and 4EBP1 and is a key regulator of protein translation (20, 21). mTORC2 mediates cell survival and activation by phosphorylating Akt (22) and serum/glucocorticoid-regulated kinase-1 (SGK1) and PKC((18, 23). There is great interest in targeting mTOR signaling pathways as a therapeutic for autoimmune disease, chronic inflammation and allograft rejection (24, 25, 26) and as an adjunct to cancer therapy (27). Nevertheless, little is reported on the effects of SEMA3F on this signaling pathway or in these disease processes despite widespread expression of its NRP2 receptor on human immune, epithelial and tumor cells (5, 6, 28).

It is described herein that SEMA3F interacts with NRP2 and Plexin A1 to reduce PI-3K activity, inhibit the assembly of mTORC2 and reduce downstream Akt signaling. It is also demonstrated that SEMA3F can elicit anti-tumor and anti-angiogenic effects by inhibiting PI-3K activity and Akt-induced transactivation of VEGF, which is well established to function in tumorigenesis and chronic inflammation. Collectively, these studies define SEMA3F as a novel PI-3K/mTORC2 inhibitor in mammalian cells, indicating that it has broad biological and clinical implications, and is a therapeutic to enhance the resolution of chronic disease.

Results

SEMA3F Inhibits Akt, mTOR, and S6K Phosphorylation.

Figures 34A, 34B, 34C, 34D:
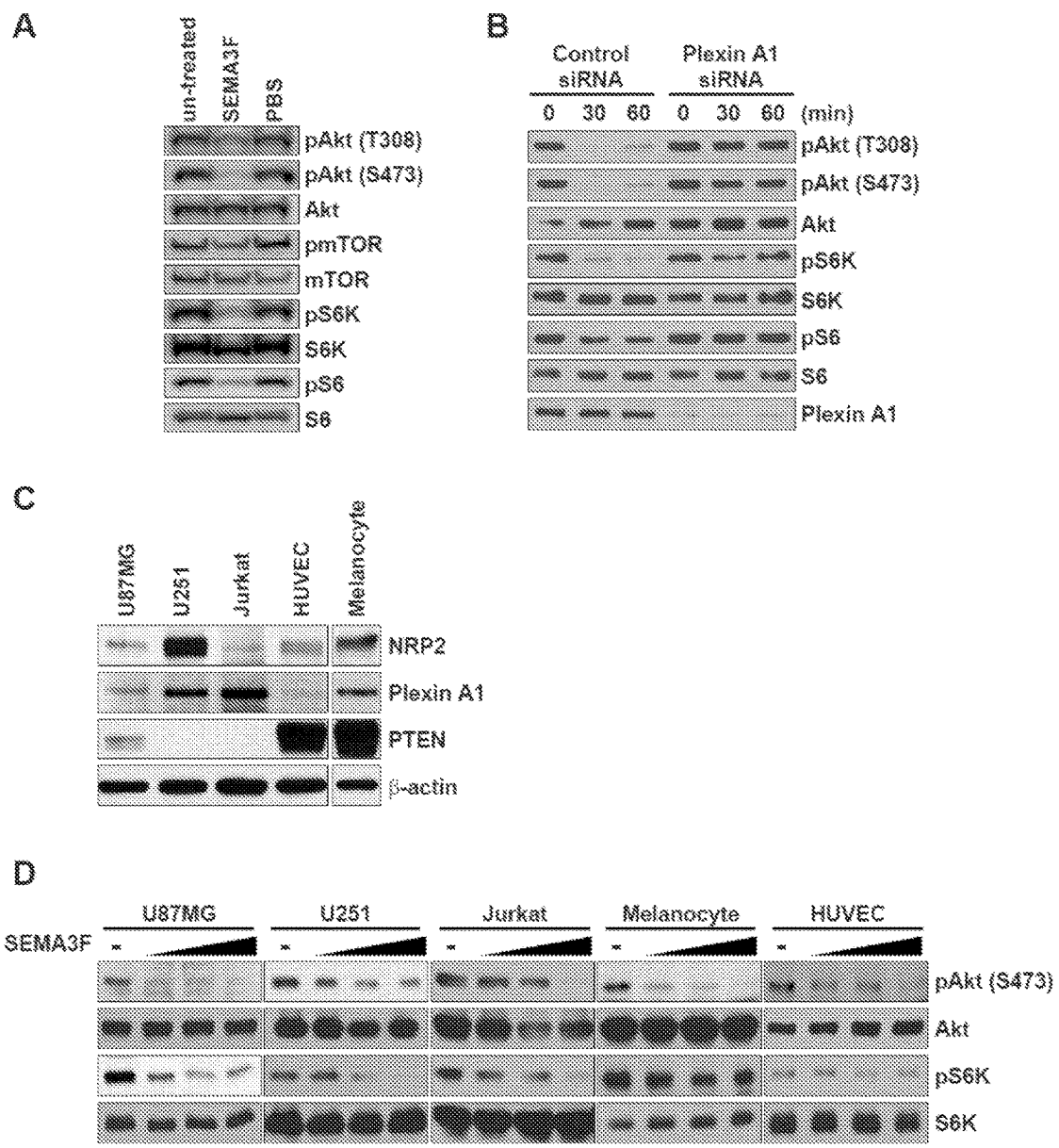
FIGS. 34A-34D depict analysis of intracellular signaling pathway regulated by SEMA3F.

To determine the effect of SEMA3F on intracellular signaling responses, levels of phosphokinases in the NRP2-expressing human glioblastoma cell line U87MG were profiled. It was found that SEMA3F inhibited the phosphorylation of a number of kinases, notably, Akt (T308 and S473), Erk (T202/Y204 and T185/Y187) and mTOR (S2448) (FIG. 28A; Table 1), which was confirmed by Western blot analysis (FIG. 28B). A time course analysis further indicated that pAkt (T308 and S473), pmTOR and its downstream signaling (pS6K and pS6) were inhibited within 10-20 minutes of SEMA3F treatment, and this inhibitory effect persisted for greater than 60 minutes (FIGS. 28C and 34A). SEMA3F failed to inhibit pAkt, pS6K and pS6 in both NRP2 and Plexin A1-siRNA transfected cells, indicating that the regulatory effect of SEMA3F on Akt/mTOR activity requires interaction with NRP2/Plexin A1 complexes at the cell surface (FIG. 19, top panel and 34B). SEMA3F also inhibited Akt (S473) and S6K phosphorylation in several other cell lines expressing NRP2, including U251 glioblastoma cells, a melanocyte cell line, Jurkat T lymphocytes, and endothelial cells (FIGS. 34C-34D). Using a standard ELISA-based assay29, it was also found that SEMA3F inhibited PI-3K activity in each cell line in a time dependent manner (FIG. 28D). In addition, pre-treatment of endothelial cells with SEMA3F (for 30 minutes) inhibited subsequent VEGF-induced PI-3K activation (FIG. 28D). These results indicate that SEMA3F-NRP2 interactions are regulatory to inhibit the activity of PI-3K-Akt/mTOR signaling.

Figures 29C, 29D:
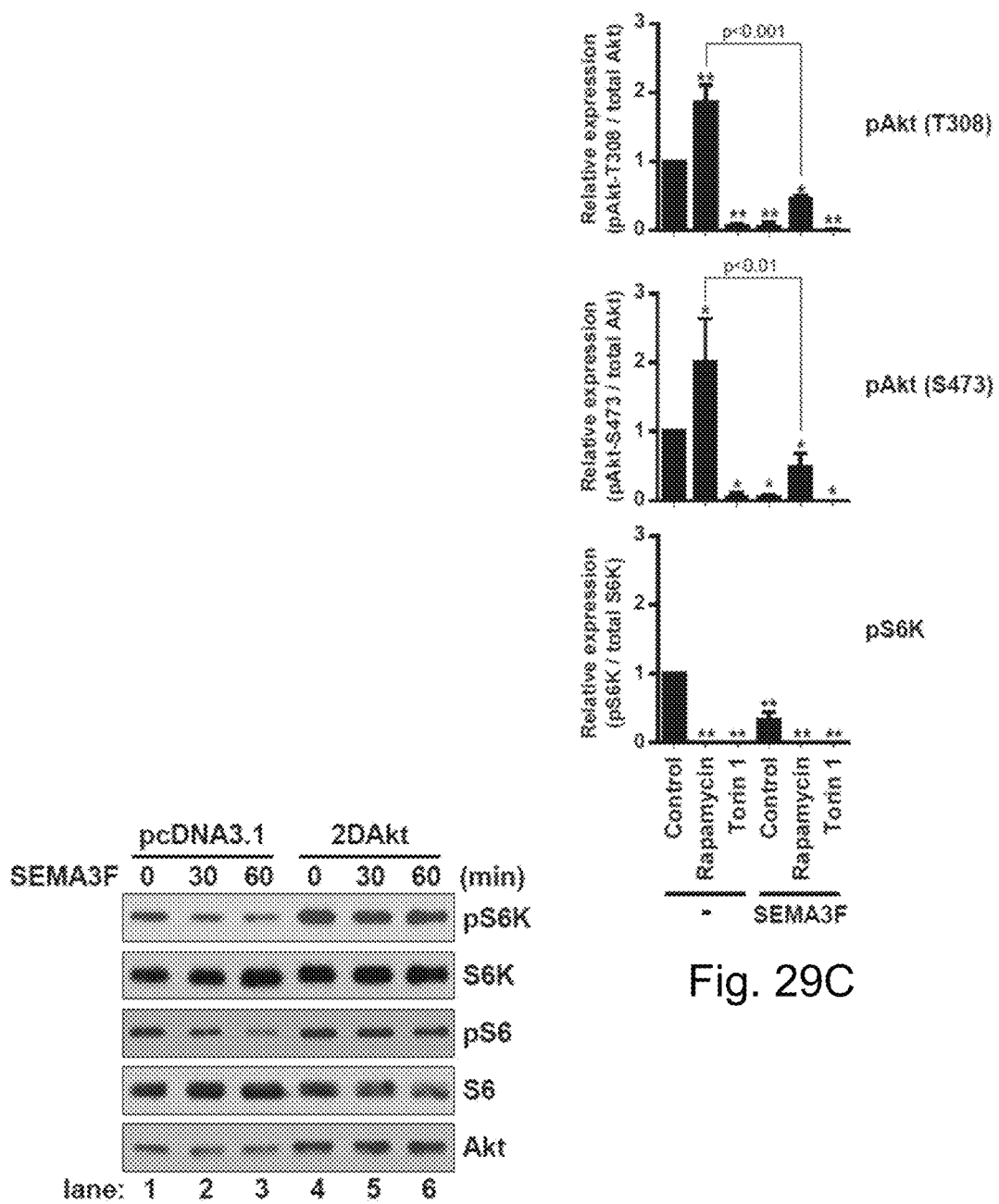

SEMA3F Primarily Inhibits the Assembly of mTORC2.

mTORC1 and mTORC2 signaling is critical for cell metabolism (30, 31) as well as the differentiation, proliferation and survival of many normal cell types (27, 32, 33, 34, 35). By immunoprecipitation, it was found that SEMA3F inhibited the association between mTOR and both raptor and rictor (FIG. 29A), suggesting a biological effect on both mTORC1 and mTORC2 respectively. Indeed, cells treated with SEMA3F for 60 minutes had reduced levels of pAkt (T308 and S473) and pS6K (vs. untreated cells, FIG. 29B, lane 1 vs. 4). To determine if its primary mode of function relates to the inhibition of mTORC1 vs. mTORC2, cells were pretreated with rapamycin (10 nM for 30 minutes to inhibit mTORC1) and subsequently the cells were cultured in the absence or presence of SEMA3F and rapamycin for another 60 minutes. Treatment with rapamycin alone (for 90 minutes) as a control resulted in a marked inhibition of pS6K, but an induction in the levels of pAkt (T308 and S473) by 1.9- ($p<0.001$) and 2.0-fold ($p<0.01$), respectively (FIG. 29B, lanes 1 vs. 2 and FIG. 29C), as previously reported (36, 37, 38). In contrast, U87MG cells that were treated with rapamycin for 30 minutes and subsequently treated with SEMA3F and rapamycin for an additional 60 minutes had reduced levels of both pAkt and pS6K (FIG. 29B, lane 2 vs. 5). Of note, this effect of SEMA3F on the inhibition of pAkt expression was similar to that observed when cells are treated with the ATP competitive mTORC1/C2 inhibitor Torin 1 (FIG. 29B, lane 3 vs. 4). SEMA3F also inhibited pSGK1 (S422) and pPKC((S657, FIG. 28B and FIG. 35A), other known targets of mTORC2 activity (23).

Figures 35A, 35B:
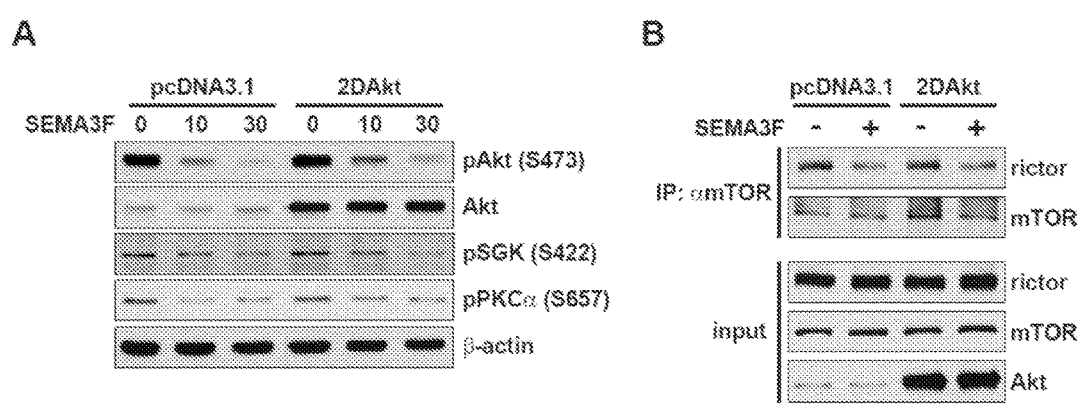
FIGS. 35A-35B depict analysis of the effect of SEMA3F on mTORC2 activity.

To further evaluate whether the primary biological effect of SEMA3F is on mTORC2 complex formation, U87MG cells were next transfected with 2DAkt, in which the T308 and S473 sites are mutated to encode a constitutively active form of the kinase (36, 37). Overexpression of 2DAkt in EC resulted in mTORC1 activation, and that rapamycin inhibited 2DAkt-induced signaling responses (37). Similarly, transfection of 2DAkt was associated with induced levels of expression of pS6K and pS6 in U87MG cells vs. control transfectants (FIG. 29D, lane 1 vs. 4), but there was no change in expression following treatment of transfected cells with SEMA3F. It was also found that SEMA3F reduced the level of pAkt (S473) in 2DAkt transfectants (FIG. 35A). Moreover, by immunoprecipitation, the treatment of 2DAkt transfected cells with SEMA3F inhibited mTOR/rictor interaction (FIG. 35B), which is consistent with its primary effect on mTORC2 assembly. Together, these results demonstrate that SEMA3F/NRP2/Plexin A1 interactions have a direct effect on the inhibition of mTORC2/Akt activity.

mTORC2 Links SEMA3F Biology with the F-Actin Cytoskeleton.

Figure 30B:
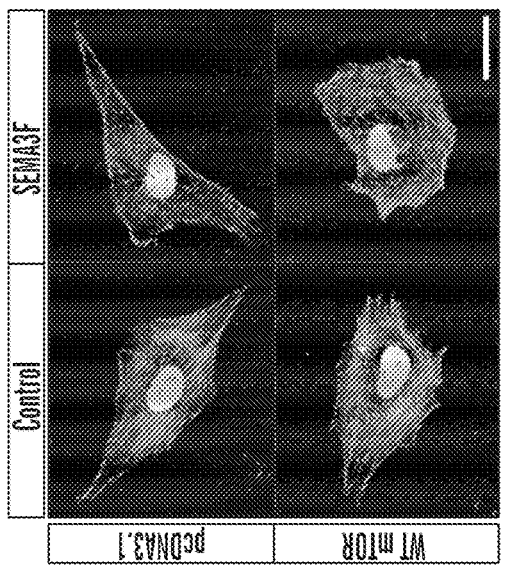
FIGS. 30A-30E show data demonstrating that mTORC2 participates in SEMA3F-induced RhoA inactivation and loss of stress fibers.
Figure 30B:
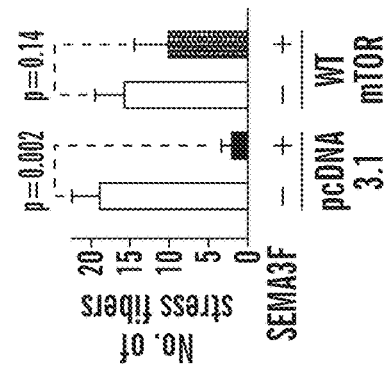
Figure 30A:
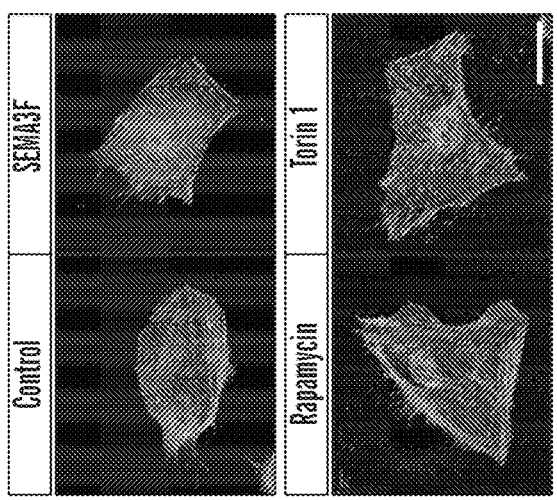
Figure 30A:
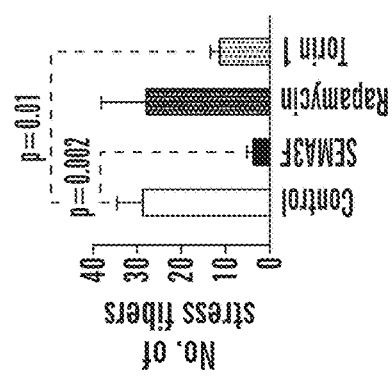
Figure 30C:
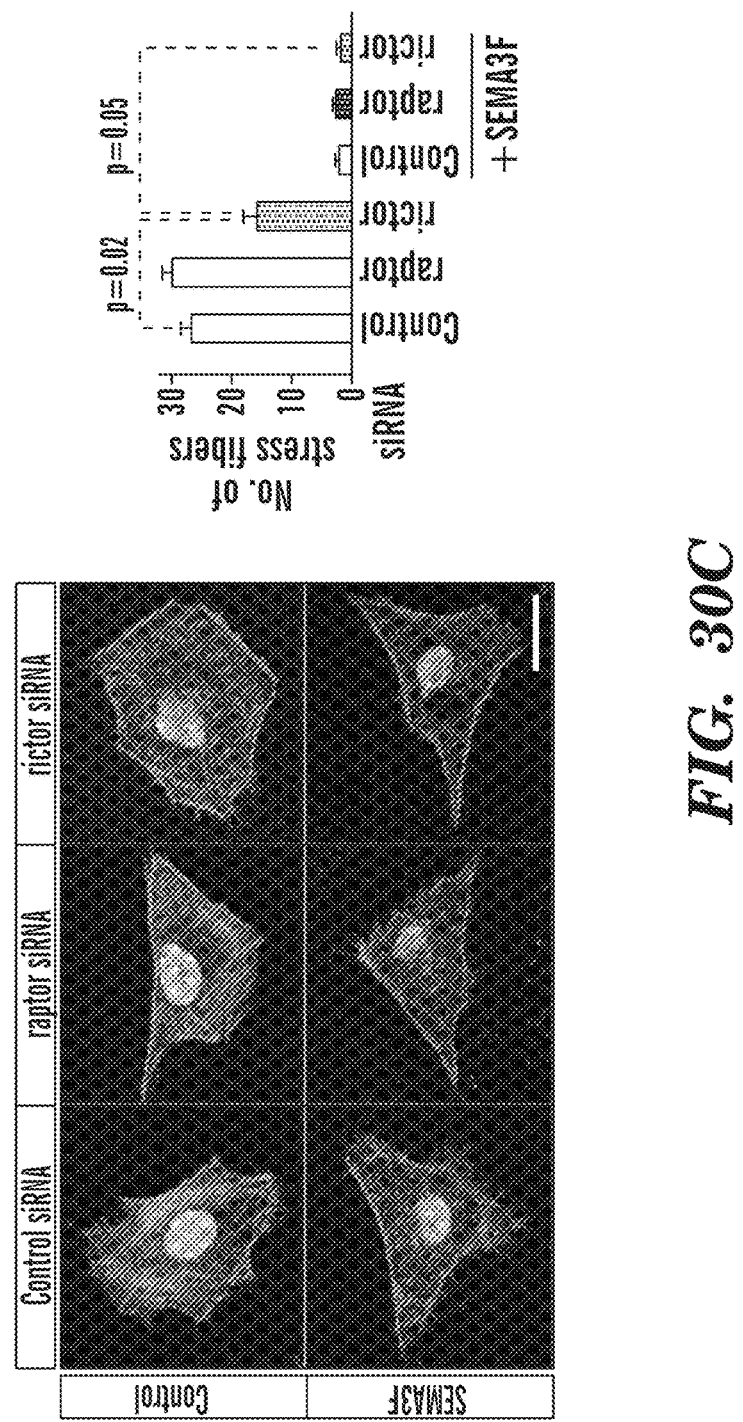

It was next determined whether the inhibition of mTORC2 serves as an intermediary response to link SEMA3F activity with cytoskeletal collapse. U87MG cells were treated either with SEMA3F (640 ng/ml), rapamycin (10 nM) or Torin 1 (10 nM) for 30 minutes and the actin cytoskeleton was visualized using phalloidin staining SEMA3F markedly inhibits stress fiber formation and cytoskeletal arrangement compared to untreated cells (FIG. 30A, p=0.002). Moreover, a similar effect was observed in cells following treatment with the mTORC1/C2 inhibitor Torin 1 (p=0.01). In contrast, treatment with the mTORC1 inhibitor rapamycin failed to elicit any cytoskeletal changes (FIG. 30A; FIGS. 35A-35B). Also, while SEMA3F inhibited stress fiber formation by 90% in pcDNA3.1 control vector transfected cells, it had minimal effects on stress fiber formation in U87MG cells transfected with an mTOR overexpression construct (FIG. 30B). These findings indicate that SEMA3F has minimal direct effects on mTORC1. Consistent with this interpretation, knockdown of raptor also had minimal effects on stress fiber formation and cytoskeleton collapse (FIG. 30C). However, SEMA3F reduced stress fiber formation in raptor-siRNA treated cells (FIG. 30C); and notably, siRNA knockdown of rictor alone was sufficient to elicit collapse (p=0.02). These data suggest that mTORC2 serves as an intermediary to modulate SEMA3F-inducible cytoskeletal collapse.

Figure 30D:
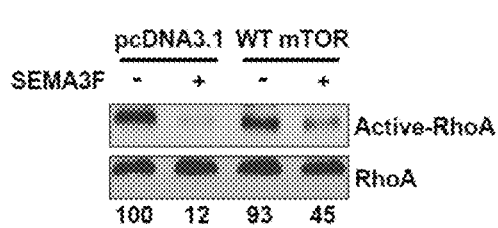
Figure 30E:
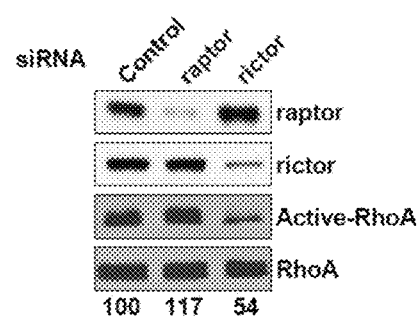

RhoA activity (39) was measured using the rhotekin pulldown assay in U87MG cells transfected with the mTOR overexpression construct (FIG. 30D). RhoA activity was suppressed by SEMA3F in control pcDNA3.1-transfected cells (by 88%), but activity was partially rescued in cells overexpressing mTOR (by 55%). In addition, using siRNAs (as above) it was found that knockdown of rictor, but not raptor, attenuated RhoA activity (FIG. 30E). Collectively, these observations demonstrate that the inhibition of mTORC2 activity by SEMA3F/NRP2/Plexin A1 interactions is functional to inactivate RhoA, which in turn leads to cytoskeleton collapse. Thus, upstream regulation of mTORC2 activity by SEMA3F has potential to target multiple biological responses.

SEMA3F Inhibits Hypoxia-Induced Production of VEGF Via the mTOR Pathway.

Figures 31A, 31B, 31C, 31D:
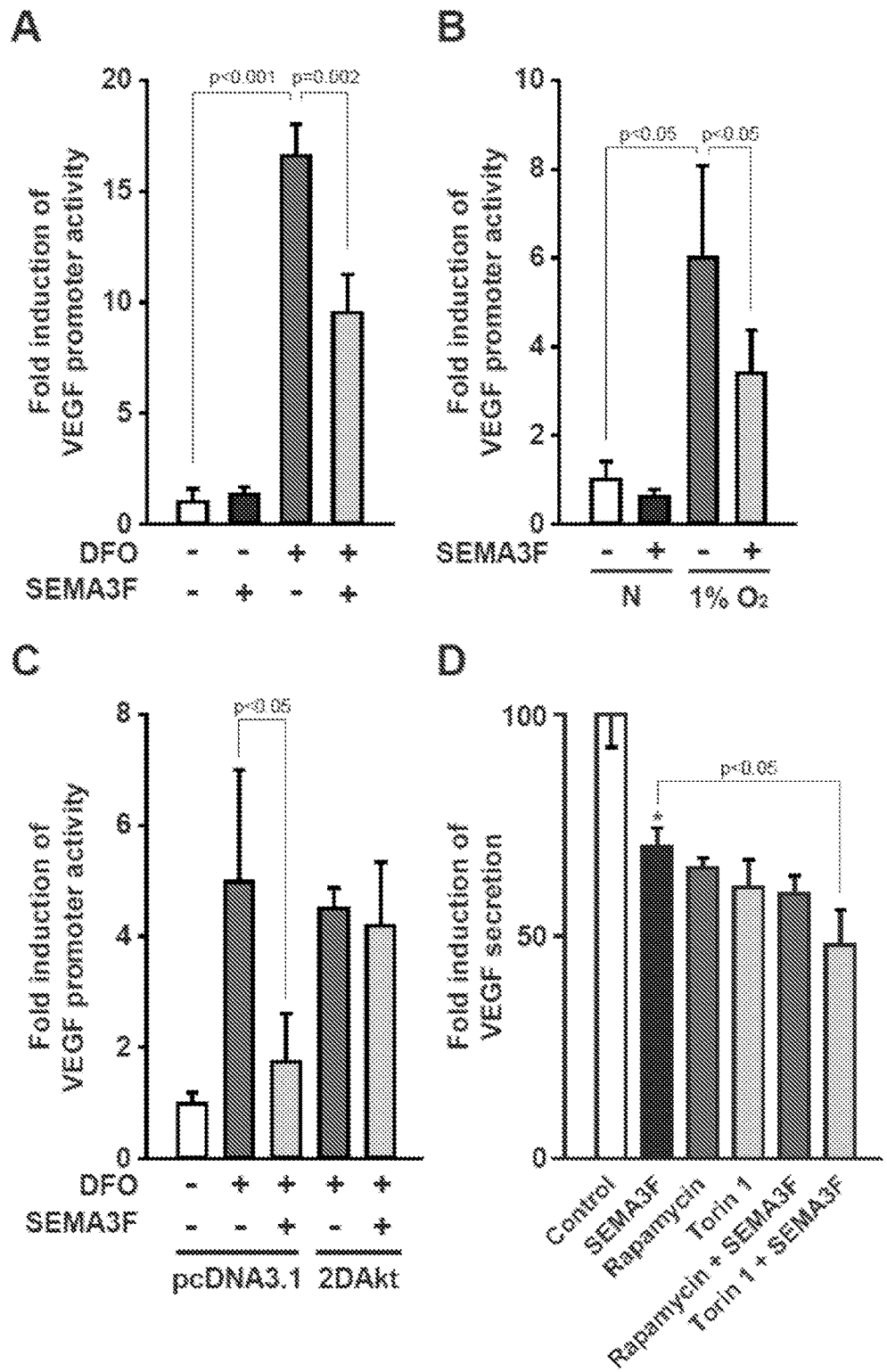
FIGS. 31A-31D show data demonstrating that SEMA3F suppresses VEGF through the inhibition of mTOR-Akt signals.

The local expression and regulation of VEGF is key to many physiological and pathological processes (40, 41). These findings indicate that SEMA3F can target the transcriptional activation of VEGF via its ability to target mTOR kinase activity (36, 42). To test the effect of SEMA3F on the regulation of VEGF expression, U87MG cells were transfected with a full-length 2.6 kb VEGF promoter-luciferase construct and exposed to the hypoxia mimetic agent desferrioxamine (DFO) or hypoxia (1% 02). It was found that treatment with DFO induced VEGF promoter activity (by 16-fold, p<0.001), which was partially inhibited (43%, p<0.005) by SEMA3F (pre-treatment for 30 minutes, FIG. 31A). VEGF promoter activity was also increased (as expected 43) following 18 hours culture in 1% 02 (FIG. 31B); again VEGF promoter activity was reduced following treatment with SEMA3F (44%, p<0.05), but not to basal levels. To test the relative effect of SEMA3F on mTORC1/C2, U87MG cells transiently co-transfected with the 2DAkt construct and the full length VEGF promoter reporter construct, and the cells cultured in the absence or presence of SEMA3F. It was found that SEMA3F failed to attenuate VEGF promoter activity in 2DAkt transfected cells following treatment with DFO (FIG. 31C). Finally, the effect of SEMA3F on the secretion of VEGF into conditioned media (by ELISA) was determined in the absence or presence of DFO. DFO markedly increased VEGF production (by 160% compared to untreated cells, p<0.001 (data not shown). Furthermore, DFO-induced VEGF protein secretion was significantly reduced by SEMA3F, the mTORC1 inhibitor rapamycin (for 18 hours to target mTORC1/C2) and by the mTORC1/C2 inhibitor Torin 1 (FIG. 31D, p<0.01). Concomitant treatment of the cells with rapamycin and SEMA3F failed to further suppress VEGF production, but the combination of SEMA3F and Torin 1 slightly (but significantly p<0.05) inhibited VEGF levels as compared to SEMA3F or Torin 1 alone (FIG. 31D). Collectively, these findings indicate that SEMA3F suppresses inducible VEGF expression in part via the regulation of mTOR activity.

SEMA3F Inhibits U87MG Tumor Growth and Angiogenesis In Vivo.

Figures 32A, 32B, 32C, 32D, 32E:
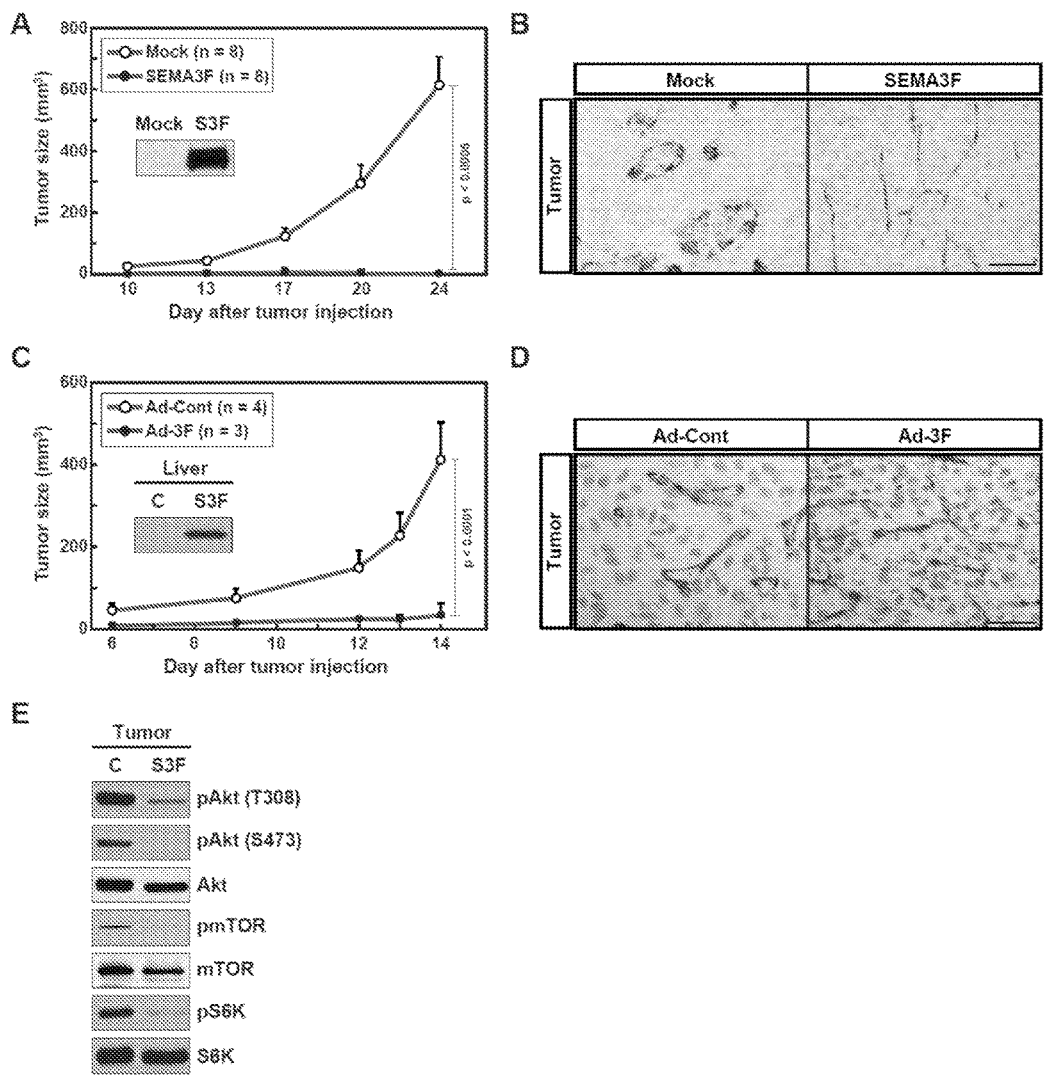
FIGS. 32A-32E show data demonstrating that SEMA3F inhibits human tumor growth in xenografts in vivo.

To determine the in vivo relevance of our signaling studies, the effect of SEMA3F on tumor growth was evaluated in a well-established xenograft model (5, 44, 45). In one approach, parental U87MG cells or U87MG cells that were engineered to constitutively overexpress SEMA3F were implanted subcutaneously into nude mice ($1 \times 10^6$/mouse); tumor size (mm$^3$) was measured at the indicated time points over a period of 3 weeks. It was found that tumor growth was essentially absent when SEMA3F-producing cells were implanted vs. parental cells (p<0.0005, FIG. 32A). Furthermore, immunohistochemical analysis of CD31-expressing EC demonstrated numerous blood vessels in parental U87MG tumors (FIG. 32B); in contrast, capillaries within the U87MG/SEMA3F-derived tumors were constricted and were without discernable lumens (FIG. 32B). A second approach involved the injection of $1 \times 10^6$ U87MG cells into the skin of nude mice, and after 2 days the mice received a single intravenous injection of adenovirus encoding human SEMA3F tagged with His (Ad-3F) or a control adenovirus (Ad-Cont). Injection of Ad-3F ($1 \times 10^9$ pfu) into mice did not result in any toxicity over a 30-day period; mice gained weight and typical behavior was normal. Western blot analysis showed that the administration of Ad-3F resulted in high levels of SEMA3F production in the liver (FIG. 32C), and by ELISA, SEMA3F levels were measurable in the serum. Circulating serum levels of SEMA3F protein peaked on day 8 following administration of adenovirus (day 10 post injection of tumor cells), and persisted until the end of the experiment on day 14 (average of 26 ng/ml, n=4). Thus, this approach enables circulating SEMA3F production to begin at a time after tumor growth has been established in the mouse. Tumor volume reached 400 mm$^3$ by day 14 in Ad-Cont-treated mice, whereas tumor growth was minimal over a 14 day period in mice injected with Ad-3F (p<0.0001, FIG. 32C). By immunostaining, there was a striking collapsed phenotype of CD31-expressing capillaries within tumors harvested from Ad-3F-treated mice and most blood vessel lumens did not appear patent (FIG. 32D). Furthermore, by Western blot analysis, it was found that pAkt, pmTOR and pS6K levels were suppressed in tumors following treatment with Ad-3F, as compared to Ad-Cont treated mice (FIG. 32E). Thus, in two very different approaches, SEMA3F administration (local and/or systemic) has similar anti-tumor effects. Together, these results demonstrate that SEMA3F inhibits tumor growth and angiogenesis by inhibiting the Akt/mTOR signaling pathway.

DISCUSSION

Semaphorins were first shown to be mediators of axon guidance and pathfinding and they were subsequently found to regulate vascular homeostasis and tumor development (1, 2). In these studies, SEMA3F is defined as a potent mTOR inhibitor, and its effect is mediated through the inhibition of PI-3K activity and the assembly of mTOR/rictor and mTOR/raptor complexes. It is also found that its functional effect is mediated via interactions with the NRP2-Plexin A1 receptors. The regulation of mTOR by SEMA3F was found in several cell types, including T cells, endothelial cells and tumor cell lines, all of which are well established to utilize this signaling pathway for cellular activation, differentiation and proliferation. These findings indicate that SEMA3F biology is of broad relevance in many physiological and pathological conditions, including cancer and diseases associated with chronic inflammation such as allograft rejection.

While much is known about the intracellular regulation of mTORC1, relatively little is known about the upstream regulation of mTORC2 activity. In *C. elegans*, it has been shown that invertebrate semaphorin-plexin interactions reduce the association of TOR with rictor but promote TOR/raptor association, resulting in mRNA translation through the 4EBP-eIF4F pathway 14. In contrast, in mammalian cells, the presently presented studies indicate that SEMA3F can serve as a unique soluble ligand to selectively target mTORC2 activity and thus, pro-resolution following cellular activation. For example, transfection of NRP2-expressing cell lines with 2DAkt to activate mTORC1 demonstrated that SEMA3F had minimal effects on the association between mTOR and raptor (data not shown) or the phosphorylation/activation of S6K and S6. In addition, SEMA3F responses were notably different than those observed following a short timecourse treatment with rapamycin, which is known to primarily target mTORC1. In contrast, in several assays, it was found that the inhibitory effects of SEMA3F on cellular activation and cytoskeletal collapse were primarily mediated through its effect on mTORC2 and were similar to those observed following treatment with Torin 1 (a pharmacological inhibitor of mTORC1/C2).

Figures 36A, 36B, 36C, 36D, 36E:
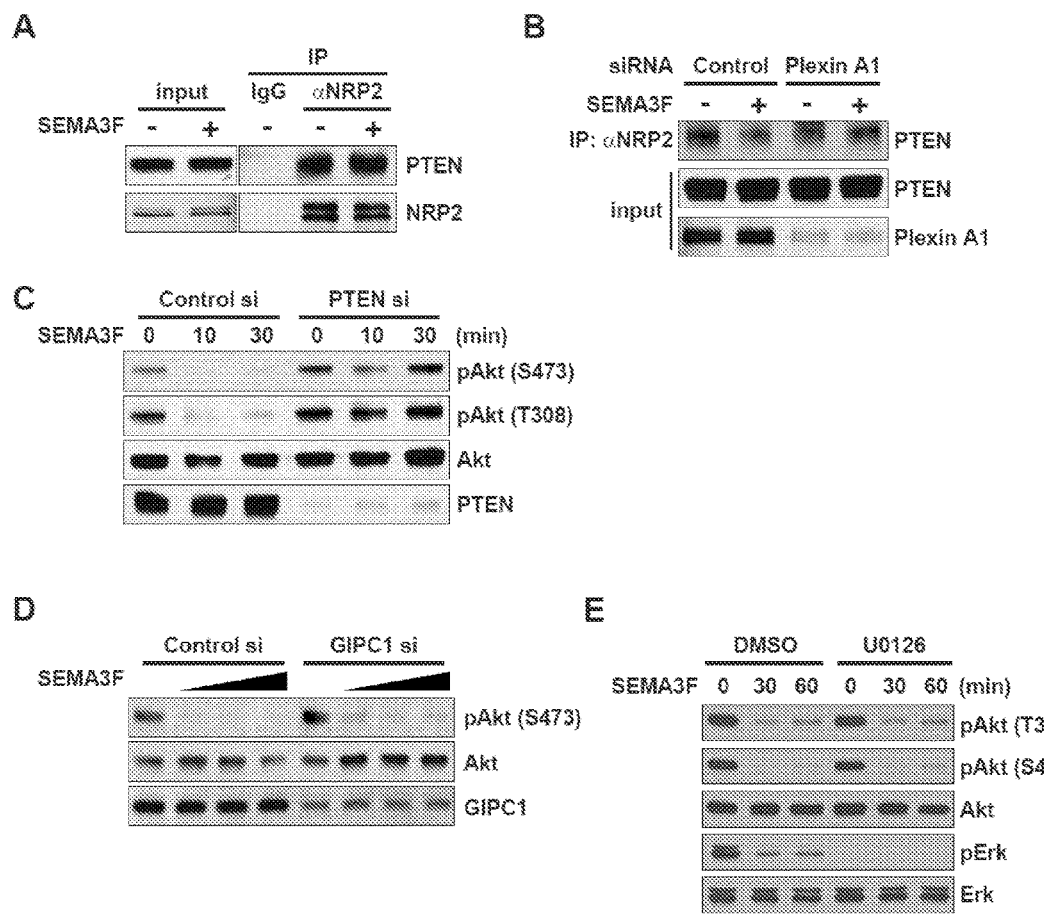
FIG. 36A depicts a western blot. HUVEC were treated with SEMA3F (1800 ng/ml) for 30 minutes and were subjected to immunoprecipitation and Western blot analyses with anti-NRP2 and -PTEN as illustrated.
FIG. 36B depicts a western blot. HUVEC were transfected with control-, or Plexin A1-specific siRNAs (20 nM), prior to SEMA3F treatment (1800 ng/ml); lysates were subjected to immunoprecipitation and Western blot analyses with anti-NRP2 and anti-PTEN as illustrated.
FIG. 36C depicts a western blot. HUVEC were transfected with control-, or PTEN-specific siRNAs (20 nM), prior to SEMA3F treatment (1800 ng/ml); lysates were analyzed by Western blot.
FIG. 36D depicts a western blot. U87MG cells were transfected with control or GIPC1-specific siRNA (20 nM). After 48 hours, cells were treated with SEMA3F (200, 600, 1800 ng/ml, from left to right) for 30 minutes, and were analyzed by Western blot.
FIG. 36E depicts a western blot. U87MG cells were treated with U0126 (10 µM) for 30 minutes prior to combination with 30 minutes and 60 minutes of SEMA3F (640 ng/ml). Akt and MAPK signaling was analyzed by Western blot. All data presented are representative of 3 independent experiments.

Importantly, it was also found that SEMA3F reduced PI-3K activity which is reported to function in the activation of mTORC246, 47. It is thus likely that SEMA3F inactivates mTORC2 via upstream inhibition of PI-3K. Another related family member NRP1 binds and activates phosphatase and tensin homologue deleted on chromosome ten (PTEN) (7), a negative regulator of PI-3K. Without wishing to be bound by theory, it thus postulated that the ligation of NRP2 by SEMA3F can result in the recruitment of PTEN, which in turn serves as an intermediary to regulate PI-3K activity. Consistent with this possibility, it was found that PTEN coimmunoprecipitated with NRP2 in human umbilical vein EC (HUVEC, FIG. 36A). Moreover, following siRNA transfection and knockdown of Plexin A1, by immunoprecipitation, PTEN maintained association with NRP2 (FIG. 36B), suggesting a direct interaction between PTEN and NRP2 (and not Plexin A1) in HUVEC. Furthermore, SEMA3F failed to inhibit pAkt expression following siRNA knockdown of PTEN in HUVEC (FIG. 36C). These findings are most suggestive that the recruitment of PTEN to NRP2 is mechanistic for its regulatory effects on PI-3K/Akt/mTOR signaling.

However, U87MG, U251 and Jurkat cells are reported to be relatively PTEN deficient (48, 49, 50) (see FIG. 34C), indicating that SEMA3F may also elicit its regulatory response(s) via PTEN-independent mechanisms. Indeed, as expected, PTEN failed to co-immunoprecipitate with NRP2 in U87MG cells (data not shown). To this end, other adaptors with potential to mechanistically link NRP2 signals with PI-3K activity were screened. These include GIPC1 (GAIP/RGS19-interacting protein, also known as neuropilin-interacting protein or synectin, FIG. 36D) (51, 52, 53), other GIPC family members(52) and DEP domain containing mTOR interacting protein (DEPTOR) (32, 54). However, siRNA knockdown of these adaptors did not alter the regulatory effect of SEMA3F on pAkt expression (data not shown). Crosstalk between the effects of SEMA3F on mTOR/Akt and MAPK signaling were evaluated. The pharmacological MEK inhibitor U0126 did not modulate the regulatory effects of SEMA3F on levels of pAkt, indicating that the inhibitory effect of SEMA3F on Akt-mTOR signaling is MAPKindependent (FIG. 36E). Thus, while SEMA3F-NRP2 interactions may recruit PTEN to regulate PI-3K and mTORC2 in primary cultures of normal cells, additional adaptors/kinases may also function in this response.

Figure 33:
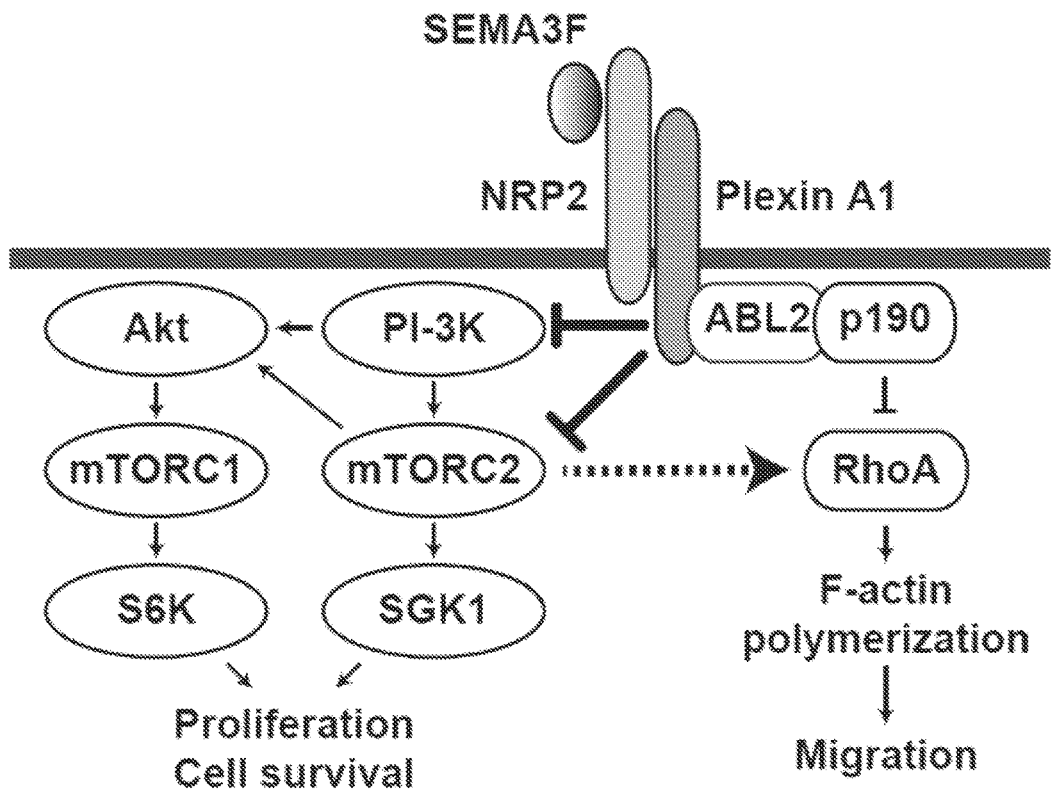
FIG. 33 depicts a schematic cartoon showing regulatory signaling pathways mediated by SEMA3F-NRP2/Plexin A1 interactions. SEMA3F binds to the NRP2-Plexin A1 complex and associates with PTEN to inactivate PI-3K and mTORC2/Akt-dependent signaling. Receptor-mediated signals may also inactivate mTORC2/Akt signaling via PTEN independent mechanisms in tumor cell lines. Functionally, these regulatory/proresolution signals suppress cell proliferation, migration, cytoskeletal stress fiber rearrangement and cell survival. SEMA3F also inhibits cytoskeleton structure in part by inactivating RhoA through both the ABL2 kinase and p190RhoGAP6; the current studies show that the inactivation of RhoA and cytoskeletal stress fiber rearrangement is also mediated via the inhibition of mTORC2.

The semaphorin family of axonal guidance molecules, including SEMA3F, are well established to promote neuronal growth cone collapse that results from concomitant rearrangement of actin cytoskeletal stress fibers. SEMA3F is a potent inhibitor of tumor cell and EC adhesion, spreading and motility in vitro and in vivo(5, 6). In addition, SEMA3F does not induce apoptosis in U87MG cells within 24 hours6. In tumor and vascular endothelial cells, SEMA3F inactivates RhoA, thereby inhibiting cytoskeletal stress fiber formation6, 12. It is demonstrated herein that mTORC2 is an intermediary in this response, and is indispensable for RhoA inactivation. For example, SEMA3F treatment results in cell collapse following transfection of cells with mTOR (to induce mTORC1), suggesting that this effect is either mTOR-independent and/or is associated with targeting of mTORC2. Consistent with an effect on mTORC2, siRNA knockdown of rictor and the treatment of U87MG cells with the mTORC2 inhibitor Torin 1 consistently reduced the number of stress fibers as observed following treatment with SEMA3F. Furthermore, SEMA3F reduced the number of stress fibers in raptor siRNA (mTORC1) knockdown cells. Importantly, SEMA3F further reduced stress fibers in rictor siRNA treated cells, indicating that SEMA3F likely inactivates RhoA in part via mTORC2 and in part via the ABL2/p190RhoGAP pathway (FIG. 33). Although mTORC2 is reported to interact with the Rho GTPase family and mediate F-actin cytoskeleton re-organization (18, 55), it is demonstrated herein that this effect can be targeted through stimulation of NRP2-induced signals.

mTORC2-dependent activation of Akt functions in the transcriptional activation of VEGF in endothelial cells (36). VEGF functions as a proangiogenesis factor to augment tumor growth, and as a leukocyte chemoattractant in association with chronic inflammation (43). Since SEMA3F targets mTORC2 activity, it was also assessed whether it has any biological impact on the inducible expression of VEGF. It was found that SEMA3F markedly inhibits inducible VEGF expression via the inhibition of both mTORC2 and mTORC1. However, SEMA3F fails to inhibit the transactivation of VEGF following transfection of cells with the 2DAkt construct which induces mTORC1 activation. It was also found that treatment with either SEMA3F or rapamycin (long-term treatment to inhibit both mTORC1/C2) or the mTORC1/C2 inhibitor Torin 1 results in a similar level of inhibition of VEGF expression in U87MG cells. There was no additional inhibitory effect of combined SEMA3F and rapamycin, suggesting that SEMA3F and rapamycin target the same signaling pathway. However, surprisingly SEMA3F partially augmented the inhibitory effect of Torin 1 on VEGF expression. This may suggest that the Torin 1 dose used in these studies was not sufficient to completely inhibit mTORC2, or alternatively, it is possible that Torin 1 uncovers additional SEMA3F-elicited regulatory mechanism(s). Of note, SEMA3F alone fails to inhibit VEGF expression to basal levels, yet it has been previously reported to inhibit VEGFinduced proliferation of EC (56). Nevertheless these new findings suggest that this anti-VEGF effect of SEMA3F may be most significant for its biological effects in vivo, such as our past (5, 6) and current observations of its tumor growth inhibitory potential.

Overexpression of SEMA3F in tumor cells, such as lung, brain and breast cancer cells, significantly inhibits tumor development and angiogenesis in xenograft mouse models (5, 13, 44, 45, 57). In these studies, control or SEMA3F-producing U87MG cells were implanted subcutaneously into nude mice and it was found that the expression of SEMA3F strongly inhibited tumor growth and angiogenesis. Furthermore, an adenovirus was used to evaluate the effects of high levels of circulating SEMA3F protein on tumor growth and angiogenesis after tumors have developed. Most notably, circulating SEMA3F markedly inhibited tumor growth. However, all neoangiogenic blood vessels within the growing tumors had a dramatic collapsed phenotype, which is consistent with known SEMA3F effects on the cytoskeleton (6). In addition, lysates of tumors from SEMA3F-treated mice showed diminished levels of pAkt, pmTOR and pS6K, which is consistent with its effects in vitro. Therefore, in the in vivo models, SEMA3F is likely to have large impact on tumor growth via both the suppression of VEGF secretion and direct inhibition of Akt-mTOR signaling within tumors, as well as via effect on endothelial cells that inhibit angiogenesis. Also, the marked inhibition of tumor growth obtained by two different approaches (local overexpression by the tumor and by systemic administration) confirms that SEMA3F is a potent mTOR inhibitor in vivo.

These findings demonstrate that SEMA3F-NRP2 interactions inhibit intracellular PI-3K activity, mTORC2-dependent signaling, RhoA activity and cytoskeletal stress fiber formation. SEMA3F also inhibits the inducible expression of VEGF at both the transcriptional and protein level in vitro, and it has powerful antitumor effects in vivo. SEMA3F is a secreted physiological mTOR inhibitor that functions to promote resolution following cellular activation. These findings have broad clinical implications, including the use of SEMA3F for therapeutic purposes, for instance, to target chronic immune-mediated diseases, allograft rejection or angiogenesis related pathology, such as tumor growth and progression.

Methods

Antibodies and Reagents:

The antibodies, rabbit monoclonal anti-phospho-Akt (Thr308) antibody (#2965); mouse monoclonal anti-phospho-Akt (Ser473) antibody (#4051); rabbit polyclonal anti-Akt antibody (#9272); rabbit polyclonal anti-phospho-Erk1/2 (Thr202/Tyr204) antibody (#9101); mouse monoclonal anti-Erk1/2 antibody (#4696); rabbit monoclonal anti-phospho-S6K (Thr389) antibody (#9234); rabbit monoclonal anti-S6K antibody (#2708); rabbit monoclonal anti-phospho-S6 (Ser235/236) antibody (#4856); mouse monoclonal anti-S6 antibody (#2317); rabbit monoclonal anti-phosphomTOR (Ser2448) antibody (#5536); rabbit polyclonal anti-mTOR antibody (#2972); rabbit polyclonal anti-plexin A1 antibody (#3813); rabbit monoclonal anti-raptor antibody (#2280); rabbit monoclonal anti-RhoA antibody (#2117); rabbit monoclonal anti-PTEN antibody (#9188) were all purchased from Cell Signaling Technology (Danvers, Mass.). Goat polyclonal anti-phospho-SGK (S422, sc-16745); mouse monoclonal anti-NRP2 antibody (C-9, sc-13117); goat polyclonal anti-GIPC antibody (N-19, sc-9648) were purchased from Santa Cruz Biotechnology, Inc (Dallas, Tex.). Rabbit polyclonal anti-rictor antibody (A300-458A) was purchased from Bethyl Laboratories, Inc (Montgomery, Tex.), and mouse monoclonal anti-β-actin antibody (AC-15) was from Sigma-Aldrich (St. Louis, Mo.).

The VEGF-A (DVE00) ELISA kit was obtained from R&D Systems (Minneapolis, Minn.). The PI3-Kinase Activity ELISA (K-1000s) was purchased from Echelon Biosciences (Salt Lake City, Utah). The mTOR inhibitors, rapamycin and Torin 1, were purchased from Lc Laboratories (Woburn, Mass.) and R&D Systems, respectively. Desferrioxamine (DFO) was purchased from Sigma-Aldrich, and the MEK inhibitor (U0126) was purchased from EMD-Millipore (Billerica, Mass.). pGL4.74[hRluc/TK] vector (Promega Madison, Wis.) was used as an internal control in luciferase assay.

Cell Culture:

U87MG and U251 human glioblastoma cells, kidney 293 cells and 293T cells, and Jurkat T lymphocytes were obtained from American Type Culture Collection (ATCC, Manassas, Va.) and cultured in media containing 10% FBS (Denville Scientific, Inc., South Plainfield, N.J.) and 1% L-glutamine/penicillin G/streptomycin sulfate (1% GPS, Life Technologies) as recommended. HUVECs were purchased from Lonza (Walkersville, Md.) and cultured in EBM2 medium supplemented with EGM2 SingleQuot. Human melanocytes (HEMn-LP, Life Technologies) were maintained with Medium 254 supplemented with Human Melanocyte Growth Supplement (Life Technologies) in a 5% CO2 incubator at 37° C. For all hypoxia experiments, cells were cultured in a hypoxic chamber (Heracell, Thermo Scientific, Hudson, N.H.) in 1% O2 at 37° C.

Human Recombinant SEMA3F:

A full-length, His-Myc-tagged human SEMA3F construct was transfected into 293T cells using FuGENE HD Transfection Reagent (Roche, Basel, Switzerland). SEMA3F secreted into culture medium was purified on HiTrap™ HP Chelating columns (GE Healthcare Bio-Sciences Corp., Pittsburgh, Pa.) (60).

Phospho-Kinase Array:

The Human Phospho-Kinase Array Kit (ARY003) was obtained from R&D Systems. U87MG cells were treated with SEMA3F which was previously found to induce cytoskeletal collapse and inhibit RhoA activity (6). U87MG cells were previously treated with SEMA3F at 320 ng/ml which was found to induce morphological changes and inhibit cell migration in U87MG cell and HUVEC. Consistent with these results, we find that SEMA3F (even at the lowest concentration 200 ng/ml) inhibits pAkt and pS6K signaling (FIG. 34D). However, in other cell types, this concentration was found to be suboptimal to suppress these signals. Thus, a concentration at 640 ng/ml was optimized to analyze SEMA3F signaling pathways. Cell lysates were collected at 30 minutes after SEMA3F treatment and the levels of phosphoproteins were analyzed with this array, according to the manufacturer's instructions.

Western Blotting:

Proteins within each sample were separated by SDS-PAGE and transferred to nitrocellulose membranes. The membranes were blocked with 4% skimmed milk in TBS-T (0.1% Tween 20 in tris-buffered saline [TBS]) for 30 minutes, followed by incubation with the primary antibody. After washing with TBS-T, membranes were incubated with the appropriate horseradish peroxidase-conjugated secondary antibody, and immunoreactivity was detected by using ECL detection reagents.

Immunoprecipitation:

Cell lysates were immunoprecipitated using an appropriate antibody at 4° C. overnight. Protein G-Sepharose 4 Fast Flow beads (GE Healthcare) were added to each sample, followed by mixing for 1 hour at 4° C. The samples were dissolved in SDS sample buffer and boiled for 5 minutes.

F-Actin Staining:

Cells were fixed with 4% paraformaldehyde (PFA) followed by permeabilization with 0.2% Triton X-100 in PBS. F-actin and nuclei were stained with Alexa Fluor 488 phalloidin and Hoechst 33342, respectively. Confocal images from 3-5 areas of each culture were reviewed and stress fibers were counted in representative individual cells (~5/experiment) using standard methodology as described6.

RhoA Activity:

RhoA activity assays were measured by using the RhoA activation assay kit based on rhotekin pull-down, according to the manufacturer's instructions (Cytoskeleton, Denver, Colo.).

RNA Interference:

Transfection of siRNA (20 nM) was performed with siLentFect Lipid Reagent (Bio-Rad, Hercules, Calif.), according to the manufacturer's protocol. Control siRNA (Silencer Negative Control #2 siRNA) was purchased from Life Technologies. ON-TARGETplus™ Human NRP2 siRNA was purchased from Thermo Scientific (Hudson, N.H.), Plexin A1 (Hs_PLXNA1_3), rictor (Hs_RICTOR_5), PTEN (Hs_PTEN_6) and GIPC1 (Hs_RGS19IP1_1) siRNA from Qiagen (Valencia, Calif.), and Raptor siRNA (sc-44069) from Santa Cruz Biotechnology, Inc. (Dallas, Tex.). In general, siRNA transfection was performed for 48 hours prior to assays.

Transfection and Luciferase Assay:

U87MG cells were transiently transfected with plasmid constructs (pcDNA3.1, WT mTOR, 2DAkt, VEGF luciferase reporter plasmid or pGL4.74[hRluc/TK]) as indicated using Lipofectamine 2000 reagent (Life Technologies) according to the manufacturer's instructions. After 18 hours, cells were treated as outlined in each experimental design. VEGF promoter activity was analyzed using a Dual-Luciferase Reporter Assay System (Promega), and luciferase activity was normalized by Renilla luciferase as an internal control.

Adenovirus:

Recombinant control (#000047A) and human SEMA3F-His (#129755A) adenovirus were purchased from Applied Biological Materials, Inc. (Richmond, Canada). Each adenovirus was amplified with 293 cells and purified using the Fast Trap Adenovirus Purification and Concentration Kit (EMD-Millipore). The adenovirus titer was determined by Adeno-X™ Rapid Titer Kit (Clontech Laboratories, Inc., Mountain View, Calif.). Adenovirus was obtained at titers greater than $1 \times 10^{10}$ pfu/ml.

Tumor Xenograft Model:

Parental U87MG cells or human SEMA3F stable U87MG clones (1×106/injection) were administrated into nude mice (male, 8-10 weeks of age) subcutaneously. In one model, tumor size was measured every 3-4 days using a standard calipers. Mice were sacrificed on day 24 and tumors were removed. In a second model, parental U87MG cells were administrated into nude mice subcutaneously. In pilot studies, adenovirus encoding SEMA3F (Ad-3F) or a control adenovirus (Ad-Cont) was injected intravenously via the tail vein 3 days prior to tumor cell injection ($1 \times 10^6$ U87MG cells/injection); we observed that all tumors in the Ad-3F group failed to grow (data not shown). Thus, we revised our approach, and administration of Ad-3F was delayed until day 2 after the tumor injection, so that tumor growth was initiated prior to peak SEMA3F production in the circulation (~day 8-10 post administration, data not shown). Tumor size was measured every other day using a standard calipers, serum samples were collected from the tail vein at day 5 and 8 and mice were sacrificed on day 14 when the tumor, the liver and serum samples were collected. Production of SEMA3F was confirmed by Western blot analysis of liver with anti-His/anti-SEMA3F antibodies and by analysis of serum level of SEMA3F using the human SEMA3F ELISA kit (MBS454602) from MyBioSource (San Diego, Calif.).

Immunohistochemistry:

Paraffin-embedded sections were deparaffinized and activated with proteinase K (36 µg/ml) in 0.2 M Tris buffer (pH7.2) at 37° C. for 30 minutes and processed for immunohistochemical staining Immunohistochemistry was performed with anti-mouse CD31 antibody (BD Biosciences, San Jose, Calif.), the VectaStain Kit (Vector, Burlingame, Calif.) and the Tyramide Signal Amplification (TSA) Biotin system (NEN Life Science Products, Boston, Mass.), according to the manufacturer's instructions.

Statistical Analysis:

All assays were independently performed at least three times. The results are represented as mean±standard deviation (SD). Groups were compared using the Student's t test and p values <0.05 were considered statistically significant.

REFERENCES

1. Klagsbrun M, Eichmann A A role for axon guidance receptors and ligands in blood vessel development and tumor angiogenesis. *Cytokine & growth factor reviews* 16, 535-548 (2005).
2. Neufeld G, Kessler O. The semaphorins: versatile regulators of tumour progression and tumour angiogenesis. *Nature reviews Cancer* 8, 632-645 (2008).
3. Giger R J, Urquhart E R, Gillespie S K, Levengood D V, Ginty D D, Kolodkin A L. Neuropilin-2 is a receptor for semaphorin IV: insight into the structural basis of receptor function and specificity. *Neuron* 21, 1079-1092 (1998).
4. Takahashi T, Strittmatter S M. Plexin: autoinhibition by the plexin sema domain. *Neuron* 29, 429-439 (2001).
5. Bielenberg D R, et al. Semaphorin 3F, a chemorepulsant for endothelial cells, induces a poorly vascularized, encapsulated, nonmetastatic tumor phenotype. *The Journal of clinical investigation* 114, 1260-1271 (2004).
6. Shimizu A, et al. ABL2/ARG tyrosine kinase mediates SEMA3F-induced RhoA inactivation and cytoskeleton collapse in human glioma cells. *The Journal of biological chemistry* 283, 27230-27238 (2008).
7. Delgoffe G M, et al. Stability and function of regulatory T cells is maintained by a neuropilin-1-semaphorin-4a axis. *Nature* 501, 252-256 (2013).

8. Hansen W, et al. Neuropilin 1 deficiency on CD4+Foxp3+ regulatory T cells impairs mouse melanoma growth. *The Journal of experimental medicine* 209, 2001-2016 (2012).
9. Kumanogoh A, Kikutani H Immunological functions of the neuropilins and plexins as receptors for semaphorins. *Nature reviews Immunology* 13, 802-814 (2013).
10. Weiss J M, et al. Neuropilin 1 is expressed on thymus-derived natural regulatory T cells, but not mucosa-generated induced Foxp3+ T reg cells. *The Journal of experimental medicine* 209, 1723-1742, s1721 (2012).
11. Bielenberg D R, et al. Increased smooth muscle contractility in mice deficient for neuropilin 2. *The American journal of pathology* 181, 548-559 (2012).
12. Procaccia V, Nakayama H, Shimizu A, Klagsbrun M. Gleevec/imatinib, an ABL2 kinase inhibitor, protects tumor and endothelial cells from semaphorin-induced cytoskeleton collapse and loss of cell motility. *Biochemical and biophysical research communications* 448, 134-138 (2014).
13. Potiron V A, et al. *Semaphorin SEMA3F affects multiple signaling pathways in lung cancer cells. Cancer research* 67, 8708-8715 (2007).
14. Nukazuka A, Tamaki S, Matsumoto K, Oda Y, Fujisawa H, Takagi S. A shift of the TOR adaptor from Rictor towards Raptor by semaphorin in *C. elegans. Nature communications* 2, 484 (2011).
15. Kim D H, et al. mTOR interacts with raptor to form a nutrient-sensitive complex that signals to the cell growth machinery. *Cell* 110, 163-175 (2002).
16. Sancak Y, et al. PRAS40 is an insulin-regulated inhibitor of the mTORC1 protein kinase. *Molecular cell* 25, 903-915 (2007).
17. Pearce L R, et al. Identification of Protor as a novel Rictor-binding component of mTOR complex-2. *The Biochemical journal* 405, 513-522 (2007).
18. Sarbassov D D, et al. Rictor, a novel binding partner of mTOR, defines a rapamycin-insensitive and raptor-independent pathway that regulates the cytoskeleton. *Current biology: CB* 14, 1296-1302 (2004).
19. Yang Q, Inoki K, Ikenoue T, Guan K L. Identification of Sin1 as an essential TORC2 component required for complex formation and kinase activity. *Genes & development* 20, 2820-2832 (2006).
20. Sarbassov D D, Ali S M, Sabatini D M. Growing roles for the mTOR pathway. *Current opinion in cell biology* 17, 596-603 (2005).
21. Wullschleger S, Loewith R, Hall M N. TOR signaling in growth and metabolism. *Cell* 124, 471-484 (2006).
22. Sarbassov D D, Guertin D A, Ali S M, Sabatini D M. Phosphorylation and regulation of Akt/PKB by the rictor-mTOR complex. *Science* (New York, N.Y.) 307, 1098-1101 (2005).
23. Garcia-Martinez J M, Alessi D R. mTOR complex 2 (mTORC2) controls hydrophobic motif phosphorylation and activation of serum- and glucocorticoidinduced protein kinase 1 (SGK1). *The Biochemical journal* 416, 375-385 (2008).
24. Dormond O, Dufour M, Seto T, Bruneau S, Briscoe D M. Targeting the intragraft microenvironment and the development of chronic allograft rejection. *Human immunology* 73, 1261-1268 (2012).
25. Gamper C J, Powell J D. All PI3Kinase signaling is not mTOR: dissecting mTORdependent and independent signaling pathways in T cells. *Frontiers in immunology* 3, 312 (2012).
26. Powell J D, Delgoffe G M. The mammalian target of rapamycin: linking T cell differentiation, function, and metabolism. *Immunity* 33, 301-311 (2010).
27. Phung T L, et al. Pathological angiogenesis is induced by sustained Akt signaling and inhibited by rapamycin. *Cancer cell* 10, 159-170 (2006).
28. Mendes-da-Cruz D A, et al. Semaphorin 3F and neuropilin-2 control the migration of human T-cell precursors. *PloS one* 9, e103405 (2014).
29. Flaxenburg J A, Melter M, Lapchak P H, Briscoe D M, Pal S. The CD40-induced signaling pathway in endothelial cells resulting in the overexpression of vascular endothelial growth factor involves Ras and phosphatidylinositol 3-kinase. *Journal of immunology* (Baltimore, Md.: 1950) 172, 7503-7509 (2004).
30. Kang S A, et al. mTORC1 phosphorylation sites encode their sensitivity to starvation and rapamycin. *Science* (New York, N.Y.) 341, 1236566 (2013).
31. Pollizzi K N, Powell J D. Integrating canonical and metabolic signaling programmes in the regulation of T cell responses. *Nature reviews Immunology* 14, 435-446 (2014).
32. Bruneau S, Nakayama H, Woda C B, Flynn E A, Briscoe D M. DEPTOR regulates vascular endothelial cell activation and proinflammatory and angiogenic responses. *Blood* 122, 1833-1842 (2013).
33. Dazert E, Hall M N. mTOR signaling in disease. *Current opinion in cell biology* 23, 744-755 (2011).
34. Phung T L, et al. Endothelial Akt signaling is rate-limiting for rapamycin inhibition of mouse mammary tumor progression. *Cancer research* 67, 5070-5075 (2007).
35. Shimobayashi M, Hall M N. Making new contacts: the mTOR network in metabolism and signalling crosstalk. *Nature reviews Molecular cell biology* 15, 155-162 (2014).
36. Dormond O, et al. CD40-induced signaling in human endothelial cells results in mTORC2- and Akt-dependent expression of vascular endothelial growth factor in vitro and in vivo. *Journal of immunology* (Baltimore, Md.: 1950) 181, 8088-8095 (2008).
37. Dormond O, Madsen J C, Briscoe D M. The effects of mTOR-Akt interactions on anti-apoptotic signaling in vascular endothelial cells. *The Journal of biological chemistry* 282, 23679-23686 (2007).
38. Zhang H H, Lipovsky A I, Dibble C C, Sahin M, Manning B D. S6K1 regulates GSK3 under conditions of mTOR-dependent feedback inhibition of Akt. *Molecular cell* 24, 185-197 (2006).
39. Burridge K, Wennerberg K. Rho and Rac take center stage. *Cell* 116, 167-179 (2004).
40. Carmeliet P, Jain R K. Principles and mechanisms of vessel normalization for cancer and other angiogenic diseases. *Nature reviews Drug discovery* 10, 417-427 (2011).
41. Ferrara N, Kerbel R S. Angiogenesis as a therapeutic target. *Nature* 438, 967-974 (2005).
42. Karar J, Maity A. PI3K/AKT/mTOR Pathway in Angiogenesis. *Frontiers in molecular neuroscience* 4, 51 (2011).
43. Krock B L, Skuli N, Simon M C. Hypoxia-induced angiogenesis: good and evil. *Genes & cancer* 2, 1117-1133 (2011).
44. Cao Y, et al. Neuropilin-2 promotes extravasation and metastasis by interacting with endothelial alpha5 integrin. *Cancer research* 73, 4579-4590 (2013).

45. Sabag A D, Bode J, Fink D, Kigel B, Kugler W, Neufeld G. Semaphorin-3D and semaphorin-3E inhibit the development of tumors from glioblastoma cells implanted in the cortex of the brain. *PloS one* 7, e42912 (2012).
46. Gan X, Wang J, Su B, Wu D. Evidence for direct activation of mTORC2 kinase activity by phosphatidylinositol 3,4,5-trisphosphate. *The Journal of biological chemistry* 286, 10998-11002 (2011).
47. Zinzalla V, Stracka D, Oppliger W, Hall M N. Activation of mTORC2 by association with the ribosome. *Cell* 144, 757-768 (2011).
48. Levitt R J, Georgescu M M, Pollak M. PTEN-induction in U251 glioma cells decreases the expression of insulin-like growth factor binding protein-2. *Biochemical and biophysical research communications* 336, 1056-1061 (2005).
49. Sakai A, Thieblemont C, Wellmann A, Jaffe E S, Raffeld M. PTEN gene alterations in lymphoid neoplasms. *Blood* 92, 3410-3415 (1998).
50. Wen S, et al. PTEN controls tumor-induced angiogenesis. *Proceedings of the National Academy of Sciences of the United States of America* 98, 4622-4627 (2001).
51. Cai H, Reed R R. Cloning and characterization of neuropilin-1-interacting protein: a PSD-95/Dlg/ZO-1 domain-containing protein that interacts with the cytoplasmic domain of neuropilin-1. *The Journal of neuroscience: the official journal of the Society for Neuroscience* 19, 6519-6527 (1999).
52. Katoh M. Functional proteomics, human genetics and cancer biology of GIPC family members. *Experimental & molecular medicine* 45, e26 (2013).
53. Wang L, Mukhopadhyay D, Xu X. C terminus of RGS-GAIP-interacting protein conveys neuropilin-1-mediated signaling during angiogenesis. *FASEB journal: official publication of the Federation of American Societies for Experimental Biology* 20, 1513-1515 (2006).
54. Peterson T R, et al. DEPTOR is an mTOR inhibitor frequently overexpressed in multiple myeloma cells and required for their survival. *Cell* 137, 873-886 (2009).
55. Jacinto E, et al. Mammalian TOR complex 2 controls the actin cytoskeleton and is rapamycin insensitive. *Nature cell biology* 6, 1122-1128 (2004).
56. Kessler O, et al. Semaphorin-3F is an inhibitor of tumor angiogenesis. *Cancer research* 64, 1008-1015 (2004).
57. Kigel B, Varshavsky A, Kessler O, Neufeld G. Successful inhibition of tumor development by specific class-3 semaphorins is associated with expression of appropriate semaphorin receptors by tumor cells. *PloS one* 3, e3287 (2008).
58. Sekulic A, et al. A direct linkage between the phosphoinositide 3-kinase-AKT signaling pathway and the mammalian target of rapamycin in mitogen-stimulated and transformed cells. *Cancer research* 60, 3504-3513 (2000).
59. Mukhopadhyay D, Knebelmann B, Cohen H T, Ananth S, Sukhatme V P. The von Hippel-Lindau tumor suppressor gene product interacts with Sp1 to repress vascular endothelial growth factor promoter activity. *Molecular and cellular biology* 17, 5629-5639 (1997).
60. Bielenberg D R, Shimizu A, Klagsbrun M. Semaphorin-induced cytoskeletal collapse and repulsion of endothelial cells. *Methods in enzymology* 443, 299-314 (2008).

Example 13

Figure 37:
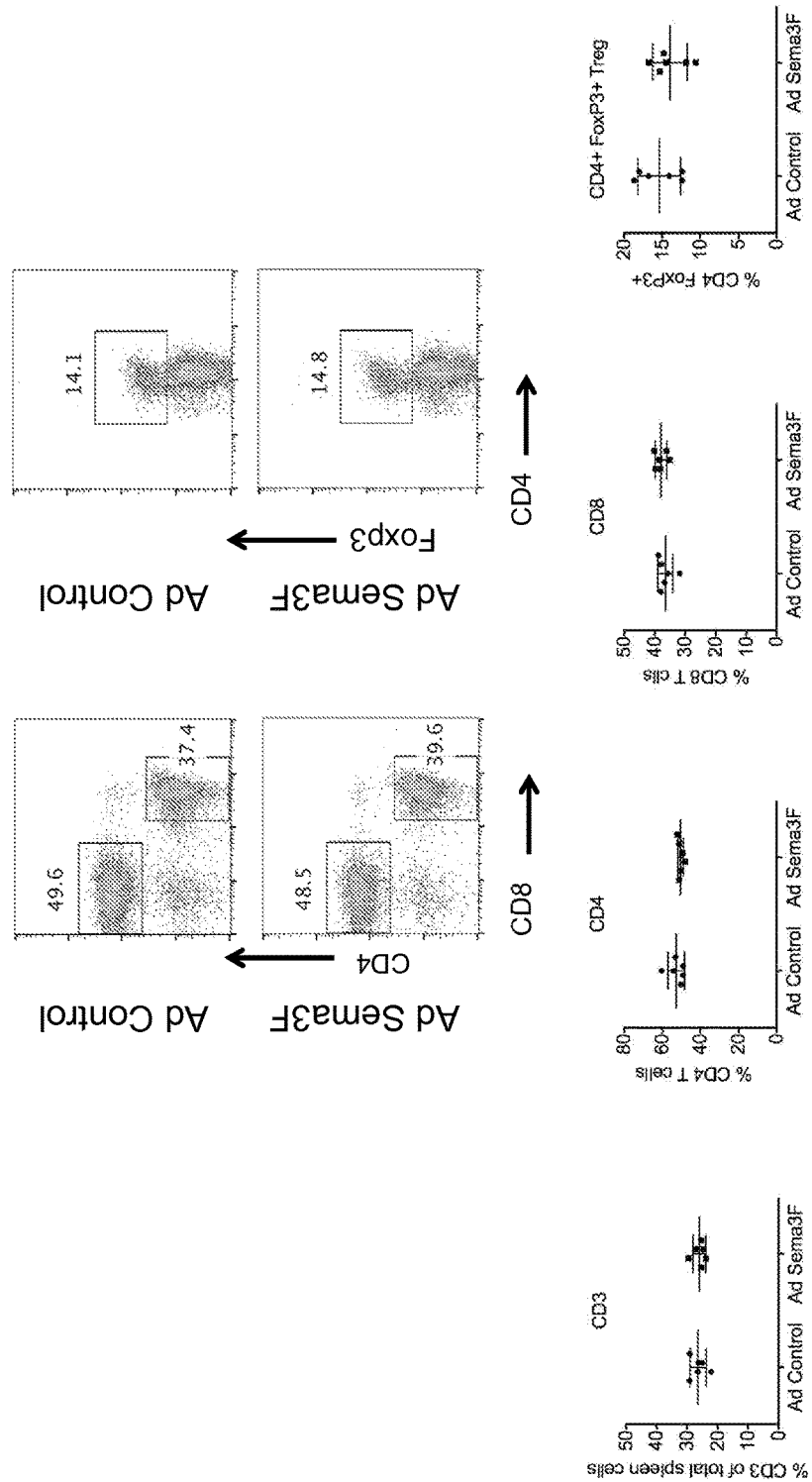
FIG. 37 depicts the phenotype of cells harvested from the mice identified in FIG. 2 on day 5 post transplantation. FACS analysis and graphical summaries demonstrating that no differences are observed in CD3, CD4, CD8 and Treg populations at early times post transplant.
Figure 38:
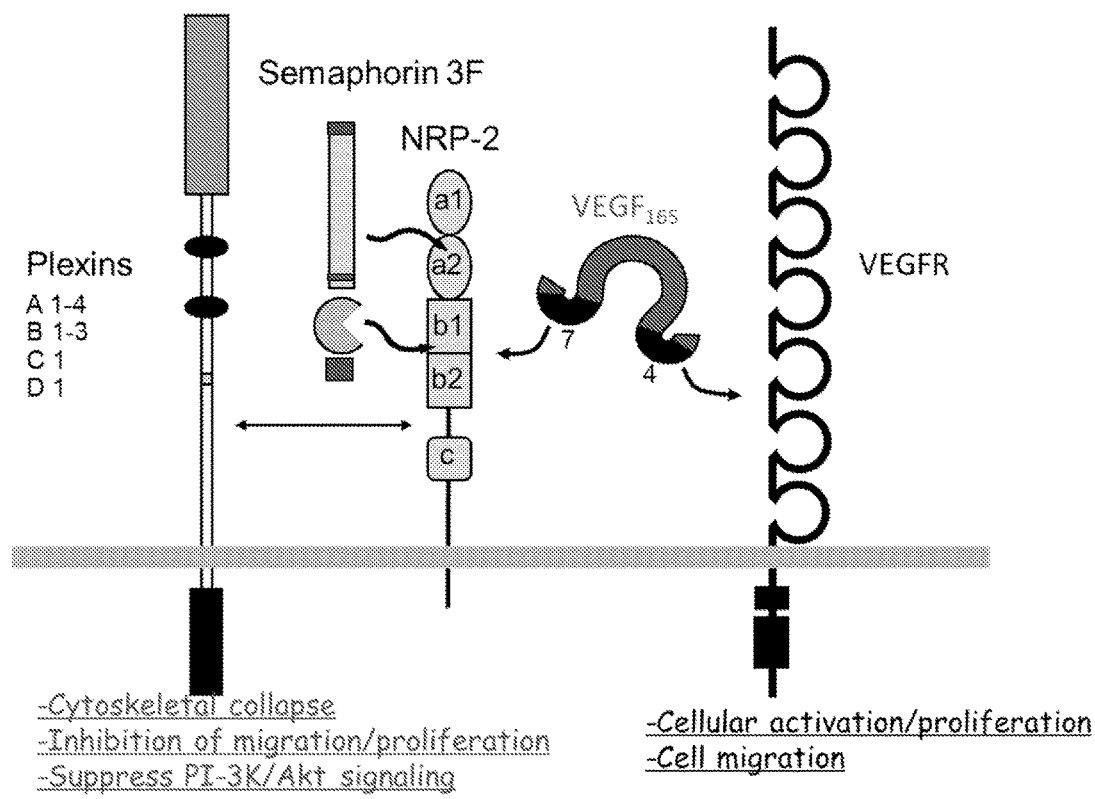
FIG. 38 depicts a schematic model of semaphorin-neuropilin-2 interactions.

The immunoregulatory function of Sema3F was evaluated by examining the Treg phenotype at early times post transplant, on day 5 shown in FIG. 2. As shown by FACS and in the lower panel in a summary (FIG. 37), no differences are observed in CD3, CD4, CD8 and Tregs.

Example 14

Figure 39:
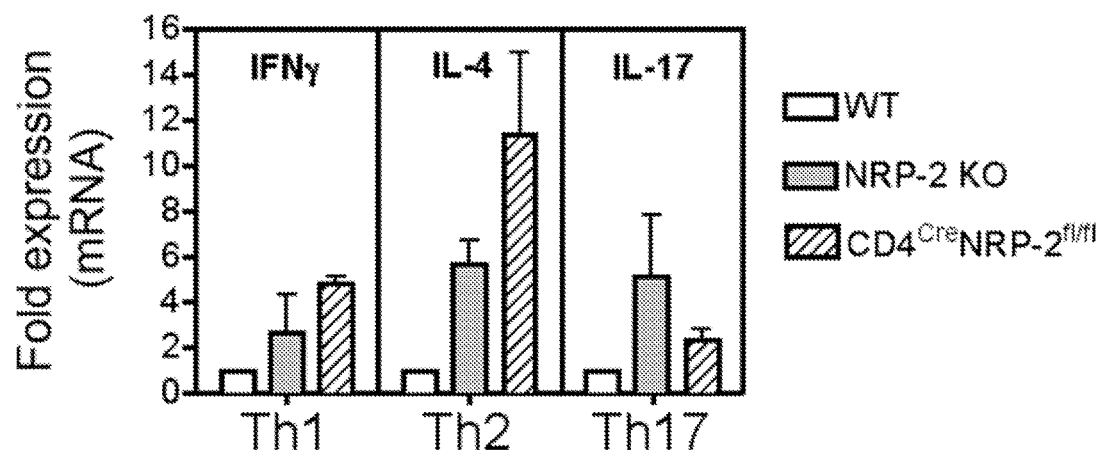
FIG. 39 is a follow up of FIGS. 11-16 and FIG. 23 where knockdown of NRP-2 was found to result in hyperactivity. In this Figure, T cells were mitogen activated in cultures that drive responses into different effector phenotypes. As depicted in the graph CD4+ T effector cell differentiation is enhanced in NRP-2 Knockout CD4+ T cells.

CD4+ T effector cell differentiation was examined in NRP-2 knockouts and conditional knockouts. Differentiation is enhanced in NRP-2 Knockout CD4+ T cells (FIG. 39). The data indicate that NRP-2 inhibits effector T cell expansion.

Example 15

Figure 40:
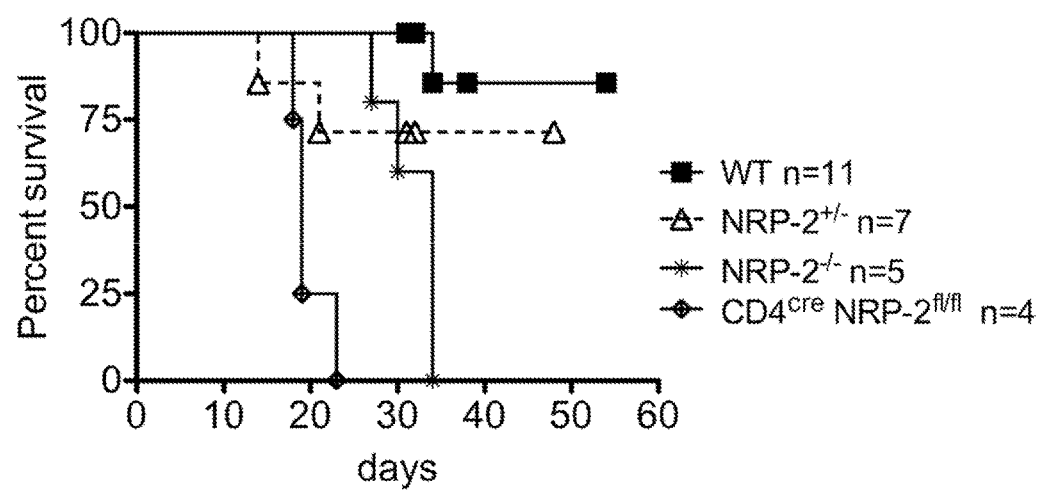
FIG. 40 is the combined data from FIGS. 5 and 25 demonstrating that NRP-2 deficiency led to accelerated cardiac allograft rejection. The figure depicts a graph of survival after minor MHC mismatched B6.C-H2$^{bm12}$ donor heart was transplanted into C57BL6 (WT) or NRP-2 heterozygote, and global or CD4+ T cell KO recipients.

Minor MHC mismatched B6.C-H2$^{bm12}$ donor heart was transplanted into C57BL6 (WT) or NRP-2 KO recipients and survival was determined NRP-2 deficiency lead to accelerated cardiac allograft rejection (FIG. 40).

Example 16

Figure 41:
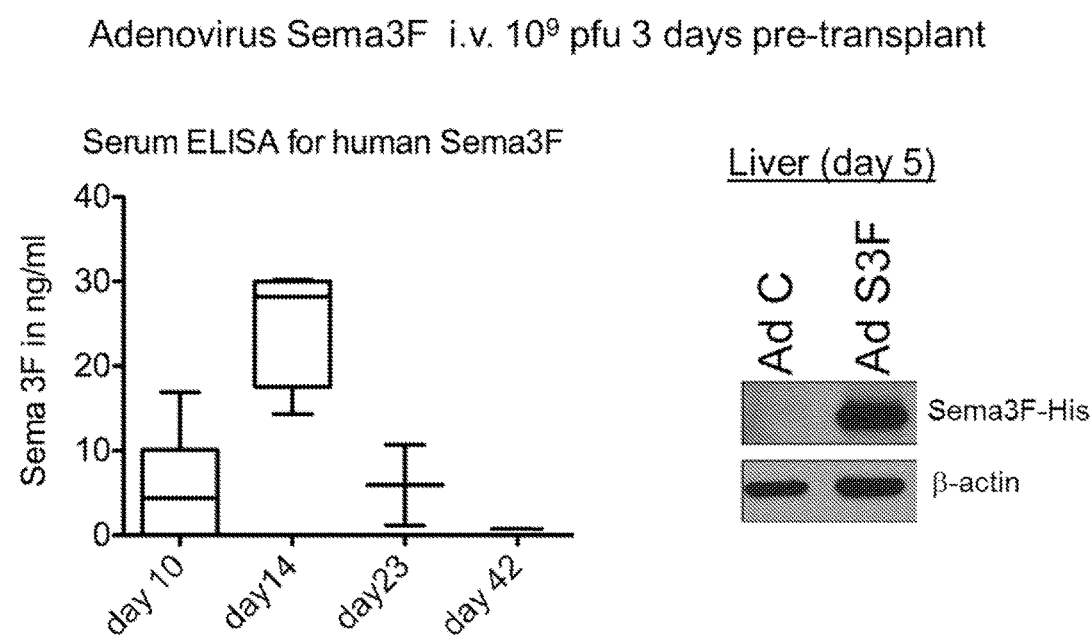
FIG. 41 shows data demonstrating the production of the NRP-2 ligand Sema3F in vivo by adenovirus.

To study the effect of the NRP-2 ligand Sema3F in vivo, an Adenovirus containing Sema3F or an empty control was administered into mice in a heart transplant model. The Sema3F vector increased production of Sema3F in the liver. Sema3F levels peak on day 14 following administration (FIG. 41).

TABLE 1

| Coordinate | Target | Control | SEMA3F | Ratio |
|---|---|---|---|---|
| A1, A2 | Positive Control | 0.513 | 0.544 | 106.0 |
| A3, A4 | p38a (T180/Y182) | 0.292 | 0.268 | 91.8 |
| A5, A6 | ERK1/2 (T202/Y204, T185/Y187) | 0.330 | 0.301 | 91.2 |
| A7, A8 | JNK pan (T183/Y185, T221/Y223) | 0.313 | 0.287 | 91.5 |
| A9, A10 | GSK-3a/b (S21/S9) | 0 312 | 0.284 | 91.0 |
| A13, A14 | p53 (S392) | 0.332 | 0.312 | 94.0 |
| A17, A18 | Positive Control | 0.412 | 0.392 | 95.1 |
| B3, B4 | MEK1/2 (S218/S222, S222/S226) | 0.299 | 0.277 | 92.8 |
| B5, B6 | MSK1/2 (S376/S360) | 0.317 | 0.293 | 92.4 |
| B7, B8 | AMPKa1 (T174) | 0.290 | 0.289 | 92.7 |
| B9, B10 | Akt (S473) | 0.512 | 0.396 | 77.4 |
| B11, B12 | Akt (T308) | 0.317 | 0.294 | 92.6 |
| B13, B14 | p53 (S46) | 0.343 | 0.321 | 93.8 |
| C1, C2 | TOR (S2448) | 0.306 | 0.281 | 91.8 |
| C3, C4 | CREB (S133) | 0.323 | 0.295 | 91.3 |
| C5, C6 | HSP27 (S78/S82) | 0 294 | 0.277 | 94.0 |
| C7, C8 | AMPKa2 (T172) | 0.317 | 0.300 | 94.5 |
| C9, C10 | b-Catenin | 0.352 | 0.323 | 91.6 |
| C11, C12 | p70 S6 Kinase (T389) | 0.252 | 0.241 | 95.6 |
| C13, C14 | p53 (S15) | 0.322 | 0.312 | 96.7 |
| C15, C16 | p27 (T198) | 0.257 | 0.242 | 94.0 |
| C17, C18 | Paxillin (Y118) | 0.275 | 0.264 | 95.8 |
| D1, D2 | Src (Y419) | 0.317 | 0.289 | 91.0 |
| D3, D4 | Lyn (Y397) | 0.287 | 0.269 | 93.7 |
| D5, D6 | Lck (Y394) | 0 288 | 0.269 | 94.2 |
| D7, D8 | STAT2 (Y689) | 0.320 | 0.305 | 95.3 |
| D9, D10 | STAT5a (Y694) | 0.297 | 0.281 | 94.8 |
| D11, D12 | p70 S6 Kinase (T421/S424) | 0.307 | 0.299 | 97.4 |
| D13, D14 | RSK1/2/3 (S380/S386/S377) | 0.324 | 0.320 | 98.8 |
| D15, D16 | p27 (T157) | 0.264 | 0.249 | 94.3 |
| D17, D18 | PLCq-1 (Y783) | 0.275 | 0.262 | 95.1 |
| E1, E2 | Fyn (Y420) | 0.297 | 0.276 | 93.1 |
| E3, E4 | Yes (Y426) | 0.305 | 0.289 | 94.6 |
| E5, E6 | Fgr (Y412) | 0.280 | 0.264 | 94.1 |
| E7, E8 | STAT3 (Y705) | 0.289 | 0.270 | 93.4 |
| E9, E10 | STAT5b (Y699) | 0.291 | 0.270 | 92.6 |
| E11, E12 | p70 S6 Kinase (T229) | 0.264 | 0.284 | 100.0 |
| E13, E14 | RSK1/2 (S221/S227) | 0.314 | 0.307 | 97.8 |
| E15, E16 | c-Jun (S63) | 0.279 | 0.263 | 94.3 |
| E17, E18 | Pyk2 (Y402) | 0.269 | 0.251 | 93.1 |
| F1, F2 | Hck (Y411) | 0.295 | 0.270 | 91.4 |

TABLE 1-continued

| Coodinate | Target | Control | SEMA3F | Ratio |
|---|---|---|---|---|
| F3, F4 | Chk-2 (T68) | 0.318 | 0.297 | 93.4 |
| F5, F6 | FAK (Y397) | 0.314 | 0.275 | 87.7 |
| F7, F8 | STAT6 (Y641) | 0.315 | 0.304 | 96.3 |
| F9, F10 | STAT5a/b (Y694/Y699) | 0.345 | 0.311 | 90.1 |
| F11, F12 | STAT1 (Y701) | 0.304 | 0.298 | 98.2 |
| F13, F14 | STAT4 (Y693) | 0.295 | 0.285 | 96.4 |

TABLE 1-continued

| Coodinate | Target | Control | SEMA3F | Ratio |
|---|---|---|---|---|
| F15, F16 | eNOS (S1177) | 0.255 | 0.240 | 93.9 |
| F17, F18 | PBS (Negative Control) | — | — | — |
| G1, G2 | Positive Control | 0.490 | 0.487 | 99.4 |
| G5, G6 | PBS (Negative Control) | — | — | — |

What is claimed herein is:

1. A method of suppressing allograft rejection, the method comprising administering a therapeutically effective amount of a Semaphorin 3F (Sema3F) agonist to an allograft recipient, whereby immune rejection of the allograft is suppressed, and
   a. wherein the Sema3F agonist is a Sema3F polypeptide that binds to a Sema3F receptor, or
   b. wherein the Sema3F agonist is a nucleic acid encoding a Sema3F polypeptide that binds to a Sema3F receptor.

2. The method of claim 1, wherein the Sema3F agonist is a Sema3F polypeptide.

3. The method of claim 2, wherein the polypeptide comprises a sequence having at least 95% identity to the sequence of SEQ ID NO: 1 or 5.

4. The method of claim 2, wherein the Sema3F polypeptide comprises the sequence of SEQ ID NO: 5.

5. The method of claim 1, wherein the Sema3F agonist is a nucleic acid encoding a Sema3F polypeptide.

6. The method of claim 1, wherein the allograft is a cardiac allograft.

7. A method of prolonging the survival of an allogeneic transplant recipient, the method comprising administering a therapeutically effective amount of a Semaphorin 3F (Sema3F) agonist to an allogeneic transplant recipient, whereby the survival of the recipient is prolonged, and
   a. wherein the Sema3F agonist is a Sema3F polypeptide that binds to a Sema3F receptor, or
   b. wherein the Sema3F agonist is a nucleic acid encoding a Sema3F polypeptide that binds to a Sema3F receptor.

8. The method of claim 7, wherein the Sema3F agonist is a Sema3F polypeptide.

9. The method of claim 8, wherein the polypeptide comprises a sequence having at least 95% identity to the sequence of SEQ ID NO: 1 or 5.

10. The method of claim 8, wherein the Sema3F polypeptide comprises the sequence of SEQ ID NO: 5.

11. The method of claim 7, wherein the Sema3F agonist is a nucleic acid encoding a Sema3F polypeptide.

12. The method of claim 7, wherein the allogeneic transplant is a cardiac allogeneic transplant.

13. A method of inhibiting rejection of an allogeneic transplant recipient, the method comprising administering a therapeutically effective amount of a Semaphorin 3F (Sema3F) agonist to an allogeneic transplant recipient, whereby rejection of the allogeneic transplant is inhibited, and
   a. wherein the Sema3F agonist is a Sema3F polypeptide that binds to a Sema3F receptor, or
   b. wherein the Sema3F agonist is a nucleic acid encoding a Sema3F polypeptide that binds to a Sema3F receptor.

14. The method of claim 13, wherein the Sema3F agonist is a Sema3F polypeptide.

15. The method of claim 14, wherein the polypeptide comprises a sequence having at least 95% identity to the sequence of SEQ ID NO: 1 or 5.

16. The method of claim 14, wherein the Sema3F polypeptide comprises the sequence of SEQ ID NO: 5.

17. The method of claim 13, wherein the Sema3F agonist is a nucleic acid encoding a Sema3F polypeptide.

18. The method of claim 13, wherein the allogeneic transplant is a cardiac allogeneic transplant.

19. A method of inhibiting rejection of an organ transplant, the method comprising administering a therapeutically effective amount of a Semaphorin 3F (Sema3F) agonist to an organ transplant recipient, whereby rejection of the organ transplant is inhibited, and
   a. wherein the Sema3F agonist is a Sema3F polypeptide that binds to a Sema3F receptor, or
   b. wherein the Sema3F agonist is a nucleic acid encoding a Sema3F polypeptide that binds to a Sema3F receptor.

20. The method of claim 19, wherein the Sema3F agonist is a Sema3F polypeptide.

21. The method of claim 20, wherein the polypeptide comprises a sequence having at least 95% identity to the sequence of SEQ ID NO: 1 or 5.

22. The method of claim 20, wherein the Sema3F polypeptide comprises the sequence of SEQ ID NO: 5.

23. The method of claim 19, wherein the Sema3F agonist is a nucleic acid encoding a Sema3F polypeptide.

24. The method of claim 19, wherein the organ transplant is a cardiac organ transplant.

* * * * *

SEQUENCE LISTING

<160> NUMBER OF SEQ ID NOS: 7

<210> SEQ ID NO 1
<211> LENGTH: 785
<212> TYPE: PRT
<213> ORGANISM: Homo sapiens

<400> SEQUENCE: 1

Met Leu Val Ala Gly Leu Leu Trp Ala Ser Leu Leu Thr Gly Ala
1               5                   10                  15

Trp Pro Ser Phe Pro Thr Gln Asp His Leu Pro Ala Thr Pro Arg Val
            20                  25                  30

Arg Leu Ser Phe Lys Glu Leu Lys Ala Thr Gly Thr Ala His Phe Phe
        35                  40                  45

Asn Phe Leu Leu Asn Thr Thr Asp Tyr Arg Ile Leu Leu Lys Asp Glu
    50                  55                  60

Asp His Asp Arg Met Tyr Val Gly Ser Lys Asp Tyr Val Leu Ser Leu
65                  70                  75                  80

Asp Leu His Asp Ile Asn Arg Glu Pro Leu Ile Ile His Trp Ala Ala
                85                  90                  95

Ser Pro Gln Arg Ile Glu Glu Cys Val Leu Ser Gly Lys Asp Val Asn
            100                 105                 110

Gly Glu Cys Gly Asn Phe Val Arg Leu Ile Gln Pro Trp Asn Arg Thr
        115                 120                 125

His Leu Tyr Val Cys Gly Thr Gly Ala Tyr Asn Pro Met Cys Thr Tyr
    130                 135                 140

Val Asn Arg Gly Arg Arg Ala Gln Ala Thr Pro Trp Thr Gln Thr Gln
145                 150                 155                 160

Ala Val Arg Gly Arg Gly Ser Arg Ala Thr Asp Gly Ala Leu Arg Pro
                165                 170                 175

Met Pro Thr Ala Pro Arg Gln Asp Tyr Ile Phe Tyr Leu Glu Pro Glu
            180                 185                 190

Arg Leu Glu Ser Gly Lys Gly Lys Cys Pro Tyr Asp Pro Lys Leu Asp
        195                 200                 205

Thr Ala Ser Ala Leu Ile Asn Glu Glu Leu Tyr Ala Gly Val Tyr Ile
    210                 215                 220

Asp Phe Met Gly Thr Asp Ala Ala Ile Phe Arg Thr Leu Gly Lys Gln
225                 230                 235                 240

Thr Ala Met Arg Thr Asp Gln Tyr Asn Ser Arg Trp Leu Asn Asp Pro
                245                 250                 255

Ser Phe Ile His Ala Glu Leu Ile Pro Asp Ser Ala Glu Arg Asn Asp
            260                 265                 270

Asp Lys Leu Tyr Phe Phe Phe Arg Glu Arg Ser Ala Glu Ala Pro Gln
        275                 280                 285

Ser Pro Ala Val Tyr Ala Arg Ile Gly Arg Ile Cys Leu Asn Asp Asp
    290                 295                 300

-continued

```
Gly Gly His Cys Cys Leu Val Asn Lys Trp Ser Thr Phe Leu Lys Ala
305                 310                 315                 320
Arg Leu Val Cys Ser Val Pro Gly Glu Asp Gly Ile Glu Thr His Phe
                325                 330                 335
Asp Glu Leu Gln Asp Val Phe Val Gln Thr Gln Asp Val Arg Asn
            340                 345                 350
Pro Val Ile Tyr Ala Val Phe Thr Ser Ser Gly Ser Val Phe Arg Gly
                355                 360                 365
Ser Ala Val Cys Val Tyr Ser Met Ala Asp Ile Arg Met Val Phe Asn
370                 375                 380
Gly Pro Phe Ala His Lys Glu Gly Pro Asn Tyr Gln Trp Met Pro Phe
385                 390                 395                 400
Ser Gly Lys Met Pro Tyr Pro Arg Pro Gly Thr Cys Pro Gly Gly Thr
                405                 410                 415
Phe Thr Pro Ser Met Lys Ser Thr Lys Asp Tyr Pro Asp Glu Val Ile
                420                 425                 430
Asn Phe Met Arg Ser His Pro Leu Met Tyr Gln Ala Val Tyr Pro Leu
            435                 440                 445
Gln Arg Arg Pro Leu Val Val Arg Thr Gly Ala Pro Tyr Arg Leu Thr
450                 455                 460
Thr Ile Ala Val Asp Gln Val Asp Ala Ala Asp Gly Arg Tyr Glu Val
465                 470                 475                 480
Leu Phe Leu Gly Thr Asp Arg Gly Thr Val Gln Lys Val Ile Val Leu
                485                 490                 495
Pro Lys Asp Asp Gln Glu Leu Glu Glu Leu Met Leu Glu Glu Val Glu
                500                 505                 510
Val Phe Lys Asp Pro Ala Pro Val Lys Thr Met Thr Ile Ser Ser Lys
                515                 520                 525
Arg Gln Gln Leu Tyr Val Ala Ser Ala Val Gly Val Thr His Leu Ser
            530                 535                 540
Leu His Arg Cys Gln Ala Tyr Gly Ala Ala Cys Ala Asp Cys Cys Leu
545                 550                 555                 560
Ala Arg Asp Pro Tyr Cys Ala Trp Asp Gly Gln Ala Cys Ser Arg Tyr
                565                 570                 575
Thr Ala Ser Ser Lys Arg Arg Ser Arg Arg Gln Asp Val Arg His Gly
                580                 585                 590
Asn Pro Ile Arg Gln Cys Arg Gly Phe Asn Ser Asn Ala Asn Lys Asn
            595                 600                 605
Ala Val Glu Ser Val Gln Tyr Gly Val Ala Gly Ser Ala Ala Phe Leu
            610                 615                 620
Glu Cys Gln Pro Arg Ser Pro Gln Ala Thr Val Lys Trp Leu Phe Gln
625                 630                 635                 640
Arg Asp Pro Gly Asp Arg Arg Glu Ile Arg Ala Glu Asp Arg Phe
                645                 650                 655
Leu Arg Thr Glu Gln Gly Leu Leu Leu Arg Ala Leu Gln Leu Ser Asp
                660                 665                 670
Arg Gly Leu Tyr Ser Cys Thr Ala Thr Glu Asn Asn Phe Lys His Val
                675                 680                 685
Val Thr Arg Val Gln Leu His Val Leu Gly Arg Asp Ala Val His Ala
            690                 695                 700
Ala Leu Phe Pro Pro Leu Ser Met Ser Ala Pro Pro Pro Gly Ala
705                 710                 715                 720
```

Gly Pro Pro Thr Pro Pro Tyr Gln Glu Leu Ala Gln Leu Leu Ala Gln
            725                 730                 735

Pro Glu Val Gly Leu Ile His Gln Tyr Cys Gln Gly Tyr Trp Arg His
        740                 745                 750

Val Pro Pro Ser Pro Arg Glu Ala Pro Gly Ala Pro Arg Ser Pro Glu
    755                 760                 765

Pro Gln Asp Gln Lys Lys Pro Arg Asn Arg Arg His His Pro Pro Asp
    770                 775                 780

Thr
785

<210> SEQ ID NO 2
<211> LENGTH: 3531
<212> TYPE: DNA
<213> ORGANISM: Homo sapiens

<400> SEQUENCE: 2

```
ccgcggcgcc gatcccggct gaggcgcagc ggcgagaggt cgcgggcagg gccatggccc      60
cgggggggccg ctagcgcgga ccggcccaac gggagccgct ccgtgccgcc gccgccgccc     120
gggcgcccag gccccgccgc tgcggaagag gtttctagag agtggagcct gcttcctggg     180
ccctaggccc ctcccacaat gcttgtcgcc ggtcttcttc tctgggcttc cctactgacc     240
ggggcctggc catccttccc cacccaggac cacctcccgg ccacgccccg ggtccggctc     300
tcattcaaag agctgaaggc cacaggcacc gcccactct tcaacttcct gctcaacaca      360
accgactacc gaatcttgct caaggacgag accacgacc gcatgtacgt gggcagcaag      420
gactacgtgc tgtccctgga cctgcacgac atcaaccgcg agcccctcat tatacactgg      480
gcagcctccc cacagcgcat cgaggaatgc gtgctctcag gcaaggatgt caacggcgag      540
tgtgggaact tcgtcaggct catccagccc tggaaccgaa cacacctgta tgtgtgcggg      600
acaggtgcct acaaccccat gtgcaccctat gtgaaccgcg acgccgcgc ccaggccaca      660
ccatggaccc agactcaggc ggtcagaggc cgcggcagca gagccacgga tggtgccctc      720
cgcccgatgc ccacagcccc acgccaggat tacatcttct acctggagcc tgagcgactc      780
gagtcaggga agggcaagtg tccgtacgat cccaagctgg acacagcatc ggccctcatc      840
aatgaggagc tctatgctgg tgtgtacatc gatttatgg gcactgatgc agccatcttc      900
cgcacacttg aaagcagac agccatgcgc acggatcagt acaactcccg gtggctgaac      960
gacccgtcgt tcatccatgc tgagctcatt cctgacagtg cggagcgcaa tgatgataag     1020
ctttacttct tcttccgtga gcggtcggca gaggcgccgc agagcccgc ggtgtacgcc      1080
cgcatcgggc gcatttgcct gaacgatgac ggtggtcact gttgcctggt caacaagtgg     1140
agcacattcc tgaaggcgcg gctcgtctgc tctgtcccgg gcgaggatgg cattgagact     1200
cactttgatg agctccagga cgtgtttgtc cagcagaccc aggacgtgag gaaccctgtc     1260
atttacgctg tctttacctc ctctggctcc gtgttccgag gtctctgccgt gtgtgtctac     1320
tccatggctg atattcgcat ggtcttcaac gggcccttg cccacaaaga ggggcccaac     1380
taccagtgga tgcccttctc agggaagatg ccctacccac ggccgggcac gtgcctggt      1440
ggaaccttca cgccatctat gaagtccacc aaggattatc ctgatgaggt gatcaacttc     1500
atgcgcagcc acccactcat gtaccaggcc gtgtaccctc tgcagcggcg gcccctggta     1560
gtccgcacag gtgctcccta ccgccttacc actattgccg tggaccaggt ggatgcagcc     1620
gacgggcgct atgaggtgct tttcctgggc acagaccgcg ggacagtgca gaaggtcatt     1680
```

```
gtgctgccca aggatgacca ggagttggag gagctcatgc tggaggaggt ggaggtcttc      1740
aaggatccag cacccgtcaa gaccatgacc atctcttcta agaggcaaca actctacgtg      1800
gcgtcagccg tgggtgtcac acacctgagc ctgcaccgct gccaggcgta tggggctgcc      1860
tgtgctgact gctgccttgc ccgggaccct tactgtgcct gggatggcca ggcctgctcc      1920
cgctatacag catcctccaa gaggcggagc cgccggcagg acgtccggca cggaaacccc      1980
atcaggcagt gccgtgggtt caactccaat gccaacaaga atgccgtgga gtctgtgcag      2040
tatggcgtgg ccggcagcgc agccttcctt gagtgccagc ccgctcgcc ccaagccact       2100 gttaagtggc tgttccagcg agatcctggt gaccggcgcc gagagattcg tgcagaggac      2160
cgcttcctgc gcacagagca gggcttgttg ctccgtgcac tgcagctcag cgatcgtggc      2220
ctctactcct gcacagccac tgagaacaac tttaagcacg tcgtcacacg agtgcagctg      2280
catgtactgg gccgggacgc cgtccatgct gccctcttcc caccactgtc catgagcgcc      2340
ccgccacccc caggcgcagg cccccaacg cctccttacc aggagttagc ccagctgctg       2400
gcccagccag aagtgggcct catccaccag tactgccagg gttactggcg ccatgtgccc      2460
cccagcccca gggaggctcc aggggcaccc cggtctcctg agcccagga ccagaaaaag       2520 ccccggaacc gccggcacca ccctccggac acatgaggcc agctgcctgt gcctgccatg      2580
ggccagccta gcccttgtcc cttttaatat aaaagatata tatatatata tatatatata      2640
aaatatctat attctataca caccctgccc ctgcaaagac agtatttatt ggtgggttga      2700
atatagcctg cctcagtggc agcatcctcc aaaacttaga cccatgctgg tcagagacgg      2760
cagaaaacag agcctgccta accaggccca gccagttggt ggggccaggc caggaccaca      2820
cagtccccag actcagctgg aagtctacct gctggacagc ctccgccaag atctacagga      2880
caaagggagg gagcaagccc tactcggatg gggcacggac tgtccacctt ttctgatgtg      2940
tgttgtcagc ctgtgctgtg gcatagacat ggatgcgagg accactttgg agactggggt      3000
ggcctcaaga gcacacagag aagggaagaa ggggccatca caggatgcca gcccctgcct      3060
gggttggggg cactcagcca cgaccagccc cttcctgggt atttattctc tatttattgg      3120
ggataggaga agaggcatcc tgcctgggtg ggacagcctc ttcagcccct tctcccctcc      3180
ccgcctggcc agggcagggc cacccactc tacctcctta gctttccctg tgccactttg       3240
actcagaggc tggagcata gcagagggggc caggcccagg cagagctgac gggaggcccc      3300
agctctgagg ggaggggtc cgtggtagag gcctggggcc ggtagaggct ccccagggct       3360
cccttatgtc caccacttca ggggatgggt gtggatgtaa ttagctctgg ggggcagttg      3420
ggtagatggg tgggggctcc tggtggcctt ctgctgccca ggccacagcc gcctttgggt      3480
tccatcttgc taataaacac tggctctggg actagaaaaa aaaaaaaaa a                3531
```

<210> SEQ ID NO 3
<211> LENGTH: 6671
<212> TYPE: DNA
<213> ORGANISM: Homo sapiens

<400> SEQUENCE: 3

```
cagagatcgc gagcgaggca ccagcctgca gccggccccc agcacatcct cagccgcaca        60
gacactcggc gaggtggagg tgagggcggg cgccagcgaa ctcggagagg ggctcgctca       120
ctcccaggcg atcccagccc ccaccgccgc gcaccagca gcagcaacag cagcagcagc       180
ttccttcctc agactcccct cgagaggctg gccaagcggg tgtagccgtt gggggaggct      240
cccgccgggg gaacccggcg aggacaagag cagggcggcc gccttccact cgggctgtcc      300
```

```
ggcggcggct gcctccgccc gtgtgtccgt caagggtgcc gcgggatgtg tgtcagttta    360
cgcctctgag atcacacagc tgcctggggg ccgtgtgatg cccaaggcaa gtcttggttt    420
taattattat tattatcatt attgttacgc ttggctttcg ggaaatactc gtgatatttg    480
taggataaag gaaatgacac tttgaggaac tggagagaac atatatgcgt tttgttttta    540
agaggaaaac cgtgttctct tcccggcttg ttccctcttt gctgatttca ggagctactc    600
tcctcctggt gaggtggaaa ttccagcaag aatagaggtg aagacaagcc accaggactc    660
aggagggaaa cgctgaccat tagaaacctc tgcataagac gttgtaagga ggaaaataaa    720
agagagaaaa acacaaagat ttaaacaaga aacctacgaa cccagctctg aaagagcca    780 ccttctccaa aatggatatg tttcctctca cctgggtttt cttagccctc acttttcaa    840 gacaccaagt gagaggccaa ccagacccac cgtgcggagg tcgtttgaat tccaaagatg    900
ctggctatat cacctctccc ggttaccccc aggactaccc ctcccaccag aactgcgagt    960
ggattgttta cgcccccgaa cccaaccaga agattgtcct caacttcaac cctcactttg   1020
aaatcgagaa gcacgactgc aagtatgact ttatcgagat tcgggatggg gacagtgaat   1080
ccgcagacct cctgggcaaa cactgtggga acatcgcccc gccaccatc atctcctcgg   1140 gctccatgct ctacatcaag ttcacctccg actacgcccg gcaggggca ggcttctctc   1200 tgcgctacga gatcttcaag acaggctctg aagattgctc aaaaaacttc acaagcccca   1260
acgggaccat cgaatctcct gggtttcctg agaagtatcc acacaacttg gactgcacct   1320
ttaccatcct ggccaaaccc aagatggaga tcatcctgca gttcctgatc tttgacctgg   1380
agcatgaccc tttgcaggtg ggagaggggg actgcaagta cgattggctg acatctggg   1440 atggcattcc acatgttggc cccctgattg gcaagtactg tgggaccaaa cacctctg   1500 aacttcgttc atcgacgggg atcctctccc tgacctttca cacggacatg gcggtggcca   1560
aggatggctt ctctgcgcgt tactacctgg tccaccaaga gccactagag aactttcagt   1620
gcaatgttcc tctgggcatg gagtctggcc ggattgctaa tgaacagatc agtgcctcat   1680
ctacctactc tgatgggagg tggacccctc aacaaagccg gctccatggt gatgacaatg   1740
gctggacccc caacttggat tccaacaagg agtatctcca ggtggacctg cgcttttaa   1800 ccatgctcac ggccatcgca acacagggag cgatttccag ggaaacacag aatggctact   1860
atgtcaaatc ctacaagctg gaagtcagca ctaatggaga ggactggatg gtgtaccggc   1920
atggcaaaaa ccacaaggta tttcaagcca acaacgatgc aactgaggtg gttctgaaca   1980
agctccacgc tccactgctg acaaggtttg ttagaatccg ccctcagacc tggcactcag   2040
gtatcgccct ccggctggag ctcttcggct gccgggtcac agatgctccc tgctccaaca   2100
tgctggggat gctctcaggc ctcattgcag actcccagat ctccgcctct tccacccagg   2160
aatacctctg gagccccagt gcagcccgcc tggtcagcag ccgctcgggc tggttccctc   2220
gaatccctca ggcccagccc ggtgaggagt ggcttcaggt agatctggga acacccaaga   2280
cagtgaaagg tgtcatcatc cagggagccc gcggaggaga cagtatcact gctgtggaag   2340
ccagagcatt tgtgcgcaag ttcaaagtct cctacagcct aaacggcaag gactgggaat   2400
acattcagga cccccaggacc cagcagccaa agctgttcga agggaacatg cactatgaca   2460
cccctgacat ccgaaggttt gaccccattc cggcacagta tgtgcgggta cccggaga   2520 ggtggtcgcc ggcggggatt gggatgcggc tggaggtgct gggctgtgac tggacagact   2580
ccaagcccac ggtagagacg ctgggaccca ctgtgaagag cgaagagaca accaccccct   2640
```

-continued

```
accccaccga agaggaggcc acagagtgtg gggagaactg cagctttgag gatgacaaag   2700
atttgcagct cccttcggga ttcaattgca acttcgattt cctcgaggag ccctgtggtt   2760
ggatgtatga ccatgccaag tggctccgga ccacctgggc cagcagctcc agcccaaacg   2820
accggacgtt tccagatgac aggaatttct tgcggctgca gagtgacagc cagagagagg   2880
gccagtatgc ccggctcatc agccccctg tccacctgcc ccgaagcccg gtgtgcatgg    2940
agttccagta ccaggccacg ggcggccgcg gggtggcgct gcaggtggtg cgggaagcca   3000
gccaggagag caagttgctg tgggtcatcc gtgaggacca gggcggcgag tggaagcacg   3060
ggcggatcat cctgcccagc tacgactgg agtaccagat tgtgttcgag ggagtgatag    3120
ggaaaggacg ttccggagag attgccattg atgacattcg dataagcact gatgtcccac   3180
tggagaactg catggaaccc atctcggctt ttgcaggtga aattttaaa gtggacatcc    3240
cagaaataca tgagagagaa ggatatgaag atgaaattga tgatgaatac gaggtggact   3300
ggagcaattc ttcttctgca acctcagggt ctggcgcccc ctcgaccgac aaagaaaaga   3360
gctggctgta caccctggat cccatcctca tcaccatcat cgccatgagc tcactgggcg   3420
tcctcctggg ggccacctgt gcaggcctcc tgctctactg cacctgttcc tactcgggcc   3480
tgagctcccg aagctgcacc acactggaga actacaactt cgagctctac gatggcctta   3540
agcacaaggt caagatgaac caccaaaagt gctgctccga ggcatgacgg attgcacctg   3600
aatcctatct gacgtttcat tccagcaaga ggggctgggg aagattacat tttttttcc    3660
tttggaaact gaatgccata atctcgatca aaccgatcca gaataccgaa ggtatggaca   3720
ggacagaaaa gcgagtcgca ggaggaaggg agatgcagcc gcacagggga tgattacccct  3780
cctaggaccg cggtggctaa gtcattgcag gaacggggct gtgttctctg ctgggacaaa   3840
acaggagctc atctctttgg ggtcacagtt ctatttgtt tgtgagtttg tattattatt     3900
attattatta ttattattat attttatttc tttggtctgt gagcaactca agaggcaga    3960
agaggagaat gacttttcca gaatagaagt ggagcagtga tcattattct ccgctttctc   4020
tttctaatca acacttgaaa agcaaagtgt cttttcagcc tttccatctt tacaaataaa   4080
actcaaaaaa gccgtccagc ttatcccatc ctctgattgt cttctgactt aagggattta   4140
ctgtggtgta ggttctgcca gccaacccta caagctgcca tttccagtcc tagcatttaa   4200
gtaggatgtt gttgccttta acttttctta tccagggaa aattgccatt ttagggtcag    4260
catgaacagc tctttcttgt atgcgattta aaacaaactg gaaaggaaac ttcacacgtc   4320
aaaatccata gaagcgcctg gacgaggctt aaagtgcttt gtgagtgaat aggagccatt   4380
cgctaattct agacccacag tgtctggtgg tggggcttcc cttgtggggc ttctggtggt   4440
ggttttgcct tttcttttcc ctcctccatg ttccttctaaa acatatacat atatacatac   4500
acacatacac atattcttca ggtctctaag cccctggaag cagcattgtg tgatattctc   4560
agaggcaggg gaaatagag ggaaaaatag agactattgg tatgttctcc ccatcagcga    4620
gttattgtaa ctggtcacca ctggacggga aggagaacag aggagaggga aagagaagcc   4680
caacctctgt gatcatatga gggccaaggc tgagcagtgt agacagagac cctttgaaat   4740
gcatttgtct ctcaaataga ctagtaaaca ccgacttctc ctttgggtta caaacaccat   4800
ttcaaccttt cgggagagtc agagctagga tgtacaagaa ctgattctaa ccagaagtcc   4860
gcaagtactg tggacaagaa tgcttaacca tgctgcttca gccttgagag acctaggttc   4920
ttacacatat gcacacacgc atacacacat gcacgcacac acacatacac acatgcacgc   4980
acgcacgcat gcacaccaat ttatgttttt attaagtgcc ttgaaaaaat gaagaaaaat   5040
```

```
gtattttccc tttatgtaaa aattagtgaa tatcttatga attaaggcat tcctcttttcc    5100
ctaaccccga tggctccatt cccaagtacc ccaactcact gctgatccta ttaaaggaat    5160
gagtcctgct acccgagtgg tagtcatagc cctagatgac tctcaactac tcttcaaagg    5220
gaggcatcag gaatagaatg aaactgtgtg aaggataaga ttgttcgcat caagatccaa    5280
atcttgattt catattaacg cctaaggatt gcctgtgtgc tggaaatata tttgaaactc    5340
aaccagtatg cccagcctat tgcatatcat tgtcagacca ttttgctgc tgtggtcacc     5400
cacgatttca tttgtcttat acccaggtga aggggaagg gtgaatggga ctggctggtt     5460
cctttaaatg ttaacttatg gaatgctag ttcaaatggt aatgtcacag tgttttgtat     5520
gcagagagca agagttcaac caacagctgt ttattcatgt gtgtgtgtct ttgctgcttt    5580
gagttctctg tatctactgt gtatgtgaat ggtcatgtgg gactcagtgg tggtgttgtg    5640
actttgacct agggtccgag tgtcacagct gatcttggca ctcggcactc attggcacag    5700
tggtagttag aggtgaaaag tagagctgtc aagcccaagg gcttagcttt agggctcctc    5760
ctgagttcgg cccacagtag aagcaagatt ttaactagcc ccttttcctc ttcaccctcc    5820
catgatgcgc agtgttcaga aagctggtaa gtcctaggga tttccagaag tagcctgcag    5880
aagaaggtaa gtttgaaagc cactccaggg gtcctgatgc tgtcatgctc agtgagccat    5940
tttacagttc tccaaagtct agccctgttt cggacctgca cttcacctct aagttatgta    6000
caactcaacc tgcatccctc taaaagtcct atatccatat tcaccattgg ctaatttgag    6060
gccctgagtg ggccttgaat gctaaaaaga agcagggtac gcagggctac atgtagatac    6120
cacaccaagg ctggaggctg gtctgtcata agacagaaag aaagacgctg ggcccaattt    6180
tgacttggcc aggggacacc ttggtgtgtt tgttatcttt atctgtgggt aggctagctg    6240
acccatctcc ttgagtcatt cccttgggaa accccactg ccagtattga tctccttttt     6300
gccttgtact gaatgacaca ttacctccac actctcccgg actaggtggt caacagggcc    6360
acagggttgc tttctgtctt tggtggggca ggggagttga cagggatgag ggtccaagga    6420
ataagcatga atgacaagaa aacaagggaa agagttaacc tgtcacatag caggttaact    6480
ttttcagggt ttgcagttag aggtattcga ccattcactg gctgagccag atcacgggaa    6540
cttgagagct tttactgtga ttcttcaatg taaaaataa acaacaatgt caaactgtgt     6600
ttatatgatt tgtataaagc ctttttaaga ttactattta aataaacatt ataccagaga    6660
taaaaaaaaa a                                                          6671
```

<210> SEQ ID NO 4
<211> LENGTH: 931
<212> TYPE: PRT
<213> ORGANISM: Homo sapiens

<400> SEQUENCE: 4

```
Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
                20                  25                  30

Asn Ser Lys Asp Ala Gly Tyr Ile Thr Ser Pro Gly Tyr Pro Gln Asp
            35                  40                  45

Tyr Pro Ser His Gln Asn Cys Glu Trp Ile Val Tyr Ala Pro Glu Pro
        50                  55                  60

Asn Gln Lys Ile Val Leu Asn Phe Asn Pro His Phe Glu Ile Glu Lys
65                  70                  75                  80
```

-continued

His Asp Cys Lys Tyr Asp Phe Ile Glu Ile Arg Asp Gly Asp Ser Glu
            85                  90                  95

Ser Ala Asp Leu Leu Gly Lys His Cys Gly Asn Ile Ala Pro Pro Thr
        100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
    290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
    450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

-continued

```
Thr Val Lys Gly Val Ile Ile Gln Gly Ala Arg Gly Gly Asp Ser Ile
                500                 505                 510
Thr Ala Val Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
        530                 535                 540
Gln Pro Lys Leu Phe Glu Gly Asn Met His Tyr Asp Thr Pro Asp Ile
545                 550                 555                 560
Arg Arg Phe Asp Pro Ile Pro Ala Gln Tyr Val Arg Val Tyr Pro Glu
                565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
        595                 600                 605
Lys Ser Glu Glu Thr Thr Thr Pro Tyr Pro Thr Glu Glu Glu Ala Thr
610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Leu Glu Glu Pro Cys Gly
                645                 650                 655
Trp Met Tyr Asp His Ala Lys Trp Leu Arg Thr Thr Trp Ala Ser Ser
            660                 665                 670
Ser Ser Pro Asn Asp Arg Thr Phe Pro Asp Asp Arg Asn Phe Leu Arg
        675                 680                 685
Leu Gln Ser Asp Ser Gln Arg Glu Gly Gln Tyr Ala Arg Leu Ile Ser
        690                 695                 700
Pro Pro Val His Leu Pro Arg Ser Pro Val Cys Met Glu Phe Gln Tyr
705                 710                 715                 720
Gln Ala Thr Gly Gly Arg Gly Val Ala Leu Gln Val Val Arg Glu Ala
                725                 730                 735
Ser Gln Glu Ser Lys Leu Leu Trp Val Ile Arg Glu Asp Gln Gly Gly
            740                 745                 750
Glu Trp Lys His Gly Arg Ile Ile Leu Pro Ser Tyr Asp Met Glu Tyr
        755                 760                 765
Gln Ile Val Phe Glu Gly Val Ile Gly Lys Gly Arg Ser Gly Glu Ile
        770                 775                 780
Ala Ile Asp Asp Ile Arg Ile Ser Thr Asp Val Pro Leu Glu Asn Cys
785                 790                 795                 800
Met Glu Pro Ile Ser Ala Phe Ala Gly Glu Asn Phe Lys Val Asp Ile
                805                 810                 815
Pro Glu Ile His Glu Arg Glu Gly Tyr Glu Asp Glu Ile Asp Asp Glu
            820                 825                 830
Tyr Glu Val Asp Trp Ser Asn Ser Ser Ser Ala Thr Ser Gly Ser Gly
        835                 840                 845
Ala Pro Ser Thr Asp Lys Glu Lys Ser Trp Leu Tyr Thr Leu Asp Pro
850                 855                 860
Ile Leu Ile Thr Ile Ile Ala Met Ser Ser Leu Gly Val Leu Leu Gly
865                 870                 875                 880
Ala Thr Cys Ala Gly Leu Leu Leu Tyr Cys Thr Cys Ser Tyr Ser Gly
                885                 890                 895
Leu Ser Ser Arg Ser Cys Thr Thr Leu Glu Asn Tyr Asn Phe Glu Leu
            900                 905                 910
Tyr Asp Gly Leu Lys His Lys Val Lys Met Asn His Gln Lys Cys Cys
```

Ser Glu Ala
    930

<210> SEQ ID NO 5
<211> LENGTH: 766
<212> TYPE: PRT
<213> ORGANISM: Homo sapiens

<400> SEQUENCE: 5

Phe Pro Thr Gln Asp His Leu Pro Ala Thr Pro Arg Val Arg Leu Ser
 1               5                  10                  15

Phe Lys Glu Leu Lys Ala Thr Gly Thr Ala His Phe Phe Asn Phe Leu
            20                  25                  30

Leu Asn Thr Thr Asp Tyr Arg Ile Leu Leu Lys Asp Glu Asp His Asp
        35                  40                  45

Arg Met Tyr Val Gly Ser Lys Asp Tyr Val Leu Ser Leu Asp Leu His
    50                  55                  60

Asp Ile Asn Arg Glu Pro Leu Ile Ile His Trp Ala Ala Ser Pro Gln
65                  70                  75                  80

Arg Ile Glu Glu Cys Val Leu Ser Gly Lys Asp Val Asn Gly Glu Cys
                85                  90                  95

Gly Asn Phe Val Arg Leu Ile Gln Pro Trp Asn Arg Thr His Leu Tyr
            100                 105                 110

Val Cys Gly Thr Gly Ala Tyr Asn Pro Met Cys Thr Tyr Val Asn Arg
        115                 120                 125

Gly Arg Arg Ala Gln Ala Thr Pro Trp Thr Gln Thr Gln Ala Val Arg
    130                 135                 140

Gly Arg Gly Ser Arg Ala Thr Asp Gly Ala Leu Arg Pro Met Pro Thr
145                 150                 155                 160

Ala Pro Arg Gln Asp Tyr Ile Phe Tyr Leu Glu Pro Glu Arg Leu Glu
                165                 170                 175

Ser Gly Lys Gly Lys Cys Pro Tyr Asp Pro Lys Leu Asp Thr Ala Ser
            180                 185                 190

Ala Leu Ile Asn Glu Glu Leu Tyr Ala Gly Val Tyr Ile Asp Phe Met
        195                 200                 205

Gly Thr Asp Ala Ala Ile Phe Arg Thr Leu Gly Lys Gln Thr Ala Met
    210                 215                 220

Arg Thr Asp Gln Tyr Asn Ser Arg Trp Leu Asn Asp Pro Ser Phe Ile
225                 230                 235                 240

His Ala Glu Leu Ile Pro Asp Ser Ala Glu Arg Asn Asp Asp Lys Leu
                245                 250                 255

Tyr Phe Phe Phe Arg Glu Arg Ser Ala Glu Ala Pro Gln Ser Pro Ala
            260                 265                 270

Val Tyr Ala Arg Ile Gly Arg Ile Cys Leu Asn Asp Asp Gly Gly His
        275                 280                 285

Cys Cys Leu Val Asn Lys Trp Ser Thr Phe Leu Lys Ala Arg Leu Val
    290                 295                 300

Cys Ser Val Pro Gly Glu Asp Gly Ile Glu Thr His Phe Asp Glu Leu
305                 310                 315                 320

Gln Asp Val Phe Val Gln Gln Thr Gln Asp Val Arg Asn Pro Val Ile
                325                 330                 335

Tyr Ala Val Phe Thr Ser Ser Gly Ser Val Phe Arg Gly Ser Ala Val
            340                 345                 350

-continued

```
Cys Val Tyr Ser Met Ala Asp Ile Arg Met Val Phe Asn Gly Pro Phe
            355                 360                 365

Ala His Lys Glu Gly Pro Asn Tyr Gln Trp Met Pro Phe Ser Gly Lys
            370                 375                 380

Met Pro Tyr Pro Arg Pro Gly Thr Cys Pro Gly Gly Thr Phe Thr Pro
385                 390                 395                 400

Ser Met Lys Ser Thr Lys Asp Tyr Pro Asp Glu Val Ile Asn Phe Met
            405                 410                 415

Arg Ser His Pro Leu Met Tyr Gln Ala Val Tyr Pro Leu Gln Arg Arg
            420                 425                 430

Pro Leu Val Val Arg Thr Gly Ala Pro Tyr Arg Leu Thr Thr Ile Ala
            435                 440                 445

Val Asp Gln Val Asp Ala Ala Asp Gly Arg Tyr Glu Val Leu Phe Leu
            450                 455                 460

Gly Thr Asp Arg Gly Thr Val Gln Lys Val Ile Val Leu Pro Lys Asp
465                 470                 475                 480

Asp Gln Glu Leu Glu Glu Leu Met Leu Glu Val Glu Val Phe Lys
            485                 490                 495

Asp Pro Ala Pro Val Lys Thr Met Thr Ile Ser Ser Lys Arg Gln Gln
            500                 505                 510

Leu Tyr Val Ala Ser Ala Val Gly Val Thr His Leu Ser Leu His Arg
            515                 520                 525

Cys Gln Ala Tyr Gly Ala Ala Cys Ala Asp Cys Cys Leu Ala Arg Asp
            530                 535                 540

Pro Tyr Cys Ala Trp Asp Gly Gln Ala Cys Ser Arg Tyr Thr Ala Ser
545                 550                 555                 560

Ser Lys Arg Arg Ser Arg Arg Gln Asp Val Arg His Gly Asn Pro Ile
                565                 570                 575

Arg Gln Cys Arg Gly Phe Asn Ser Asn Ala Asn Lys Asn Ala Val Glu
            580                 585                 590

Ser Val Gln Tyr Gly Val Ala Gly Ser Ala Ala Phe Leu Glu Cys Gln
            595                 600                 605

Pro Arg Ser Pro Gln Ala Thr Val Lys Trp Leu Phe Gln Arg Asp Pro
610                 615                 620

Gly Asp Arg Arg Arg Glu Ile Arg Ala Glu Asp Arg Phe Leu Arg Thr
625                 630                 635                 640

Glu Gln Gly Leu Leu Leu Arg Ala Leu Gln Leu Ser Asp Arg Gly Leu
                645                 650                 655

Tyr Ser Cys Thr Ala Thr Glu Asn Asn Phe Lys His Val Thr Arg
            660                 665                 670

Val Gln Leu His Val Leu Gly Arg Asp Ala Val His Ala Ala Leu Phe
            675                 680                 685

Pro Pro Leu Ser Met Ser Ala Pro Pro Gly Ala Gly Pro Pro
690                 695                 700

Thr Pro Pro Tyr Gln Glu Leu Ala Gln Leu Ala Gln Pro Glu Val
705                 710                 715                 720

Gly Leu Ile His Gln Tyr Cys Gln Gly Tyr Trp Arg His Val Pro Pro
            725                 730                 735

Ser Pro Arg Glu Ala Pro Gly Ala Pro Arg Ser Pro Glu Pro Gln Asp
            740                 745                 750

Gln Lys Lys Pro Arg Asn Arg Arg His His Pro Pro Asp Thr
            755                 760                 765
```

-continued

```
<210> SEQ ID NO 6
<211> LENGTH: 1896
<212> TYPE: PRT
<213> ORGANISM: Homo sapiens

<400> SEQUENCE: 6
```

| Met | Pro | Leu | Pro | Pro | Arg | Ser | Leu | Gln | Val | Leu | Leu | Leu | Leu | Leu |
|---|---|---|---|---|---|---|---|---|---|---|---|---|---|---|
| 1 | | | | 5 | | | | | 10 | | | | | 15 |

| Leu | Leu | Leu | Leu | Leu | Pro | Gly | Met | Trp | Ala | Glu | Ala | Gly | Leu | Pro | Arg |
|---|---|---|---|---|---|---|---|---|---|---|---|---|---|---|---|
| | | | | 20 | | | | | 25 | | | | | 30 | |

| Ala | Gly | Gly | Gly | Ser | Gln | Pro | Pro | Phe | Arg | Thr | Phe | Ser | Ala | Ser | Asp |
|---|---|---|---|---|---|---|---|---|---|---|---|---|---|---|---|
| | | | 35 | | | | | 40 | | | | | 45 | | |

| Trp | Gly | Leu | Thr | His | Leu | Val | Val | His | Glu | Gln | Thr | Gly | Glu | Val | Tyr |
|---|---|---|---|---|---|---|---|---|---|---|---|---|---|---|---|
| | 50 | | | | | 55 | | | | | 60 | | | | |

| Val | Gly | Ala | Val | Asn | Arg | Ile | Tyr | Lys | Leu | Ser | Gly | Asn | Leu | Thr | Leu |
|---|---|---|---|---|---|---|---|---|---|---|---|---|---|---|---|
| 65 | | | | | 70 | | | | | 75 | | | | | 80 |

| Leu | Arg | Ala | His | Val | Thr | Gly | Pro | Val | Glu | Asp | Asn | Glu | Lys | Cys | Tyr |
|---|---|---|---|---|---|---|---|---|---|---|---|---|---|---|---|
| | | | | 85 | | | | | 90 | | | | | 95 | |

| Pro | Pro | Pro | Ser | Val | Gln | Ser | Cys | Pro | His | Gly | Leu | Gly | Ser | Thr | Asp |
|---|---|---|---|---|---|---|---|---|---|---|---|---|---|---|---|
| | | | 100 | | | | | 105 | | | | | 110 | | |

| Asn | Val | Asn | Lys | Leu | Leu | Leu | Leu | Asp | Tyr | Ala | Ala | Asn | Arg | Leu | Leu |
|---|---|---|---|---|---|---|---|---|---|---|---|---|---|---|---|
| | | | 115 | | | | | 120 | | | | | 125 | | |

| Ala | Cys | Gly | Ser | Ala | Ser | Gln | Gly | Ile | Cys | Gln | Phe | Leu | Arg | Leu | Asp |
|---|---|---|---|---|---|---|---|---|---|---|---|---|---|---|---|
| | 130 | | | | | 135 | | | | | 140 | | | | |

| Asp | Leu | Phe | Lys | Leu | Gly | Glu | Pro | His | His | Arg | Lys | Glu | His | Tyr | Leu |
|---|---|---|---|---|---|---|---|---|---|---|---|---|---|---|---|
| 145 | | | | | 150 | | | | | 155 | | | | | 160 |

| Ser | Ser | Val | Gln | Glu | Ala | Gly | Ser | Met | Ala | Gly | Val | Leu | Ile | Ala | Gly |
|---|---|---|---|---|---|---|---|---|---|---|---|---|---|---|---|
| | | | | 165 | | | | | 170 | | | | | 175 | |

| Pro | Pro | Gly | Gln | Gly | Gln | Ala | Lys | Leu | Phe | Val | Gly | Thr | Pro | Ile | Asp |
|---|---|---|---|---|---|---|---|---|---|---|---|---|---|---|---|
| | | | 180 | | | | | 185 | | | | | 190 | | |

| Gly | Lys | Ser | Glu | Tyr | Phe | Pro | Thr | Leu | Ser | Ser | Arg | Arg | Leu | Met | Ala |
|---|---|---|---|---|---|---|---|---|---|---|---|---|---|---|---|
| | | | 195 | | | | | 200 | | | | | 205 | | |

| Asn | Glu | Glu | Asp | Ala | Asp | Met | Phe | Gly | Phe | Val | Tyr | Gln | Asp | Glu | Phe |
|---|---|---|---|---|---|---|---|---|---|---|---|---|---|---|---|
| | 210 | | | | | 215 | | | | | 220 | | | | |

| Val | Ser | Ser | Gln | Leu | Lys | Ile | Pro | Ser | Asp | Thr | Leu | Ser | Lys | Phe | Pro |
|---|---|---|---|---|---|---|---|---|---|---|---|---|---|---|---|
| 225 | | | | | 230 | | | | | 235 | | | | | 240 |

| Ala | Phe | Asp | Ile | Tyr | Tyr | Val | Tyr | Ser | Phe | Arg | Ser | Glu | Gln | Phe | Val |
|---|---|---|---|---|---|---|---|---|---|---|---|---|---|---|---|
| | | | | 245 | | | | | 250 | | | | | 255 | |

| Tyr | Tyr | Leu | Thr | Leu | Gln | Leu | Asp | Thr | Gln | Leu | Thr | Ser | Pro | Asp | Ala |
|---|---|---|---|---|---|---|---|---|---|---|---|---|---|---|---|
| | | | 260 | | | | | 265 | | | | | 270 | | |

| Ala | Gly | Glu | His | Phe | Phe | Thr | Ser | Lys | Ile | Val | Arg | Leu | Cys | Val | Asp |
|---|---|---|---|---|---|---|---|---|---|---|---|---|---|---|---|
| | | 275 | | | | | 280 | | | | | 285 | | | |

| Asp | Pro | Lys | Phe | Tyr | Ser | Tyr | Val | Glu | Phe | Pro | Ile | Gly | Cys | Glu | Gln |
|---|---|---|---|---|---|---|---|---|---|---|---|---|---|---|---|
| | 290 | | | | | 295 | | | | | 300 | | | | |

| Ala | Gly | Val | Glu | Tyr | Arg | Leu | Val | Gln | Asp | Ala | Tyr | Leu | Ser | Arg | Pro |
|---|---|---|---|---|---|---|---|---|---|---|---|---|---|---|---|
| 305 | | | | | 310 | | | | | 315 | | | | | 320 |

| Gly | Arg | Ala | Leu | Ala | His | Gln | Leu | Gly | Leu | Ala | Glu | Asp | Glu | Asp | Val |
|---|---|---|---|---|---|---|---|---|---|---|---|---|---|---|---|
| | | | | 325 | | | | | 330 | | | | | 335 | |

| Leu | Phe | Thr | Val | Phe | Ala | Gln | Gly | Gln | Lys | Asn | Arg | Val | Lys | Pro | Pro |
|---|---|---|---|---|---|---|---|---|---|---|---|---|---|---|---|
| | | | 340 | | | | | 345 | | | | | 350 | | |

| Lys | Glu | Ser | Ala | Leu | Cys | Leu | Phe | Thr | Leu | Arg | Ala | Ile | Lys | Glu | Lys |
|---|---|---|---|---|---|---|---|---|---|---|---|---|---|---|---|
| | | | 355 | | | | | 360 | | | | | 365 | | |

| Ile | Lys | Glu | Arg | Ile | Gln | Ser | Cys | Tyr | Arg | Gly | Glu | Gly | Lys | Leu | Ser |
|---|---|---|---|---|---|---|---|---|---|---|---|---|---|---|---|
| | 370 | | | | | 375 | | | | | 380 | | | | |

```
Leu Pro Trp Leu Leu Asn Lys Glu Leu Gly Cys Ile Asn Ser Pro Leu
385                 390                 395                 400

Gln Ile Asp Asp Phe Cys Gly Gln Asp Phe Asn Gln Pro Leu Gly
            405                 410                 415

Gly Thr Val Thr Ile Glu Gly Thr Pro Leu Phe Val Asp Lys Asp Asp
            420                 425                 430

Gly Leu Thr Ala Val Ala Ala Tyr Asp Tyr Arg Gly Arg Thr Val Val
            435                 440                 445

Phe Ala Gly Thr Arg Ser Gly Arg Ile Arg Lys Ile Leu Val Asp Leu
450                 455                 460

Ser Asn Pro Gly Gly Arg Pro Ala Leu Ala Tyr Glu Ser Val Val Ala
465                 470                 475                 480

Gln Glu Gly Ser Pro Ile Leu Arg Asp Leu Val Leu Ser Pro Asn His
                485                 490                 495

Gln Tyr Leu Tyr Ala Met Thr Glu Lys Gln Val Thr Arg Val Pro Val
            500                 505                 510

Glu Ser Cys Val Gln Tyr Thr Ser Cys Glu Leu Cys Leu Gly Ser Arg
            515                 520                 525

Asp Pro His Cys Gly Trp Cys Val Leu His Ser Ile Cys Ser Arg Arg
530                 535                 540

Asp Ala Cys Glu Arg Ala Asp Glu Pro Gln Arg Phe Ala Ala Asp Leu
545                 550                 555                 560

Leu Gln Cys Val Gln Leu Thr Val Gln Pro Arg Asn Val Ser Val Thr
                565                 570                 575

Met Ser Gln Val Pro Leu Val Leu Gln Ala Trp Asn Val Pro Asp Leu
            580                 585                 590

Ser Ala Gly Val Asn Cys Ser Phe Glu Asp Phe Thr Glu Ser Glu Ser
            595                 600                 605

Val Leu Glu Asp Gly Arg Ile His Cys Arg Ser Pro Ser Ala Arg Glu
610                 615                 620

Val Ala Pro Ile Thr Arg Gly Gln Gly Asp Gln Arg Val Val Lys Leu
625                 630                 635                 640

Tyr Leu Lys Ser Lys Glu Thr Gly Lys Lys Phe Ala Ser Val Asp Phe
                645                 650                 655

Val Phe Tyr Asn Cys Ser Val His Gln Ser Cys Leu Ser Cys Val Asn
            660                 665                 670

Gly Ser Phe Pro Cys His Trp Cys Lys Tyr Arg His Val Cys Thr His
            675                 680                 685

Asn Val Ala Asp Cys Ala Phe Leu Glu Gly Arg Val Asn Val Ser Glu
690                 695                 700

Asp Cys Pro Gln Ile Leu Pro Ser Thr Gln Ile Tyr Val Pro Val Gly
705                 710                 715                 720

Val Val Lys Pro Ile Thr Leu Ala Ala Arg Asn Leu Pro Gln Pro Gln
                725                 730                 735

Ser Gly Gln Arg Gly Tyr Glu Cys Leu Phe His Ile Pro Gly Ser Pro
            740                 745                 750

Ala Arg Val Thr Ala Leu Arg Phe Asn Ser Ser Ser Leu Gln Cys Gln
            755                 760                 765

Asn Ser Ser Tyr Ser Tyr Glu Gly Asn Asp Val Ser Asp Leu Pro Val
            770                 775                 780

Asn Leu Ser Val Val Trp Asn Gly Asn Phe Val Ile Asp Asn Pro Gln
785                 790                 795                 800

Asn Ile Gln Ala His Leu Tyr Lys Cys Pro Ala Leu Arg Glu Ser Cys
```

-continued

```
                805                 810                 815
Gly Leu Cys Leu Lys Ala Asp Pro Arg Phe Glu Cys Gly Trp Cys Val
                820                 825                 830

Ala Glu Arg Arg Cys Ser Leu Arg His His Cys Ala Ala Asp Thr Pro
                835                 840                 845

Ala Ser Trp Met His Ala Arg His Gly Ser Ser Arg Cys Thr Asp Pro
850                 855                 860

Lys Ile Leu Lys Leu Ser Pro Glu Thr Gly Pro Arg Gln Gly Gly Thr
865                 870                 875                 880

Arg Leu Thr Ile Thr Gly Glu Asn Leu Gly Leu Arg Phe Glu Asp Val
                885                 890                 895

Arg Leu Gly Val Arg Val Gly Lys Val Leu Cys Ser Pro Val Glu Ser
                900                 905                 910

Glu Tyr Ile Ser Ala Glu Gln Ile Val Cys Glu Ile Gly Asp Ala Ser
                915                 920                 925

Ser Val Arg Ala His Asp Ala Leu Val Glu Val Cys Val Arg Asp Cys
930                 935                 940

Ser Pro His Tyr Arg Ala Leu Ser Pro Lys Arg Phe Thr Phe Val Thr
945                 950                 955                 960

Pro Thr Phe Tyr Arg Val Ser Pro Ser Arg Gly Pro Leu Ser Gly Gly
                965                 970                 975

Thr Trp Ile Gly Ile Glu Gly Ser His Leu Asn Ala Gly Ser Asp Val
                980                 985                 990

Ala Val Ser Val Gly Gly Arg Pro Cys Ser Phe Ser Trp Arg Asn Ser
                995                 1000                1005

Arg Glu Ile Arg Cys Leu Thr Pro Pro Gly Gln Ser Pro Gly Ser
    1010                1015                1020

Ala Pro Ile Ile Ile Asn Ile Asn Arg Ala Gln Leu Thr Asn Pro
    1025                1030                1035

Glu Val Lys Tyr Asn Tyr Thr Glu Asp Pro Thr Ile Leu Arg Ile
    1040                1045                1050

Asp Pro Glu Trp Ser Ile Asn Ser Gly Gly Thr Leu Leu Thr Val
    1055                1060                1065

Thr Gly Thr Asn Leu Ala Thr Val Arg Glu Pro Arg Ile Arg Ala
    1070                1075                1080

Lys Tyr Gly Gly Ile Glu Arg Glu Asn Gly Cys Leu Val Tyr Asn
    1085                1090                1095

Asp Thr Thr Met Val Cys Arg Ala Pro Ser Val Ala Asn Pro Val
    1100                1105                1110

Arg Ser Pro Pro Glu Leu Gly Glu Arg Pro Asp Glu Leu Gly Phe
    1115                1120                1125

Val Met Asp Asn Val Arg Ser Leu Leu Val Leu Asn Ser Thr Ser
    1130                1135                1140

Phe Leu Tyr Tyr Pro Asp Pro Val Leu Glu Pro Leu Ser Pro Thr
    1145                1150                1155

Gly Leu Leu Glu Leu Lys Pro Ser Ser Pro Leu Ile Leu Lys Gly
    1160                1165                1170

Arg Asn Leu Leu Pro Pro Ala Pro Gly Asn Ser Arg Leu Asn Tyr
    1175                1180                1185

Thr Val Leu Ile Gly Ser Thr Pro Cys Thr Leu Thr Val Ser Glu
    1190                1195                1200

Thr Gln Leu Leu Cys Glu Ala Pro Asn Leu Thr Gly Gln His Lys
    1205                1210                1215
```

```
Val Thr Val Arg Ala Gly Gly Phe Glu Phe Ser Pro Gly Thr Leu
1220             1225                 1230

Gln Val Tyr Ser Asp Ser Leu Leu Thr Leu Pro Ala Ile Val Gly
1235             1240                 1245

Ile Gly Gly Gly Gly Gly Leu Leu Leu Leu Val Ile Val Ala Val
1250             1255                 1260

Leu Ile Ala Tyr Lys Arg Lys Ser Arg Asp Ala Asp Arg Thr Leu
1265             1270                 1275

Lys Arg Leu Gln Leu Gln Met Asp Asn Leu Glu Ser Arg Val Ala
1280             1285                 1290

Leu Glu Cys Lys Glu Ala Phe Ala Glu Leu Gln Thr Asp Ile His
1295             1300                 1305

Glu Leu Thr Asn Asp Leu Asp Gly Ala Gly Ile Pro Phe Leu Asp
1310             1315                 1320

Tyr Arg Thr Tyr Ala Met Arg Val Leu Phe Pro Gly Ile Glu Asp
1325             1330                 1335

His Pro Val Leu Lys Glu Met Glu Val Gln Ala Asn Val Glu Lys
1340             1345                 1350

Ser Leu Thr Leu Phe Gly Gln Leu Leu Thr Lys Lys His Phe Leu
1355             1360                 1365

Leu Thr Phe Ile Arg Thr Leu Glu Ala Gln Arg Ser Phe Ser Met
1370             1375                 1380

Arg Asp Arg Gly Asn Val Ala Ser Leu Ile Met Thr Ala Leu Gln
1385             1390                 1395

Gly Glu Met Glu Tyr Ala Thr Gly Val Leu Lys Gln Leu Leu Ser
1400             1405                 1410

Asp Leu Ile Glu Lys Asn Leu Glu Ser Lys Asn His Pro Lys Leu
1415             1420                 1425

Leu Leu Arg Arg Thr Glu Ser Val Ala Glu Lys Met Leu Thr Asn
1430             1435                 1440

Trp Phe Thr Phe Leu Leu Tyr Lys Phe Leu Lys Glu Cys Ala Gly
1445             1450                 1455

Glu Pro Leu Phe Met Leu Tyr Cys Ala Ile Lys Gln Gln Met Glu
1460             1465                 1470

Lys Gly Pro Ile Asp Ala Ile Thr Gly Glu Ala Arg Tyr Ser Leu
1475             1480                 1485

Ser Glu Asp Lys Leu Ile Arg Gln Gln Ile Asp Tyr Lys Thr Leu
1490             1495                 1500

Thr Leu Asn Cys Val Asn Pro Glu Asn Glu Asn Ala Pro Glu Val
1505             1510                 1515

Pro Val Lys Gly Leu Asp Cys Asp Thr Val Thr Gln Ala Lys Glu
1520             1525                 1530

Lys Leu Leu Asp Ala Ala Tyr Lys Gly Val Pro Tyr Ser Gln Arg
1535             1540                 1545

Pro Lys Ala Ala Asp Met Asp Leu Glu Trp Arg Gln Gly Arg Met
1550             1555                 1560

Ala Arg Ile Ile Leu Gln Asp Glu Asp Val Thr Thr Lys Ile Asp
1565             1570                 1575

Asn Asp Trp Lys Arg Leu Asn Thr Leu Ala His Tyr Gln Val Thr
1580             1585                 1590

Asp Gly Ser Ser Val Ala Leu Val Pro Lys Gln Thr Ser Ala Tyr
1595             1600                 1605
```

Asn Ile Ser Asn Ser Ser Thr Phe Thr Lys Ser Leu Ser Arg Tyr
1610                1615                1620

Glu Ser Met Leu Arg Thr Ala Ser Ser Pro Asp Ser Leu Arg Ser
1625                1630                1635

Arg Thr Pro Met Ile Thr Pro Asp Leu Glu Ser Gly Thr Lys Leu
1640                1645                1650

Trp His Leu Val Lys Asn His Asp His Leu Asp Gln Arg Glu Gly
1655                1660                1665

Asp Arg Gly Ser Lys Met Val Ser Glu Ile Tyr Leu Thr Arg Leu
1670                1675                1680

Leu Ala Thr Lys Gly Thr Leu Gln Lys Phe Val Asp Asp Leu Phe
1685                1690                1695

Glu Thr Ile Phe Ser Thr Ala His Arg Gly Ser Ala Leu Pro Leu
1700                1705                1710

Ala Ile Lys Tyr Met Phe Asp Phe Leu Asp Glu Gln Ala Asp Lys
1715                1720                1725

His Gln Ile His Asp Ala Asp Val Arg His Thr Trp Lys Ser Asn
1730                1735                1740

Cys Leu Pro Leu Arg Phe Trp Val Asn Val Ile Lys Asn Pro Gln
1745                1750                1755

Phe Val Phe Asp Ile His Lys Asn Ser Ile Thr Asp Ala Cys Leu
1760                1765                1770

Ser Val Val Ala Gln Thr Phe Met Asp Ser Cys Ser Thr Ser Glu
1775                1780                1785

His Lys Leu Gly Lys Asp Ser Pro Ser Asn Lys Leu Leu Tyr Ala
1790                1795                1800

Lys Asp Ile Pro Asn Tyr Lys Ser Trp Val Glu Arg Tyr Tyr Ala
1805                1810                1815

Asp Ile Ala Lys Met Pro Ala Ile Ser Asp Gln Asp Met Ser Ala
1820                1825                1830

Tyr Leu Ala Glu Gln Ser Arg Leu His Leu Ser Gln Phe Asn Ser
1835                1840                1845

Met Ser Ala Leu His Glu Ile Tyr Ser Tyr Ile Thr Lys Tyr Lys
1850                1855                1860

Asp Glu Ile Leu Ala Ala Leu Glu Lys Asp Glu Gln Ala Arg Arg
1865                1870                1875

Gln Arg Leu Arg Ser Lys Leu Glu Gln Val Val Asp Thr Met Ala
1880                1885                1890

Leu Ser Ser
1895

<210> SEQ ID NO 7
<211> LENGTH: 9071
<212> TYPE: DNA
<213> ORGANISM: Homo sapiens

<400> SEQUENCE: 7
atgccgctgc caccgcggag cctgcaggtg ctcctgctgc tgctgctgtt gctgctgctg      60
ctgccgggca tgtgggctga ggcaggcttg cccagggcag gcgggggttc acagcccccc     120
ttccgcacct tctcggccag cgactgggc ctcacccacc tagtggtgca tgagcagaca     180
ggcgaggtgt atgtgggcgc agtgaaccgc atctataagc tgtcggggaa cctgacactg     240
ctgcgggccc acgtcacggg ccctgtggag gacaacgaga gtgctaccc gccgcccagc     300 gtgcagtcct gccccacgg cctgggcagt actgacaacg tcaacaagct gctgctgctg     360

```
gactatgccg ctaaccgcct gctggcctgt ggcagcgcct cccagggcat ctgccagttc    420
ctgcgtctgg acgatctctt caaactgggt gagccacacc accgtaagga gcactacctg    480
tccagcgtgc aggaggcagg cagcatggcg ggcgtgctca ttgccgggcc accgggccag    540
ggccaggcca agctcttcgt gggcacaccc atcgatggca agtccgagta cttccccaca    600
ctgtccagcc gtcggctcat ggccaacgag gaggatgccg acatgttcgg cttcgtgtac    660
caggatgagt ttgtgtcatc acagctcaag atcccttcgg acacgctgtc caagttcccg    720
gcctttgaca tctactatgt gtacagcttc cgcagcgagc agtttgtcta ctacctcacg    780
ctgcagctag acacacagct gacctcgcct gatgccgccg cgagcacttt cttcacgtcc    840
aagatcgtgc ggctctgtgt ggacgacccc aaattctact cgtacgttga gttccccatt    900
ggctgcgagc aggcgggtgt ggagtaccgc ctggtgcagg atgcctacct gagccggccc    960
ggccgtgccc tggcccacca gctgggcctg gctgaggacg aggacgtgct gttcactgtg   1020
ttcgcccagg ccagaagaa ccgcgtgaag ccaccaaagg agtcagcact gtgcctgttc   1080
acgctcaggg ccatcaagga gaagattaag gagcgcatcc agtcctgcta ccgtggtgag   1140
ggcaagctct ccctgccgtg gctgctcaac aaggagctgg gctgcatcaa ctcgcccctg   1200
cagatcgatg acgacttctg cgggcaggac ttcaaccagc ccctgggggg cacagtcacc   1260
attgagggga cgcccctgtt cgtggacaag gatgatggcc tgaccgccgt ggctgcctat   1320
gactatcggg gccgcactgt ggtattcgcc ggcacgcgaa gtggccgcat ccgcaagatc   1380
ctggtggacc tctcaaaccc cggtggccgg cctgccctgg cctacgagag cgtcgtggcc   1440
caggagggca gccccatcct gcgagacctc gtcctcagcc caaccacca gtacctctac   1500 gccatgaccg agaagcaggt gacgcgggtg cctgtggaga gctgtgtgca gtacacgtcc   1560
tgtgagctgt gtctggggtc acgggacccc cactgtggct ggtgtgtcct gcacagcatc   1620
tgctcgcggc gggacgcctg tgagcgagca gacgagcccc agcgctttgc tgcggacctg   1680
ctgcagtgtg tgcagctgac tgtgcagccc cgcaatgtgt ctgtcaccat gtcccaggtc   1740
ccacttgtgc tgcaggcctg gaacgtgcct gacctctcag ctggcgtcaa ctgctccttc   1800
gaggacttca cggaatctga gagcgtcctg gaggatggcc ggatccactg ccgctcaccc   1860
tccgcccggg aggtggcgcc catcacgcgg ggccagggag accagcgggt ggtgaaactc   1920
tacctaaagt ccaaggagac agggaagaag tttgcgtctg tggacttcgt cttctacaac   1980
tgcagcgtcc accagtcctg cctgtcctgt gtcaacggct cctttcctg ccactggtgc   2040 aaataccgcc acgtgtgcac acacaacgtg gctgactgcg ccttcctgga gggccgtgtc   2100
aacgtgtctg aggactgccc acagatcctg ccctccacgc agatctacgt gccagtggga   2160
gtggtaaaac ccatcaccct ggccgcacgg aacctgccac agccacagtc aggccagcgt   2220
ggatatgagt gcctcttcca catcccgggc agcccggccc gtgtcaccgc cctgcgcttc   2280
aacagctcca gcctgcagtg ccagaattcc tcgtactcct acgaggggaa cgatgtcagc   2340
gacctgccag tgaacctgtc agtcgtgtgg aacggcaact ttgtcattga caccacag   2400 aacatccagg cgcacctcta caagtgcccg gccctgcgcg agagctgcgg cctctgcctc   2460
aaggccgacc cgcgcttcga gtgcggatgg tgcgtggccc agcgccgctg ctccctgcga   2520
caccactgcg ctgccgacac acctgcatcg tggatgcacg cgcgtcacgg cagcagtcgc   2580
tgcaccgacc ccaagatcct caagctgtcc cccgagacgg gcccgaggca gggcggcacg   2640
cggctcacta tcacaggcga gaacctgggc ctgcgattcg aagacgtgcg tctgggcgtg   2700
```

```
cgcgtgggca aggtgctgtg cagccctgtg gagagcgagt acatcagtgc ggagcagatc     2760
gtctgtgaga tcggggacgc cagctccgtg cgtgcccatg acgccctggt ggaggtgtgt     2820
gtgcgggact gctcaccaca ctaccgcgcc ctgtcaccca agcgcttcac cttcgtgaca     2880
ccaaccttct accgtgtgag cccctcccgt gggcctctgt caggggcac ctggattggc      2940
atcgagggaa gccacctgaa cgcaggcagt gatgtggctg tgtcggtcgg tggccggccc     3000
tgctccttct cctggaggaa ctcccgtgag atccggtgcc tgacacccc cgggcagagc      3060
cctggcagcg ctcccatcat catcaacatc aaccgcgccc agctcaccaa ccctgaggtg     3120
aagtacaact acaccgagga ccccaccatc ctgaggatcg accccgagtg gagcatcaac     3180
agcggtggga ccctcctgac ggtcacaggc accaacctgg ccactgtccg tgaaccccga     3240
atccgggcca gtatggagg cattgagagg gagaacggct gcctggtgta caatgacacc      3300
accatggtat gccgcgcccc gtctgtggcc aaccctgtgc gcagcccacc agagctgggg    3360
gagcggccgg atgagctggg cttcgtcatg acaacgtgc gctccctgct tgtgctcaac     3420
tccacctcct tcctctacta ccctgacccc gtactggagc cactcagccc cactggcctg    3480
ctggagctga gcccagctc cccactcatc ctcaagggcc ggaacctctt gccacctgca     3540
cccggcaact cccgactcaa ctacacggtg ctcatcggct ccacaccctg taccctcacc    3600
gtgtcggaga cgcaactgct gtgcgaggcg cccaacctca ctgggcagca aaggtcacg     3660
gtgcgggcag gtggcttcga gttctcgcca gggacactgc aggtgtactc ggacagcctg    3720
ctgacgctgc ctgccattgt gggcattggc ggaggcgggg gtctcctgct gctggtcatc    3780
gtggctgtgc tcatcgccta caagcgcaag tcacgagatg ctgaccgcac actcaagcgg    3840
ctgcagctcc agatggacaa cctggagtcc gcgtggccc tcgaatgcaa ggaagccttt    3900
gcagagctgc agacagacat ccacgagctg accaatgacc tggacggtgc cggcatcccc   3960
ttccttgact accggacata tgccatgcgg gtgctctttc ctgggatcga ggaccaccct    4020
gtgctcaagg agatggaggt gcaggccaat gtggagaagt cgctgacact gttcgggcag    4080
ctgctgacca agaagcactt cctgctgacc ttcatccgca cgctggaggc acagcgcagc   4140
ttctccatgc gcgaccgcgg gaatgtggcc tcgctcatca tgacgcccct gcagggcgag    4200
atggaatacg ccacaggcgt gctcaagcag ctgctttccg acctcatcga aagaacctg    4260
gagagcaaga accaccccaa gctgctactg cgccggactg agtcggtggc agagaagatg    4320
ctaactaact ggttcacctt cctcttgtat aagttcctca aggagtgcgc tggggagccg    4380
ctgttcatgc tgtactgcgc catcaagcag cagatggaga agggcccat tgacgccatc    4440
acgggtgagg cacgctactc cctgagtgag acaagctca tccggcagca gattgactac     4500
aagacactga ccctgaactg tgtgaaccct gagaatgaga atgcacctga ggtgccggtg    4560
aaggggctgg actgtgacac ggtcacccag gccaaggaga agctgctgga cgctgcctac   4620
aagggcgtgc cctactccca gcggcccaag gccgcggaca tggacctgga gtggcgccag    4680
ggccgcatgg cgcgcatcat cctgcaggac gaggacgtca ccaccaagat tgacaacgat   4740
tggaagaggc tgaacacact ggctcactac caggtgacag acgggtcctc ggtggcactg   4800
gtgcccaagc agacgtccgc ctacaacatc tccaactcct ccaccttcac caagtccctc   4860
agcagatacg agagcatgct gcgcacggcc agcagcccg acagcctgcg ctcgcgcacg    4920
cccatgatca cgcccgacct ggagagcggc accaagctgt ggcacctggt gaagaaccac   4980
gaccacctgg accagcgtga gggtgaccgc ggcagcaaga tggtctcgga gatctacttg   5040
acacggctac tggccaccaa gggcacactg cagaagtttg tggacgacct gtttgagacc   5100
```

```
atcttcagca cggcacaccg gggctcagcc ctgccgctgg ccatcaagta catgttcgac   5160
ttcctggatg agcaggccga caagcaccag atccacgatg ctgacgtgcg ccacacctgg   5220
aagagcaact gcctgcccct gcgcttctgg gtgaacgtga tcaagaaccc acagtttgtg   5280
ttcgacattc acaagaacag catcacggac gcctgcttgt cggtggtggc ccagaccttc   5340
atggactcct gctccacctc tgagcacaag ctgggcaagg actcaccctc aacaagctg    5400 ctctacgcca aggacatccc caactacaag agctgggtgg agaggtacta tgcagacatc   5460
gccaagatgc cagccatcag cgaccaggac atgagtgcgt atctggctga gcagtcccgc   5520
ctgcacctga ccagttcaa cagcatgagc gccttgcacg agatctactc ctacatcacc    5580
aagtacaagg atgagatcct ggcagccctg gagaaggatg agcaggcgcg gcggcagcgg   5640
ctgcggagca agctggagca ggtggtggac acgatggccc tgagcagctg agccccagct   5700
gtgatcatcc agcatgatgc agcgtgagga cagctgagca gggaccggga cagccctcac   5760
cgcatgcgtg tggagtgtcc ggtggtgctc gggccgccgc agtgcagcga ctgcccggcc   5820
ctccctcccc tgcctcaccc ggtcgggtcc cggctcttcc tgtgtggagg tgatggtacc   5880
tgccacacca cagctgcgca cacagctgct tgctcagggg ccgggacagc actgggtgct   5940
caggctggcc aaggaccttc attgcctggc aagagctgcc cagtggcctt catgggagaa   6000
gggctgacct ctgagggct gaggggtgag gccaggccc tccaggggga ggggtagcca    6060
gcttgggctg tccccttgag accaggacaa gaggctgggg gtgtcagcat tcccagcttt   6120
ccaagctgcc cccaggcggc agagtctgag ggtcccgggg cccggttggc agctggagaa   6180
agaggcaaaa agcccgtagc cgggcaagag gagctcaagt cggtctgggc ccgttgccac   6240
cgactcccac ctccagcacc catgcccgct gcaccgctgc catcctcaga ttcaccgcgt   6300
gctctgcgcg gccgaggccg gagcaccaca tccacctcgc cccagagagg ctctgctccc   6360
tcctatggag gggctgtggg ccaggctgct cagactcctg ggtggcttcc agacggaccg   6420
ggcagcccct ctccgtcctc agggctgtgc ctctgggagc cactgggcca ggggcccgg    6480 gtcgcagaga gcacgttccc gttatttatt ccctccgcg tcctacacag gctgccctgg    6540
cagctgtctt caagggtagg ctgagctccc caccctggag cccctgaggg cggcccctga   6600
gcactcctct ctctccactc tctctgtccc tgcccagcg gcttccagtg tggcatctca    6660
gcagtgtcct ggcccctcca gagcagtggg acatctgggg actgttttg tgtttagggg    6720 aaaaaattct gctgcactct gcttgggcct tgaggtctgt ggcagggctc ctctggcccg   6780
cagtggcctg gatctatctg ggccatgagt gacgggcagt gaccagaggg actgaggcc    6840 agcggtgtcc acccttgccc tcagcaagag agaatgcatt cttaaaagaa agctgtacat   6900
gtatatatat gcatatatat atatgtggct ctagcctcag gctccagccc cagtgggta    6960 ctgtacagtt aactgaagaa gaattttaaa gacgatttga acaagaaaat gaaggcagtg   7020
ggaaagcaat gccaaatggt tgtggagaaa gtggccggag cctccctgga gtggagcagc   7080
cctgaagcct gtgccccccg acctgcgggc cgctgttttg gtttgacatg acaaggaaag   7140
gacttcctgc tgaccctgag agcctctggg gtgccgcggc accacggggc atgcatgatt   7200
gtgctagcgt ttagtctgag ttgatctttt taaaactgca agtgttgaat actagaggtt   7260
gttagaccct tttttatgtt ttttaattaa tcagtcactt gtaaaagcaa acaagcggtc   7320 catcccttt tcaaggtcac ttttttgatg gtaccgaaga tcccatggac attaagggac    7380
agctaactgt ggccagactc agccccatgt ccttggccag gcccaaggag aggactcggc   7440
```

-continued

```
cccatggggt gtgccagtct tgcagtccgc cccagctgag tagcgtgagc cagatgacgc    7500
cacagagacc cgcctcttcc ctgaacgcgg gtcggtgtgg agtcagtgac tgctgactca    7560
gggagctcct tggccccgtg ggcactgtgc cagggctggg gccttctgct gctgccacac    7620
ccagctcagg cctgggccag cccctgcccc cagcccactg aggggtggg cttactccct     7680
gggcagtctt gggggccaga gctgaggcca gtccatatta cagtggctgg gctgtttttt    7740
tcagtagccc ctagcattgg ctgggattcc tgttcctggg tgcgcctcca cctcccttct    7800
gatgtttcct ggctatggtg gggtgggaac ctcagtttcc cccaaagtct tccctggatg    7860
ctggcttcag gttgaagtcc ctggttcttc cagttcctca cgggttaggt aggggctcct    7920
gcatcacctt cagaatccag ttccaacccc cactctcctt aggccttgtg ctctgctctg    7980
ccctgccagg ctgcccttgt ccatgtgagt agcatgggcg ggtggtgggg acggcagtgg    8040
tgatgaaggg ggtgcaccac aggcctcatg aagcagttcc cacatgggcg tgtggctggg    8100
gcgtggccac cacagagcac atggctgtgt ctaggcgcaa gcactttagc agtatctgtt    8160
tacatgcgca aggatcaagc cgactacctg tgctgtctac tgggacagca gtctccgagc    8220
tactccgtac ctccctctgc caggtcgtgg agttaggccc cagtccctac ttgtcactgg    8280
ttcccactgt gctcctaact gtgcagcacc tgggagctct ggcctggggc tggaggccct    8340
ggtaggagct gcagttggag gccgttctgt gcccagcagc ggtgagcggc tcccatgggc    8400
cctgtgtctg cagggagcca gggctgcggc acatgtgctg tgaaactggc acccacctgg    8460
cgtgctgctg ccgccacttg cttcctgcag cacctcctac cctgctccgt gtcctccctc    8520
tccccgcgcc tggctcagga gtgctggaaa agctcacgcc tcggcctggg agcctggcct    8580
cttgatatac ctcgagcttc ccctgtgctc cccagcccca ggaccactgg cccttggcc    8640
tgaggggctg ggggccccac gacctgcagc gtcgagtccg ggagagagcc cggagcggcg    8700
tgccatctcg gctcggcctt gctgagagcc tccgccctgg ctttctccct gtctggattc    8760
agtggctcac gttggtgcta cacagctaga atagatatat ttagagagag agatattttt    8820
aagacaaagc ccacaattag ctgtccttta acaccgcaga accccctccc agaagaagag    8880
cgatccctcg gacggtccgg gcgggcaccc tcagccgggc tctttgcaga agcagcaccg    8940
ctgactgtgg gcccggccct cagatgtgta catatacggc tatttcctat tttactgttc    9000
ttcagattta gtacttgtaa ataaacacac acattaagga gagattaaac atttttgcta    9060
aaagctaaaa a                                                        9071
```